US006939693B2

(12) United States Patent
Lorbert et al.

(10) Patent No.: US 6,939,693 B2
(45) Date of Patent: Sep. 6, 2005

(54) ENANTIOSELECTIVE OLIGOMERIZATION OF α-HYDROXY CARBOXYLIC ACIDS AND α-AMINO ACIDS

(75) Inventors: Stephen J. Lorbert, St. Louis, MO (US); Charles S. Schasteen, St. Charles, MO (US); Paul K. S. Nam, Rolla, MO (US); Daniel Forciniti, Rolla, MO (US); Mathur P. Rajesh, Rolla, MO (US); Shubhender Kapila, Rolla, MO (US)

(73) Assignee: Novus International, Inc., St. Louis, MO (US)

(*) Notice: Subject to any disclaimer, the term of this patent is extended or adjusted under 35 U.S.C. 154(b) by 202 days.

(21) Appl. No.: 10/136,974

(22) Filed: May 2, 2002

(65) Prior Publication Data

US 2003/0143661 A1 Jul. 31, 2003

Related U.S. Application Data

(63) Continuation-in-part of application No. 09/699,946, filed on Oct. 30, 2000, now Pat. No. 6,605,590.
(60) Provisional application No. 60/288,196, filed on May 2, 2001, and provisional application No. 60/162,725, filed on Oct. 29, 1999.

(51) Int. Cl.[7] .............................................. C12P 13/04
(52) U.S. Cl. .................... 435/106; 435/280; 528/361
(58) Field of Search ........................... 435/106, 280; 528/361

(56) References Cited

U.S. PATENT DOCUMENTS

| | | | |
|---|---|---|---|
| 3,803,327 A | 4/1974 | Fujimaki et al. | |
| 3,966,985 A | 6/1976 | Jonas | |
| 4,116,768 A | 9/1978 | Isowa et al. | |
| 4,119,493 A | 10/1978 | Isowa et al. | |
| 4,172,072 A | 10/1979 | Ashmead | |
| 4,393,228 A | 7/1983 | Sawada | |
| 4,701,328 A | 10/1987 | Bercovici | |

(Continued)

FOREIGN PATENT DOCUMENTS

| | | |
|---|---|---|
| AU | A-40736/85 | 10/1986 |
| EP | 0 031 527 A2 | 7/1981 |
| FR | 2 708 938 A1 | 2/1995 |
| GB | 2 066 266 A | 7/1981 |
| JP | 03 183495 A | 9/1991 |
| JP | 06 316557 A | 4/1993 |
| WO | WO 95/18781 A1 | 7/1995 |
| WO | WO 98/11126 A1 | 3/1998 |
| WO | WO 01/27074 A1 | 4/2001 |
| WO | WO 01/56980 A1 | 8/2001 |

OTHER PUBLICATIONS

Chen, C.-S., et al., J. Am. Chem. Soc., 109, 2812–2817 (1987).*

(Continued)

Primary Examiner—Herbert J. Lilling
(74) Attorney, Agent, or Firm—Senniger Powers

(57) ABSTRACT

An enzymatic synthesis and composition of oligomers and co-oligomers comprised of α-hydroxy carboxylic acids and α-amino acids or peptides is disclosed. In a preferred embodiment, a α-hydroxy carboxylic acid with a specific chiral configuration is linked by an amide linkage to a α-amino acid specific with a specific chiral configuration or linked by an amide linkage to a peptide made up of α-amino acid monomers having identical chiral configurations. Proteolytic enzymes catalyze oligomerization of the α-hydroxy carboxylic acid and α-amino acid. The degree and distribution of oligomerization varies upon the type and concentrations of different reaction mixtures utilized and upon the length of allowed reaction time. The resultant oligomers may be provided to animals such as ruminants as bioavailable amino acid supplements that are resistant to degradation in the rumen and other animals such as swine, poultry and aquatic animals.

1 Claim, 76 Drawing Sheets

MALDI-TOF SPECTRA OF METHIONINE OLIGOMERS
PAPAIN CATALYZED SYNTHESIS, pH 5.5, 24 HOURS INCUBATION

U.S. PATENT DOCUMENTS

| | | | |
|---|---|---|---|
| 4,806,473 A | | 2/1989 | Johansen et al. |
| 4,940,662 A | | 7/1990 | Yamazaki |
| 5,167,957 A | | 12/1992 | Webb, Jr. et al. |
| 5,304,470 A | | 4/1994 | Fischer et al. |
| 5,374,428 A | | 12/1994 | Hansen et al. |
| 5,625,030 A | * | 4/1997 | Williams et al. ............ 528/361 |
| 5,637,766 A | | 6/1997 | Hsu et al. |
| 5,663,409 A | | 9/1997 | Blackburn et al. |
| 5,670,332 A | | 9/1997 | Kuhl et al. |

OTHER PUBLICATIONS

So, et al., Protease–Catalyzed Tripeptide (RGD) Synthesis, Enzyme and Microbial Technology, 2000, pp. 108–114.

López–Fandiño, et al., Protease–Catalyzed Synthesis of Oligopeptides in Heterogenous Substrate Mixtures, Biotechnology and Bioengineering, May 1994, pp. 1024–1030, vol. 43, No. 11.

Gill, et al., Enzymatic Oligopeptide Synthesis Using a Minimal Protection Strategy: Sequential Assembly of a Growing Oligopeptide Chain, 1995, Journal of American Chemical Society, pp. 6175–6181, vol. 117.

Stoineva, et al., Enzymatic Synthesis Design and Enzymatic Synthesis of Aspartame, Tetrahedron, 1992, pp. 1115–1122, vol. 48 No. 6.

David L. Coffen, Enzyme–Catalyzed Reactions, Chiral Separations: Applications and Technology, American Chemical Society, 1996, pp. 59–91.

Nakanishi, et al., Continuous Peptide Synthesis in a Water-immiscible Organic Solvent with an Immobilized Enzyme, Annals New York Academy of Sciences, pp. 652–655, no date.

Harrison, et al., Catalytic Mechanism of the Enzyme Papain: Predictions with a Hybrid Quantum Mechanical/Molecular Mechanical Potential, Journal of American Chemical Society, 1997, pp. 12285–12290, vol. 119.

Tseng, et al., Enzymic Synthesis of Oligopeptide III. The Optimal Condition of Papain–catalyzed Peptide Bond Formation, Proc. Natl. Sci. Counc., 1979, pp. 42–45, vol. 3 No. 1.

Stehle, et al., Papain–catalysed Synthesis of Dipeptides: A Novel Approach Using Free Amino Acids as Nucleophiles, Enzyme, Microb. Technol., Jan. 1990, pp. 56–60, vol. 12.

Chou, et al., Enzymatic Synthesis of Oligopeptide. Part I. Papain–catalyzed Synthesis of Dipeptide, Tripeptide and Tetrapeptide, Journal of the Chinese Chemical Society, 1978, pp. 215–218, vol. 25 Issue 4.

Auriol, et al., Synthesis of Amino–acid Derivatives and Dipeptides with an Original Peptidase Enzyme, Biomedica Biochimica Acta, 1991, pp. 163–168, vol. 50.

Jost, et al, Enzymatic Peptide Synthesis. Papain Catalyzed Oligomerization of Amino Acid Esters, 1979, pp. 601–604.

Anderson, et al., Papain–induced Oligomerization of a–Amino Acid Esters, Helvetica Chimica Acta, 1979, pp. 488–497, vol. 62.

Oaki, et al., One Step Synthesis of Inverted Aspartame Type Sweetener, Ac–Phe–Lys, Using Chemically Modified Chymotrypsin, Bioscience, Biotechnology, and Biochemistry, 1999, pp. 1156–1159, vol. 63, No. 7.

Nakanishi, et al., Design of Proteinase—Catalyzed Synthesis of Oligopeptides in an Aqueous–Organic Biphasic System, Bio/Technology, May 1986, pp. 452–454, vol. 4.

Kühn, et al., Boilysin and Thermolysin in Dipeptide Synthesis: A Comparative Study, Biotechnology and Applied Biochemistry, 2002, pp. 71–76, vol. 36.

Kisee, et al., Enzymatic Reactions in Aqueous–Organic Media. VI. Peptide Synthesis by $\alpha$–Chymotrypsin in Hydrophilic Organic Solvents, Journal of Biotechnology, 1988, pp. 279–289, vol. 8.

Riechmann, et al., Peptide Synthesis Catalyzed by the Serine Proteinase Chymotrypsin and Trypsin, Biochimica et Biophysica Acta, 1985, pp. 164–172, vol. 830.

Saltman, et al., Co–Oligopeptides of Aromatic Amino Acids and Glycine with Variable Distance Between the Aromatic Residues. VII. Enzymatic Synthesis of N–Protected Peptide Amides, Biopolymers, 1977, pp. 631–638, vol. 16.

Pantaleone, et al., Enzymatic Synthesis of Aspartame Precursors, Science for the Food Industry of the 21st Century; Biotechnology, Supercritical Fluids, Membranes and Other Advanced Technologies for Low Calorie, 1993, pp. 173–193.

Antonovics, et al., Amino–acids and Peptides. Part XXV. The Mechanism of the Base–catalysed Racemisation of the p–Nitrophenyl Esters of Acylpeptides, Journal of the Chemical Society, 1967, pp. 595–601, vol. 7.

Schuster, et al., Enzyme–Catalyzed Peptide Synthesis In Ice, Tetrahedron, 1990, 46(24), pp. 8093–8102, ISSN: 0040–4020.

Salih, et al., Differences in the Chemical and Catalytic Characteristics of Two Crystallographically 'Identical' Enzyme Catalytic Sites. Characterization of Actinidin and Papain by a Combination of pH–Dependent Substrate Catalysis Kinetics and Reactivity Probe Studies Targeted on the Catalytic–Site Thiol Group and its Immediate Microenvironment, Biochemical Journal, 1987, 247(1), 181–93, ISSN: 0306–3275.

Furutani, et al., Resolution of N–acetyl–DL–Methionine Methyl Ester by Protease–Catalyzed Hydrolysis with Mild Base as the pH Control Reagent, Biotechnology Letters, 1999, 21(12) 1101–1105, ISSN: 0141–5492.

Reid, et al., Variation in Aspects of Cysteine Proteinase Catalytic Mechanism Deducted by Spectroscopic Observation of Dithioester Intermediates, Kinetic Analysis and Molecular Dynamics Simulations, Biochemical Journal, 2001, 357(2) 343–352, ISSN: 0264–6021.

Morihara, et al., Peptide Bond Synthesis Catalyzed By Subtilisin, Papain, and Pepsin, Journal of Biochemistry, Feb. 1981, 89(2), 385–95, ISSN: 0021–924X.

Fischer, et al., A Novel Approach to Enzymic Peptide Synthesis Using Highly Solubilizing N$\alpha$–Protecting Groups of Amino Acids, Biocatalysis, 1994, 8(4) 289–307, ISSN: 0886–4454.

Fan, et al., Prediction of Aqueous Phase pH for Enzymatic Synthesis of Peptides in Aqueous–Organic Biphasic Systems, Journal of Chemical Technology & Biotechnology, 2001, 76(8) 851–856, ISSN: 0268–2575.

Braun, et al., Papain–Catalyzed Esterification of N$\alpha$–protected Amino Acids and Dipeptides with Ethanol in Different Organic Systems, Pharmazie, 1997, 52(3) 203–206, ISSN: 0031–7144.

Wu, et al., Enzymic Synthesis of Oligopeptide IV. The Synthesis of Chemotactic Peptides, Proc. Natl. Sci. Counc., 1981, pp. 17–20.

Kühn, et al., Boilysin and Thermolysin in Dipeptide Synthesis: A Comparative Study, Biotechnol. Appl. Biochem., 2002, 36, pp. 71–76, vol. 36.

W. Kullman, Protease–Catalyzed Peptide Synthesis, Advances in the Biosciences, 1987, vol. 65, pp. 135–140.

Rawlings, et al., Families of Cystein Peptidases, Methods in Enzymology, 1994, pp. 461–487, vol. 244.

John K. Inman, Peptide Synthesis with Minimal Protection of Side–Chain Functions, The Peptides, 1981, pp. 254–302, vol. 3.

Miyazawa, et al., Enzymatic Synthesis of Peptides Containing Non–Protein Amino Acids, Peptide Chemistry, 1991, pp. 373–378.

Fernandez, et al., Enzymatic Synthesis of Peptides Containing Unnatural Amino Acids, Enzyme and Microbial Technology, 1995, pp. 964–971, vol. 17.

Morihara, et al., Peptide Bond Synthesis Catalyzed by Subtilisin, Papain, and Pepsin, Journal of Biochem., 1981, vol. 89, pp. 385–395.

Lozano, et al., One–Step Synthesis of Gly–Gly–PheNH$_2$ from N–Unprotected Amino Acid Derivatives by Papain In One–Phase Liquid Media, Biotechnology Letters, Oct. 1992, vol. 14 No. 10, pp. 933–936.

Irokawa, et al., A Methodological Study of the Enzymatic Synthesis of the Tripeptide Z–Cys(Bzl)–Tyr–Ile–OtBu, Peptide Research, 1991, vol. 4 No. 6, pp. 340–346.

Christensen, et al., Factors Affecting Efficacy of Methionine Hydroxy Analogue for Chicks Fed Practical Diets[1], Poultry Science, 1980, pp. 2485–2491, vol. 59, No. 11, Utah State University, Logan, Utah.

Jonathan S. Dordick, Enzymatic Catalysis in Monophasic Organic Solvents, Enzyme Microb. Technol., Apr. 1989, vol. 11, pp. 194–211.

Isono, et al., Synthesis of Aspartame Precursor Using Protease Suspended in Microaqueous Molten Amino Acids Mixture, Biocatalysis and Biotransformation, 2002, vol. 20(6), pp. 391–395.

Oaki, et al., One Step Synthesis of Inverted Aspartame Type Sweetener, Ac–Phe–Lys, Using Chemically Modified Chymotrypsin, Biosci. Biotechnol. Biochem., 1999, 63(7), pp. 1156–1159.

Falender, et al., Enzymatic Oligomerization of the Tetrapeptide Ester Allylglycine–Phenylalanine–Phenylalanine–Allylglycine Ethyl Ester, Biocatalysis and Biotransformation, 1995, vol. 13, pp. 131–139.

Kowlessur, et al., Dependence of the $P_2$–$S_2$ Stereochemical Selectivity of Papain on the Nature of the Catalytic–Site Chemistry, Biochem. Journal, 1990, vol. 266, pp. 653–660.

Kung–Tsung Wang, Use of Enzymes as Catalyst in Organic Synthesis, Department of Chemistry, National Taiwan University, pp. 13–28, no date.

International Search Report from the US International Search Authority dated Apr. 10, 2003.

Rajesh et al., Synthesis and Characterization of Methionine and 2–Hydroxy–4[methyl thio] Butanoic Acid (HMB) Co–oligomers, University of Missouri–Rolla, Missouri, submitted to J. Chromatography, 2000.

Rajesh et al., Synthesis and Characterization of αAcid αAmino Acid and Hetero–Oligomers, University of Missouri–Rolla, Missouri, Pittcom 2001, Mar. 4–9, 2001, New Orleans, LA.

Rajesh et al., Synthesis and Characterization of MHBA–Methionine and MHBA–Lysine Co–oligomers, University of Missouri–Rolla, Missouri, Pittcon 2000, Mar. 12–17, 2000, New Orleans, LA.

Rajesh et al., Synthesis and Characterization of α–Hydroxy Acid and Amino Acid Co–oligomers, University of Missouri–Rolla, Missouri 19th International Symposium on the Separation and Analysis of Proteins, Peptides and Polynucleotides, Oct. 31–Nov. 3, 1999.

Lozano et al., One–Step Synthesis of Gly–Gly–PheNH$_2$ from N–Unprotected Amino Acid Derivatives by Papain in One–Phase Liquid Media, Bitechnology Letters, vol. 14, No. 10, Oct. 1992, pp. 933–936.

Cerovsky et al., Nucleophile Specficity of Subtilisin in an Organic Solvent with Low Water Content: Investigation via Acyl Transfer Reactions, Biotechnology and Bioengineering, vol. 49, 1996, pp. 553–558.

Lozano et al., Peptide Synthesis by Papain in Alkali Halide Media, Biocatalysis and Biotransformation, vol. 13, pp. 255–269, 1996.

Kasai et al., Correlation between Molecular Weight Distribution of Oligo–L–methionine Prepared by Papain–catalyzed Polymerization and Its Supplementary Effect in a Low Protein Diet, Bioscience, Biotechnology, and Biochemistry, vol. 56, Nov. 1992.

Spindler et al, Amino Acid Analysis of Feedstruffs: Determination of Methionine and Cystine after Oxidation with Performic Acid and Hydrolysis, Journal of Agricultural and Food Chemistry, vol. 32, 1984, pp. 1366–1371.

Yamashita et al, A Novel One–step Process for Enzymatic Incorporation of Amino Acids into Proteins: Application to Soy Protein and Flour for Enhancing Their Methionine Levels, Agricultural and Biological Chemistry, vol. 43, May 1979, pp. 1065–1068.

Jost et al., Papain Catalyzed Oligomerization of α–Amino Acids. Synthesis and Characterization of Water–Insoluble Oligomers of L–Methionine, Helvetica Chimica Acta, vol. 63, 1980, pp. 375–384.

Ferjancic et al., Papain–Catalyzed Polymerization of Amino Acids in Low Water Organic Solvents, Biotechnology Letters, vol. 13, No. 3, pp. 161–166, 1991.

Wallace et al., Analysis of Peptide Metabolism by Ruminal Microorganisms, Applied and Environmental Microbiology, vol. 55, No. 9, Sep. 1989, pp. 2372–2376.

Wallace, Ruminal Microbial Metabolism of Peptides and Amino Acids, American Institute of Nutrition, 1996, pp. 1326S–1334S.

Wallace, Acetylation of Peptides Inhibits their Degradation by Rumen Micro–Organisms, British Journal of Nutrition, vol. 68, 1992, pp. 365–372.

Kitaguchi et al., Enzymatic Resolution of Racemic Amines: Crucial Role of the Solvent, Journal of the American Chemical Society, vol. 111, 1989, pp. 3094–3095.

Fitzpatrick et al., How Can the Solvent Affect Enzyme Enantioselectivity?, Journal of the American Chemical Society, vol. 113, pp. 3166–3171, 1991.

Arai et al., A Novel One–step Process for Enzymatic Incorporation of Amino Acids into Proteins: Papain–catalyzed Polymerization of L–Methionine Ethyl Ester and Its Regulation by Adding a Protein Substrate, Agricultural and Biological Chemistry, vol. 43, May 1979, pp. 1069–1074.

Ohkubo et al., Catalytic Activity of a Novel Water–Soluble Cross–Linked Polymer Imprinted by a Transition–state Analogue for the Stereoselective Hydrolysis of Enantiomeric Amino Acid Esters, Polymer, vol. 37, No. 17, 1996, pp. 3993–3995.

Yamashita et al., Stereoselective Polymerization of α–Amino Acid N–Carboxyanhybrides with Nickel dl–2–Methylbutyrate–Tri–n–butylphosphine Catalyst System, Macromolecules, vol. 7, No. 4, 1974, pp. 410–415.

Nozawa et al., On the Mechanism of the Stereoselective Hydrolysis of Phenylalanine Esters Catalyzed by Poly(L–l-ysine)–Copper(II) Complexes, Die Makromolekulare Chemie, vol. 161, 1972, pp. 289–291.

Wallace, et al., Analysis of Peptide Metabolism by Ruminal Microorganisms, Applied and Environmental Microbiology, Sep. 1989, pp. 2372–2376.

Lee, et al., Papain Catalyzed Polymerization of L–∝–Amino Acid Methyl Esters with Hydrophobic Side Chains, Chemistry Express, vol. 5, No. 10, 1990, pp. 741–744.

Kashe, et al., Stereo–and Sequence Specificity of Serine Proteases in Peptide Synthesis, Biomed, Biochim. Acta 50, 1991, 10/11, S 38–S 43.

Gololobov, et al., Nucleophile Specificity in ∝–chymotrypsin– and subtilisin– (*Bacillus subtilis* strain 72) Catalyzed Reactions, Biochimica et Biophysica Acta, 1160, 1992, pp. 188–192.

Wallace, et al., Breakdown of N–Terminally Modified Peptides and an Isopeptide by Rumen Microorganisms, Applied and Environmental Microbiology, Sep. 1993, pp. 3147–3149.

Itsuno et al., Novel Polymer–Supported Chiral Catalysts for Asymmetric Synthesis, Macromolecular Symposia, vol. 105, Mar. 1996, pp. 155–159.

Wang, et al., Cross–Linked Crystals of Substilisin: Versatile Catalyst for Organic Synthesis, The Journal of Organic Chemistry, vol. 62, No. 11, May 30, 1997, pp. 3488–3495.

Webb, Jr., et al., Absorption of Amino Acids and Peptides, CRC Principles of Protein Nutrition of Ruminants, Chapter 7, pp. 127–146, (1994).

Sluyterman, et al., Sigmoidal Progress Curves In The Polymerization Of Leucine Methyl Ester Catalyzed By Papain, *Biochimica Et Biophysica Acta*, vol. 289, vol. E41, 1972, pp. 194–202.

Ohya, et al., Polycondensation Of Alpha–hydroxy Acids By Enzymes Or PEG–modified Enzymes, *Journal Of Macromolecular Science A. Pure And Applied Chemistry*, vol. A32, No. 2, 1995, pp. 179–190, Abstract.

Ching et al., Quantitative Analyses of Biochemical Kinetic Resolution of Enantiomers. 2. Enzyme–Catalyzed Esterifications in Water–Organic Solvent Biphasic Systems, Journal of the American Chemical Society, vol. 109, 1987, pp. 2812–2817.

Tobe, et al., Synthesis and Structure–Activity Relationships of Amastatin Analogues, Inhibitors of Aminopeptidase A, Agric. Biol. Chem., vol. 46, No. 7, 1982, pp. 1865–1872.

Plegge, et al., Effect of Roasting on Utilization of Soybean Meal By Ruminants, Journal of Animal Science, vol. 55, No. 2, Aug. 1982, pp. 395–401.

Faldet, et al., Chemical, In Vitro, and In Vivo Evaluation of Soybeans Heat–Treated by Various Processing Methods, Journal of Dairy Science, vol. 75, No. 3, Mar. 1992, pp. 789–795.

* cited by examiner

FIG. 3 HPLC OF METHIONINE OLIGOMER SULFONES (24 hrs Rxn) CHROMATOGRAPHY OF METHIONINE OLIGOMER SULFONES, pH 5.5, INCUBATION PERIOD 24 HOURS.

FIG. 4 HPLC OF MHBA - METHIONINE OLIGOMER SULFONES (10 min Rxn.) CHROMATOGRAPHY OF MHBA-Met CO-OLIGOMER SULFONES, pH 5.5, INCUBATION PERIOD 10 MINUTES.

FIG. 5 HPLC OF MHBA - METHIONINE OLIGOMER SULFONES (24 hrs Rxn.) CHROMATOGRAPHY OF MHBA - Met CO-OLIGOMER SULFONES, pH 5.5, INCUBATION PERIOD 24 HOURS.

RM - LysEE + MHBAEE Co-Olgtn

LysEE + MHBAEE Co-Olgtn in 3 Phase

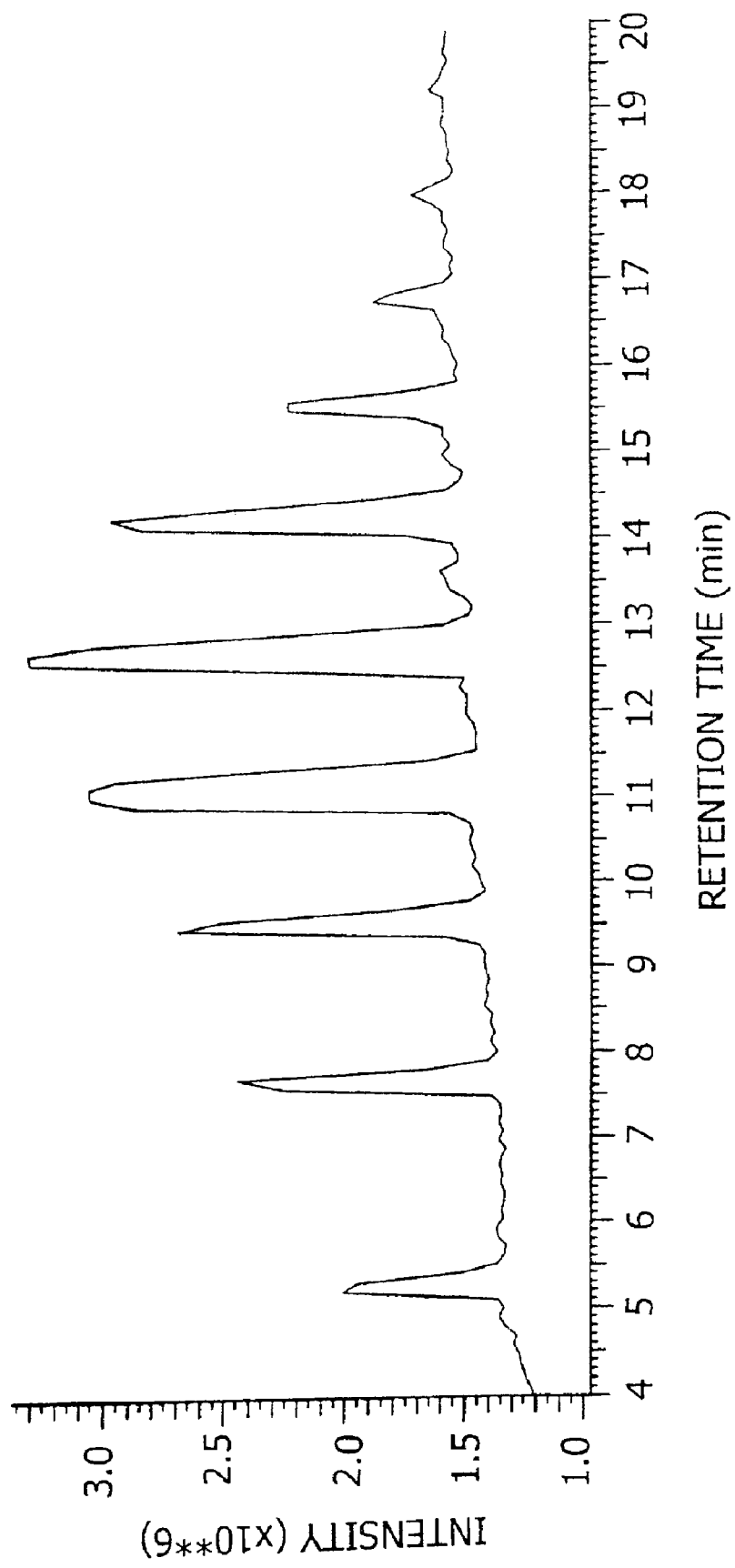
FIG. 14B CHROMATOGRAMS OF PERSULFONATED METHIONINE OLIGOMERS
POSITIVE ION TOTAL ION CHROMATOGRAM

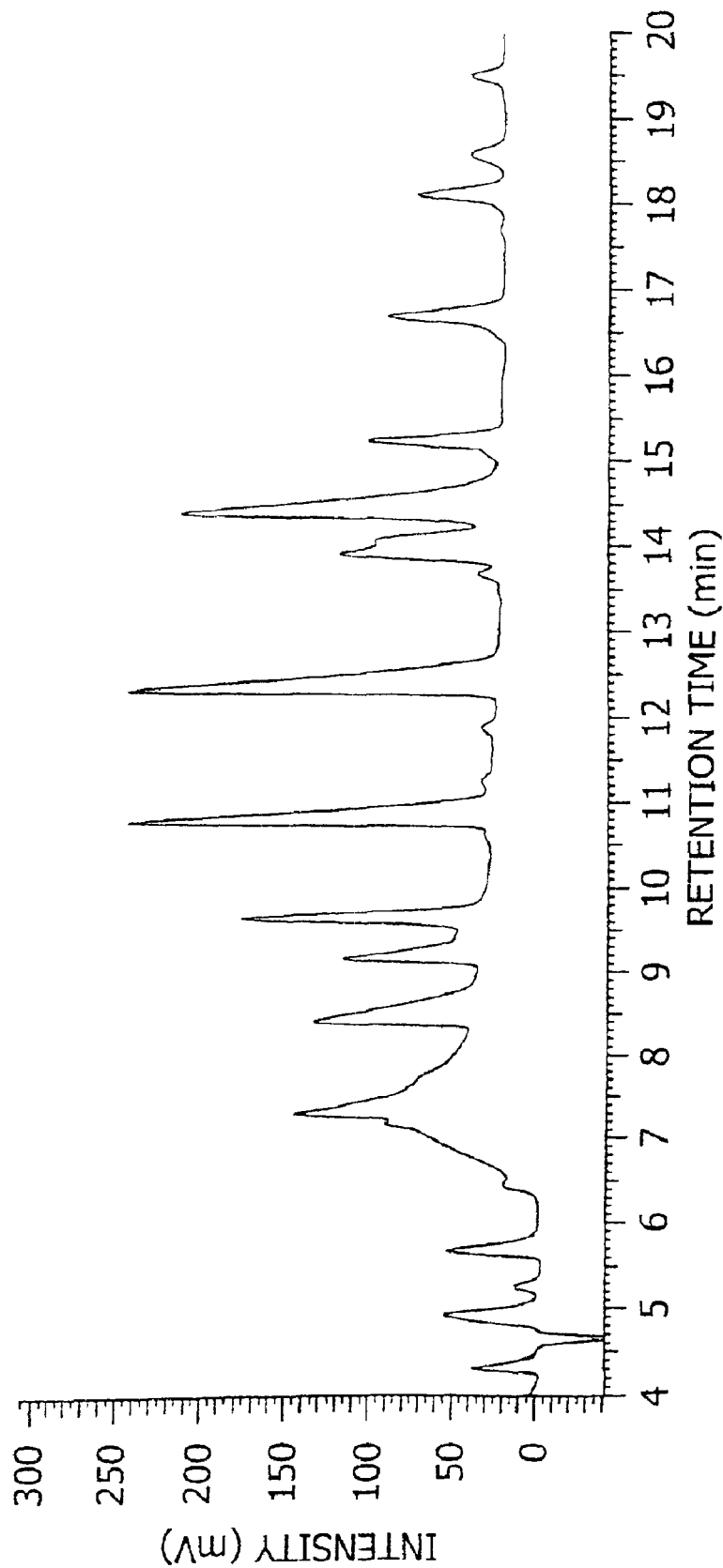

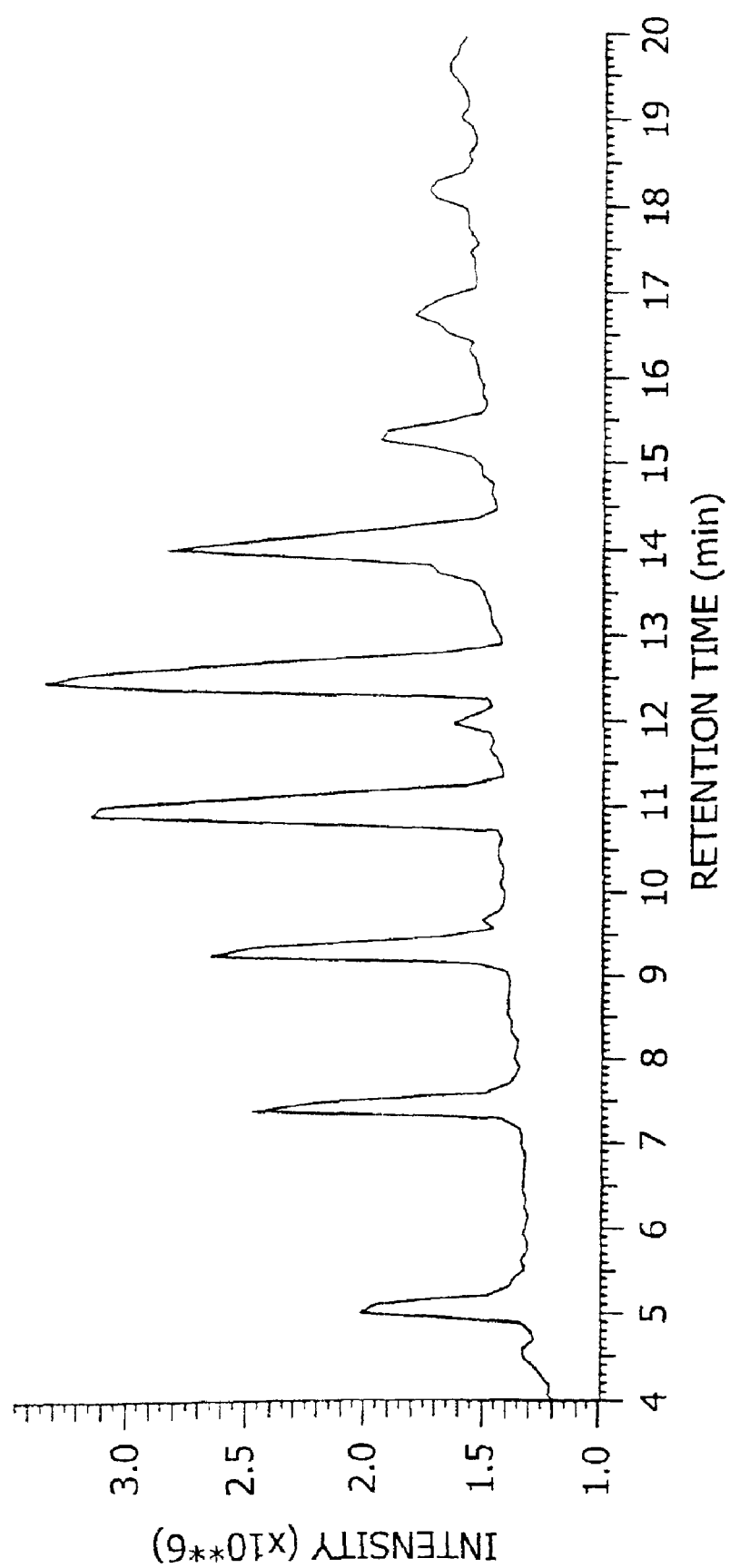
FIG. 15B CHROMATOGRAMS OF PERSULFONATED HMB-METHIONINE CO-OLIGOMERS POSITIVE ION TOTAL ION CHROMATOGRAM POSITIVE ION ESI SPECTRA OF (Met)$_6$ SULFONE PEAK ELUTING AT 11.09 min

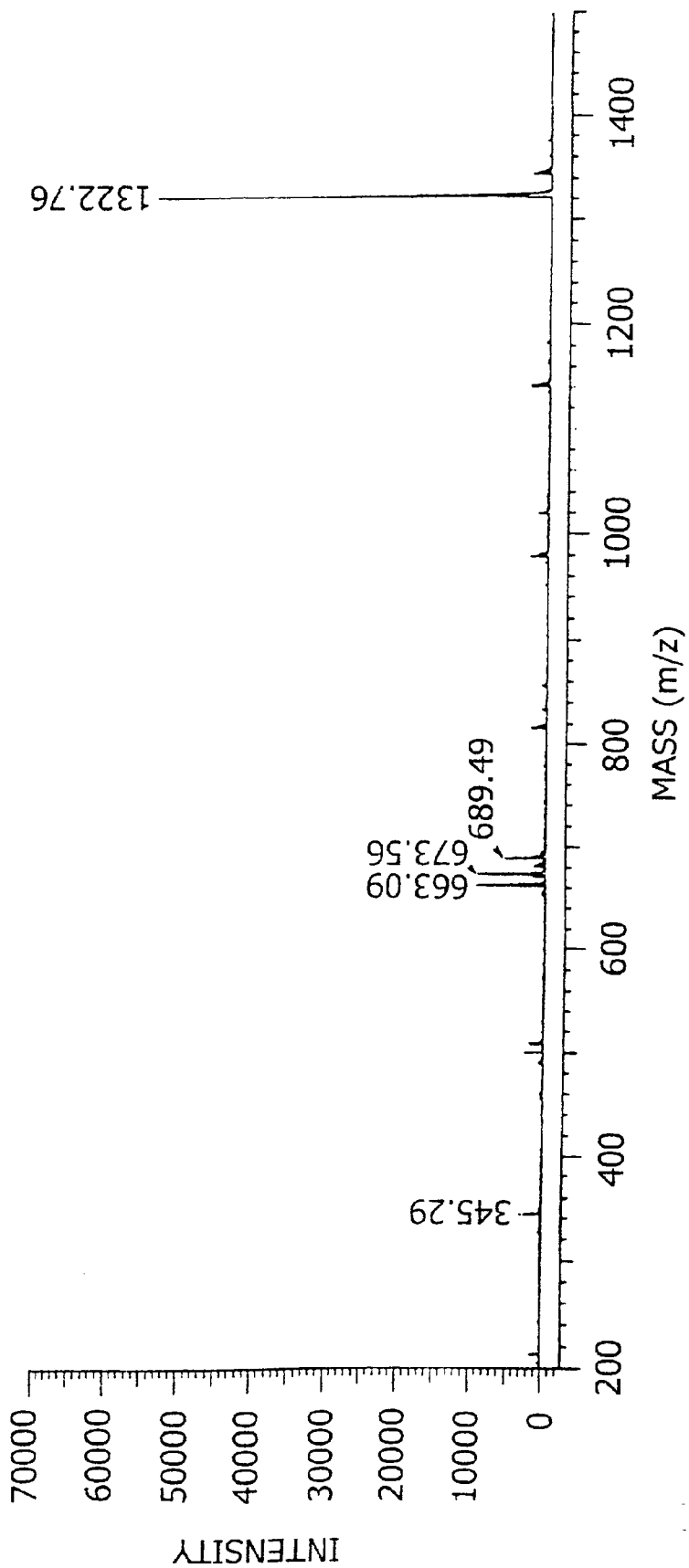
FIG. 20B Positive ion ESI spectra of (Met)$_8$ sulfone peak eluting at 14.26 min

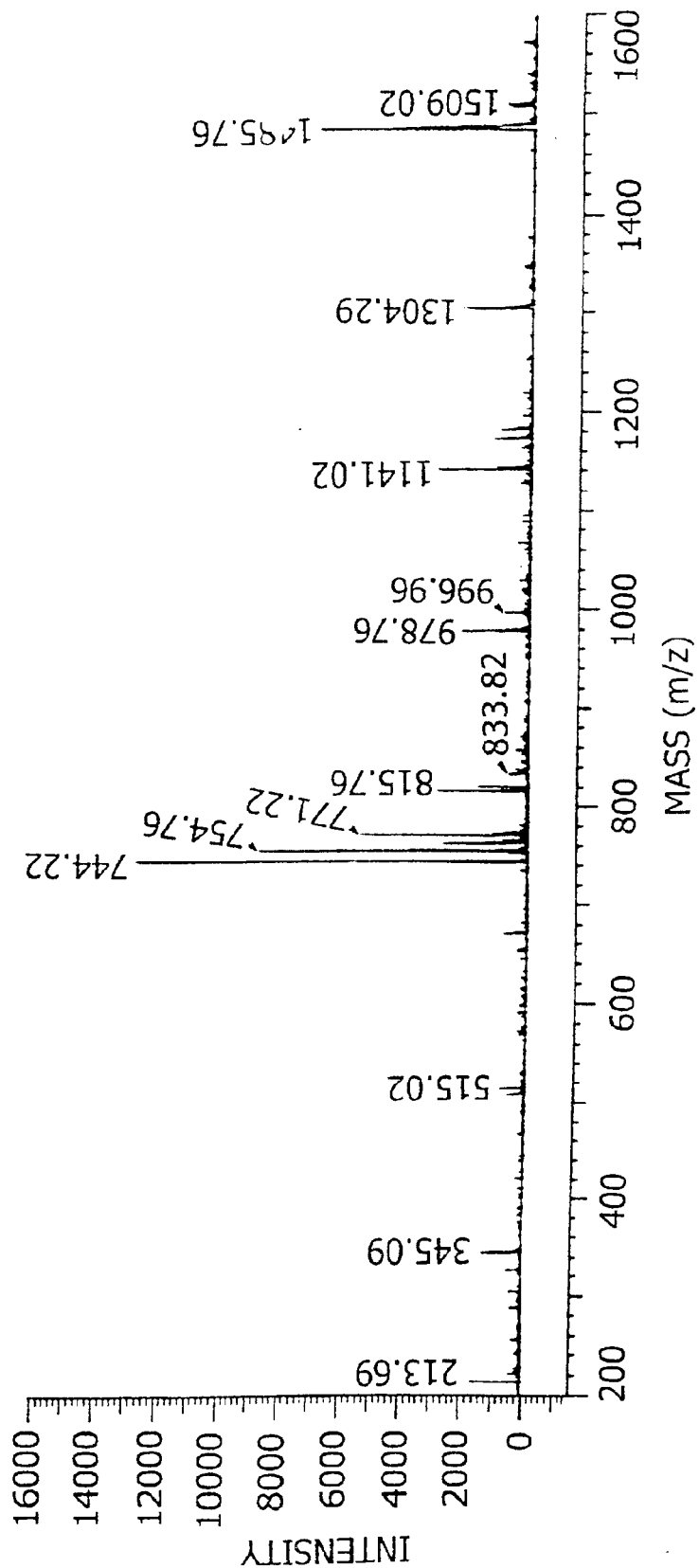
FIG. 20C POSITIVE ION ESI SPECTRA OF (Met)$_9$ SULFONE PEAK ELUTING AT 15.60 min. THE m/z 744 IS DOUBLY CHARGED (Met)$_9$

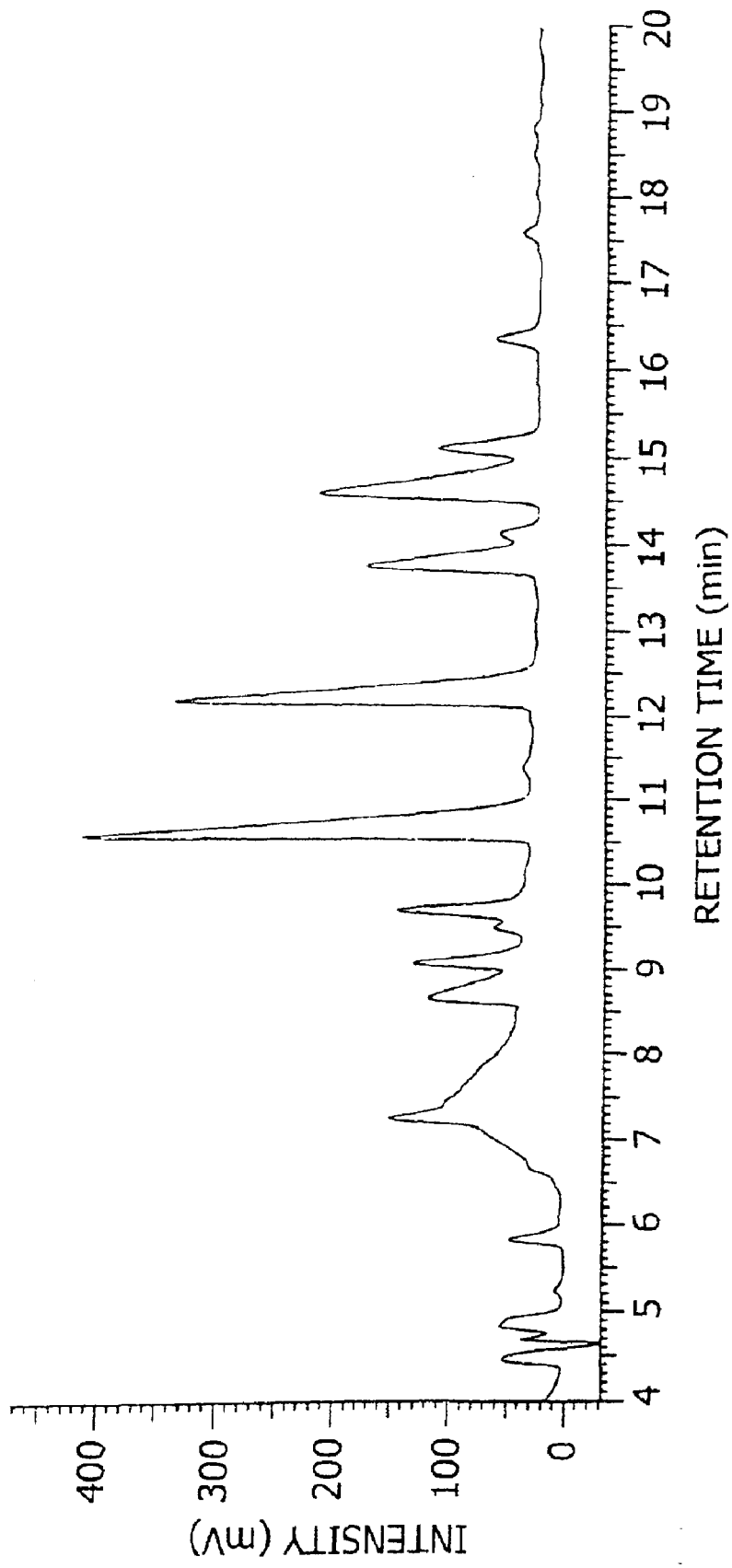

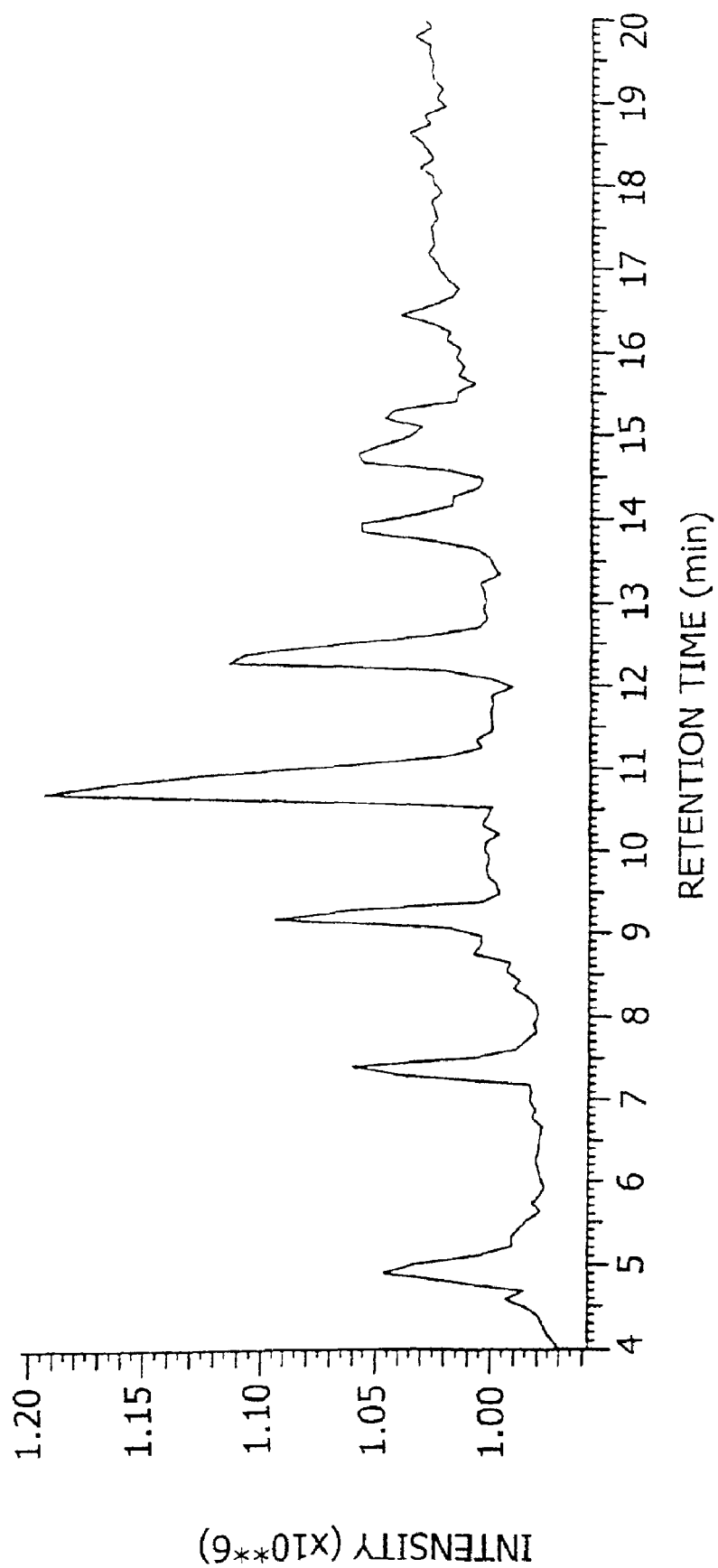

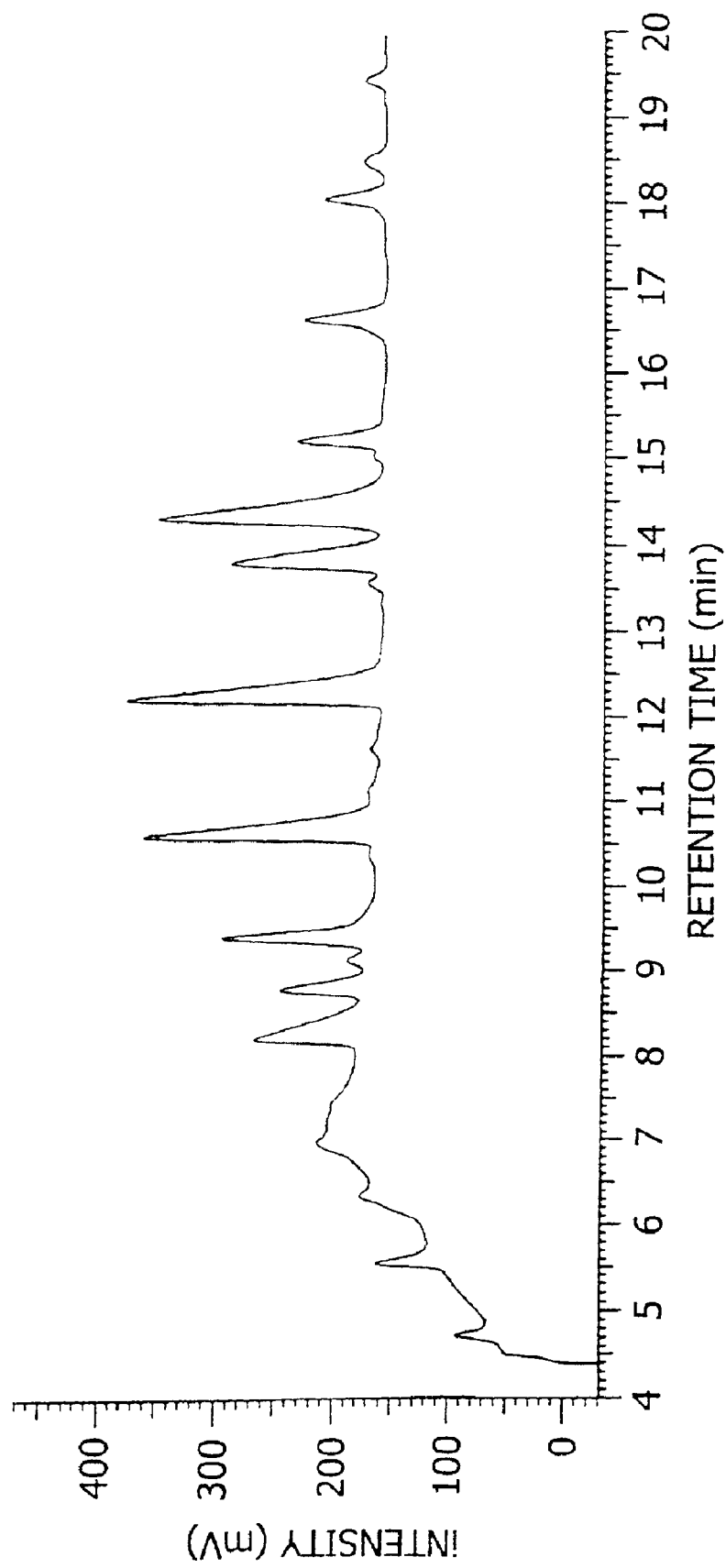
FIG. 22A CHROMATOGRAMS OF PERSULFONATED HMB-Met CO-OLIGOMERS UV ABSORPTION DETECTOR

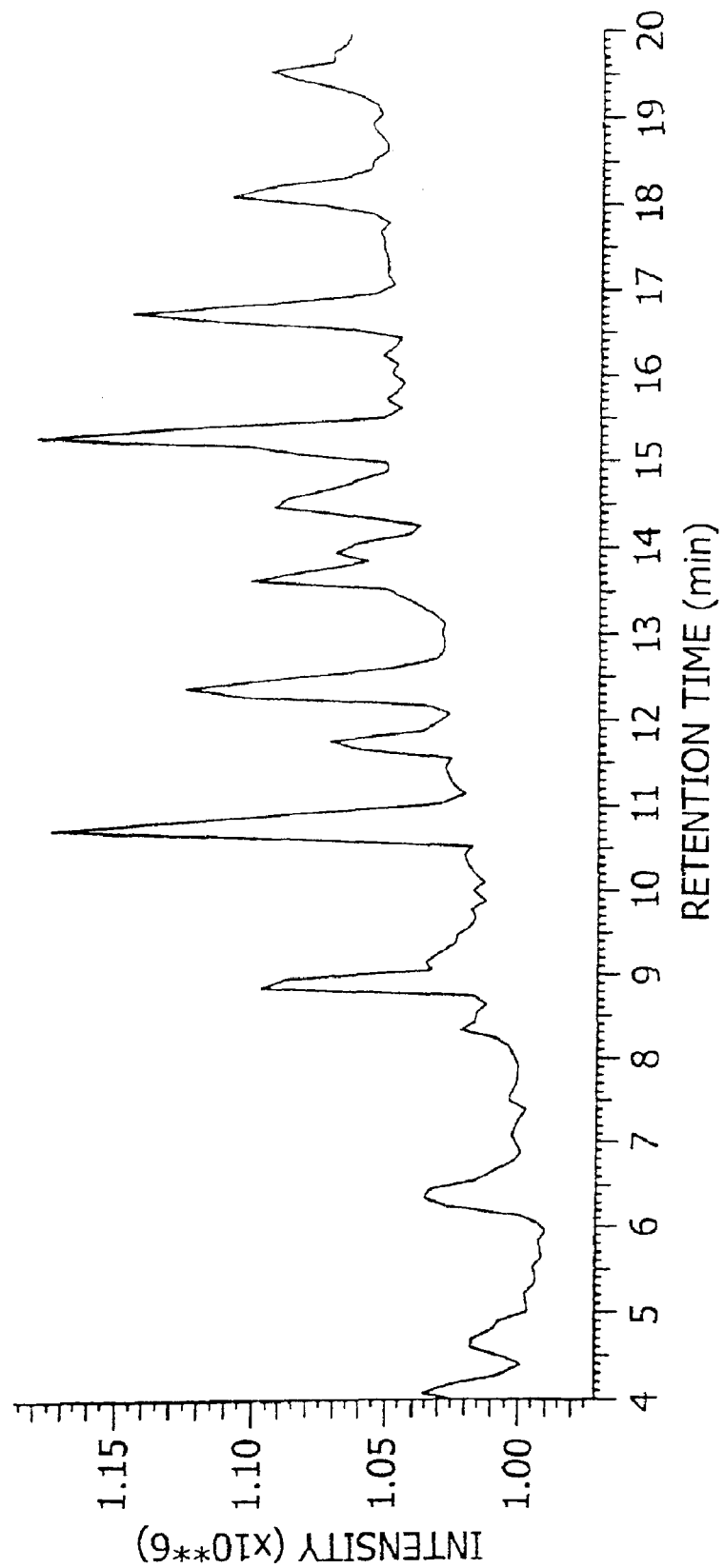

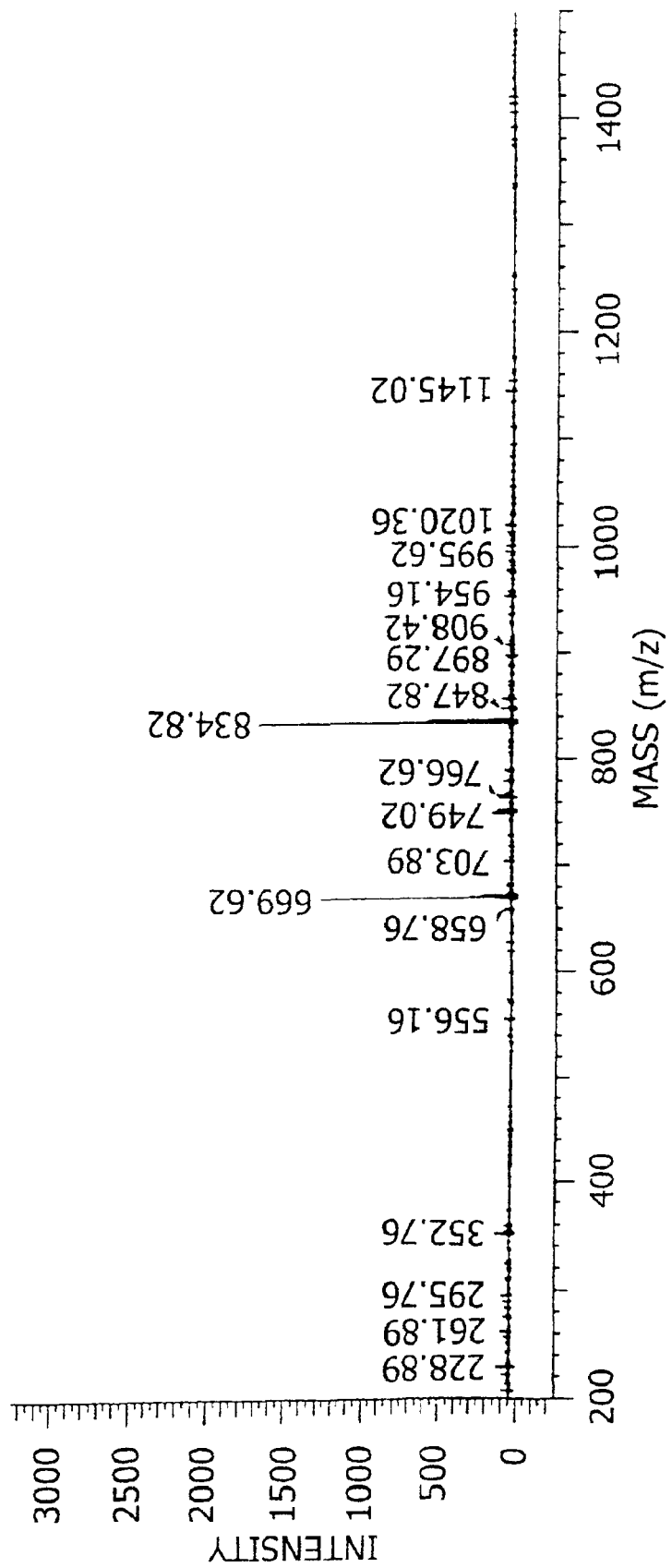
FIG. 23  NEGATIVE ION ESI SPECTRA OF HMB-(Met)$_5$ SULFONE PEAK ELUTING AT 11.57 MIN

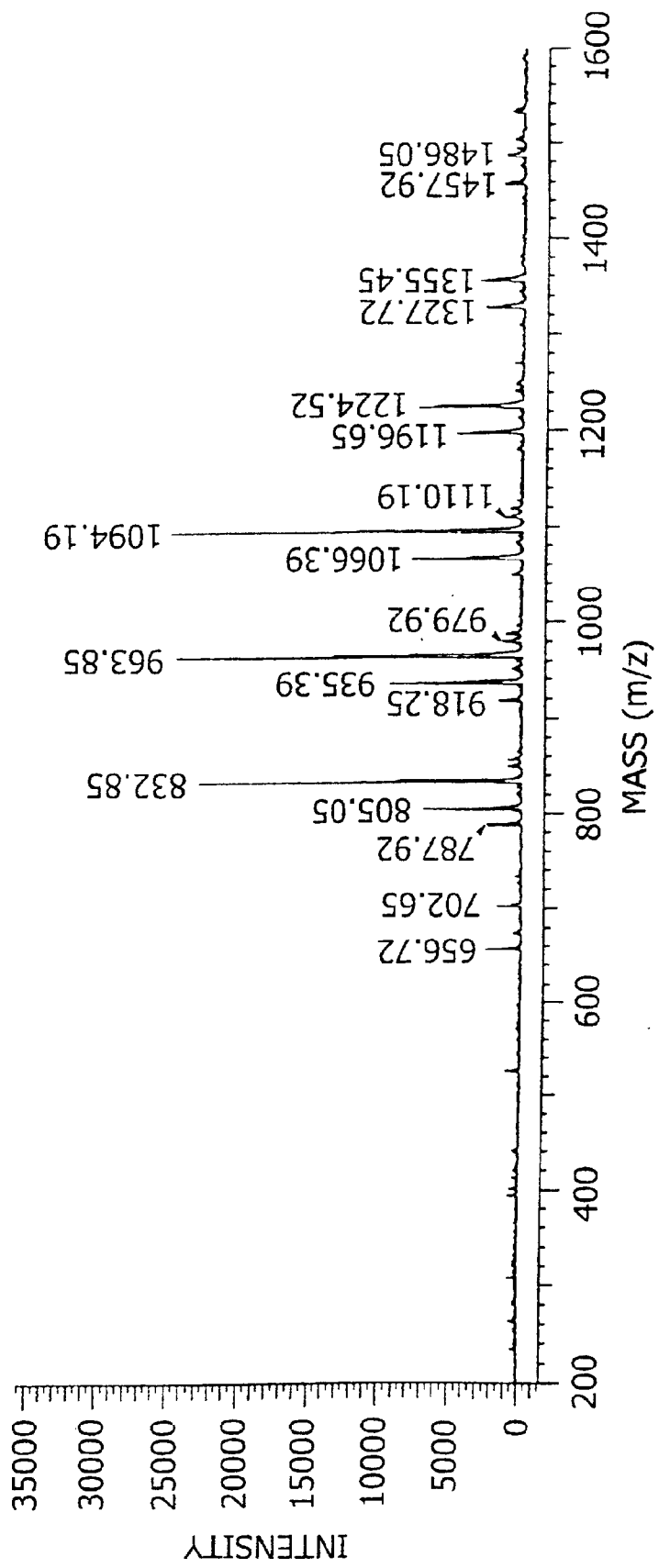
FIG. 28A POSITIVE AND NEGATIVE ION ESI-MS SPECTRA OF HMB-Met CO-OLIGOMER SYNTHESIS WITH HMB METHYL ESTER AND MetEE

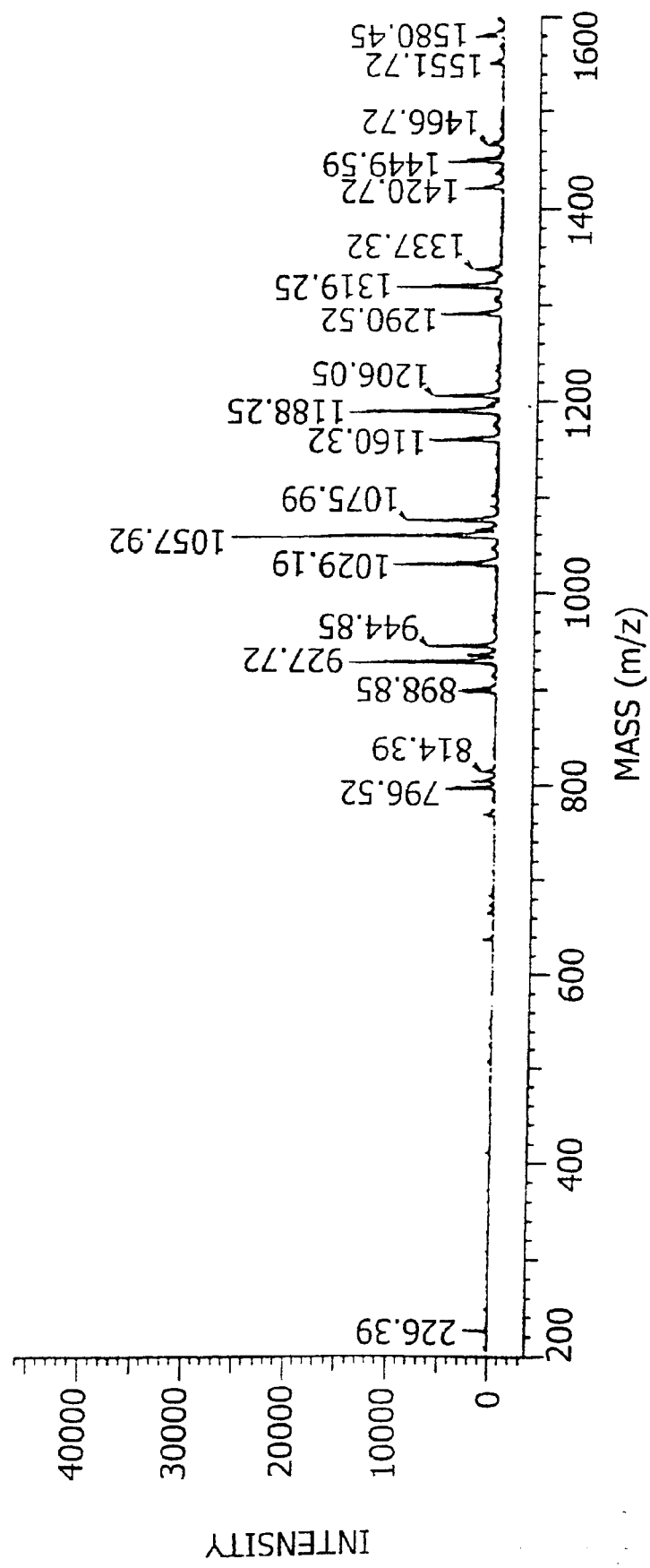
FIG. 28B POSITIVE AND NEGATIVE ESI-MS SPECTRA OF HMB-Met CO-OLIGOMER SYNTHESIS WITH HMB METHYL ESTER AND MetEE

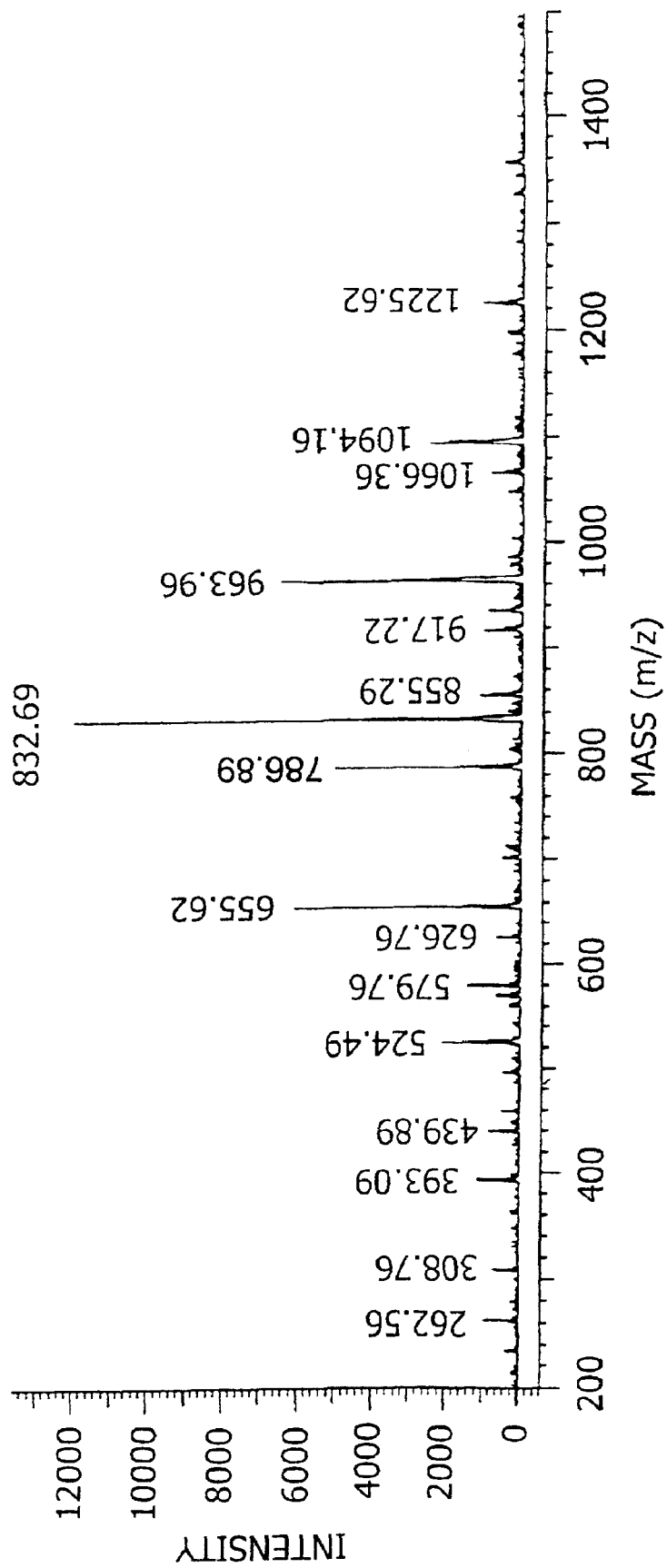
FIG. 29 PARENT ION SSI-MS SPECTRA OF HMB-MET CO-OLIGOMER SYNTHESIZED WITH HMB METHYL ESTER AND MetEE

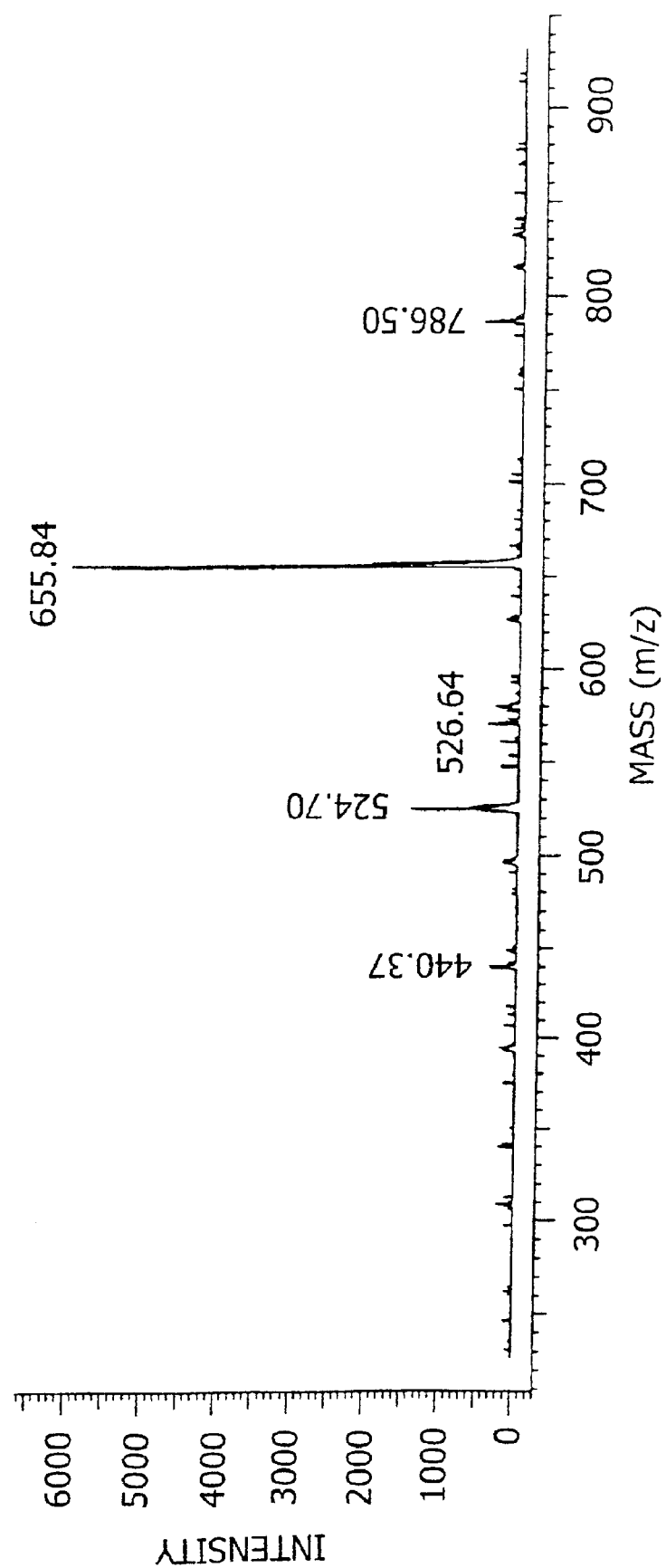
FIG. 30 DAUGHTER ION SPECTRUM OF (Met)$_6$-EE

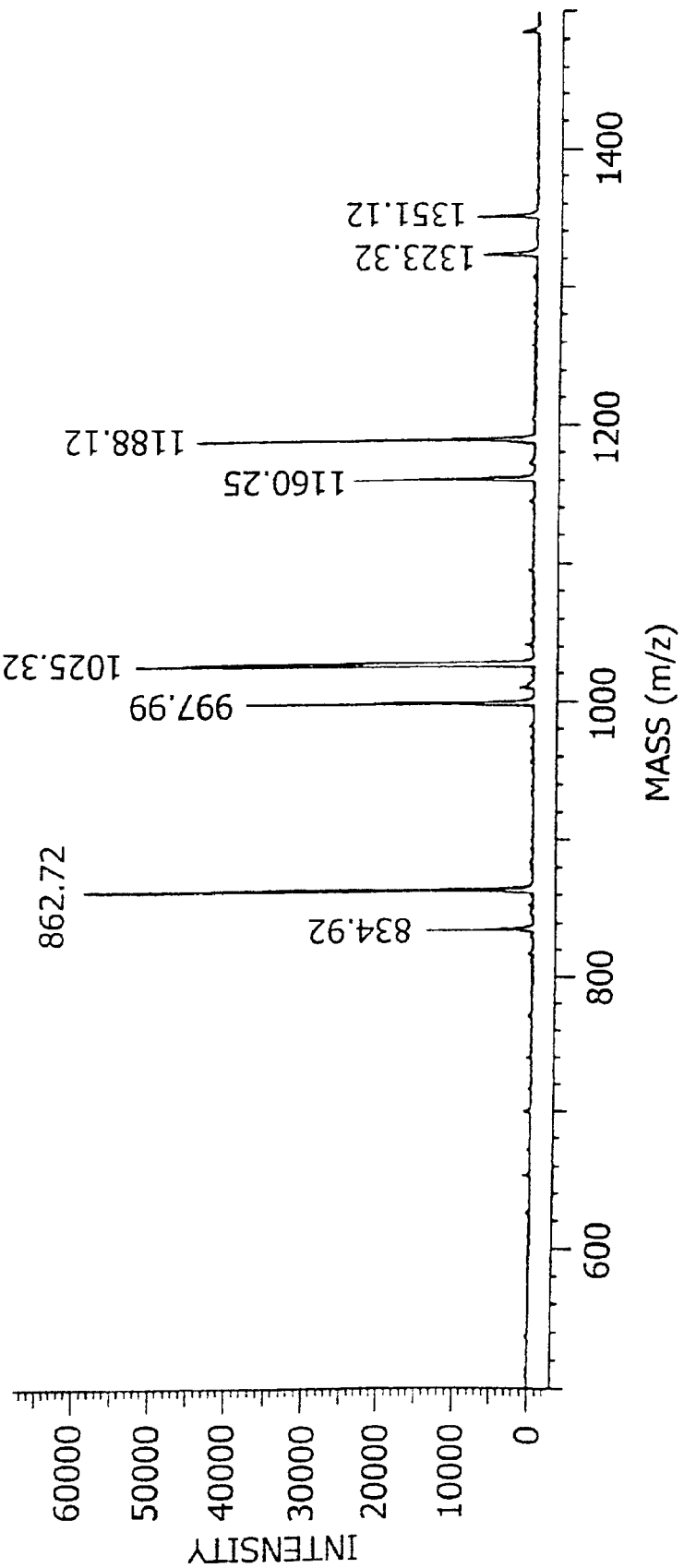
FIG. 31A POSITIVE ION ESI-MS SPECTRA OF TYROSINE $(Tyr)_n$ OLIGOMERS

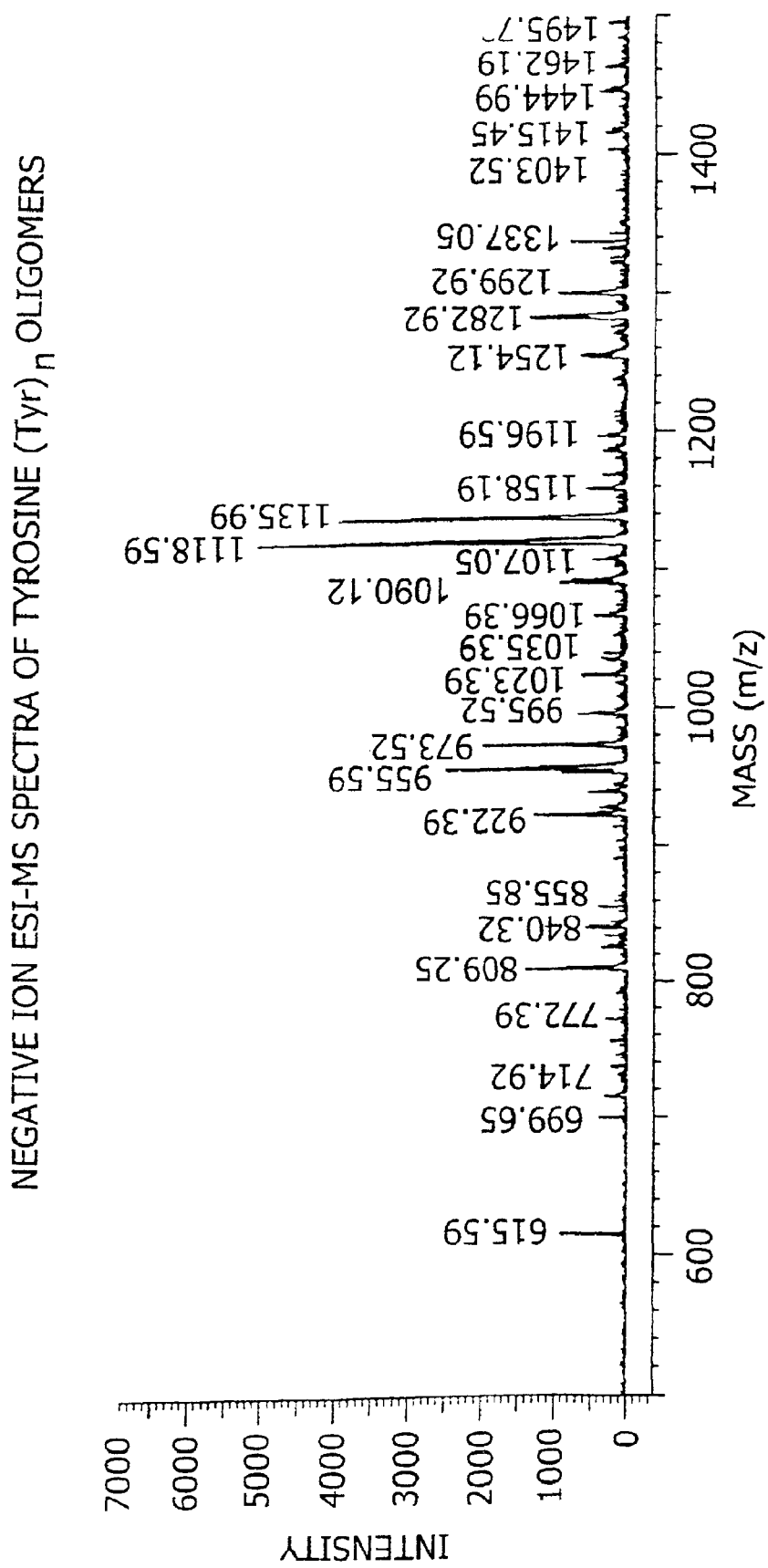
FIG. 31B   NEGATIVE ION ESI-MS SPECTRA OF TYROSINE $(Tyr)_n$ OLIGOMERS

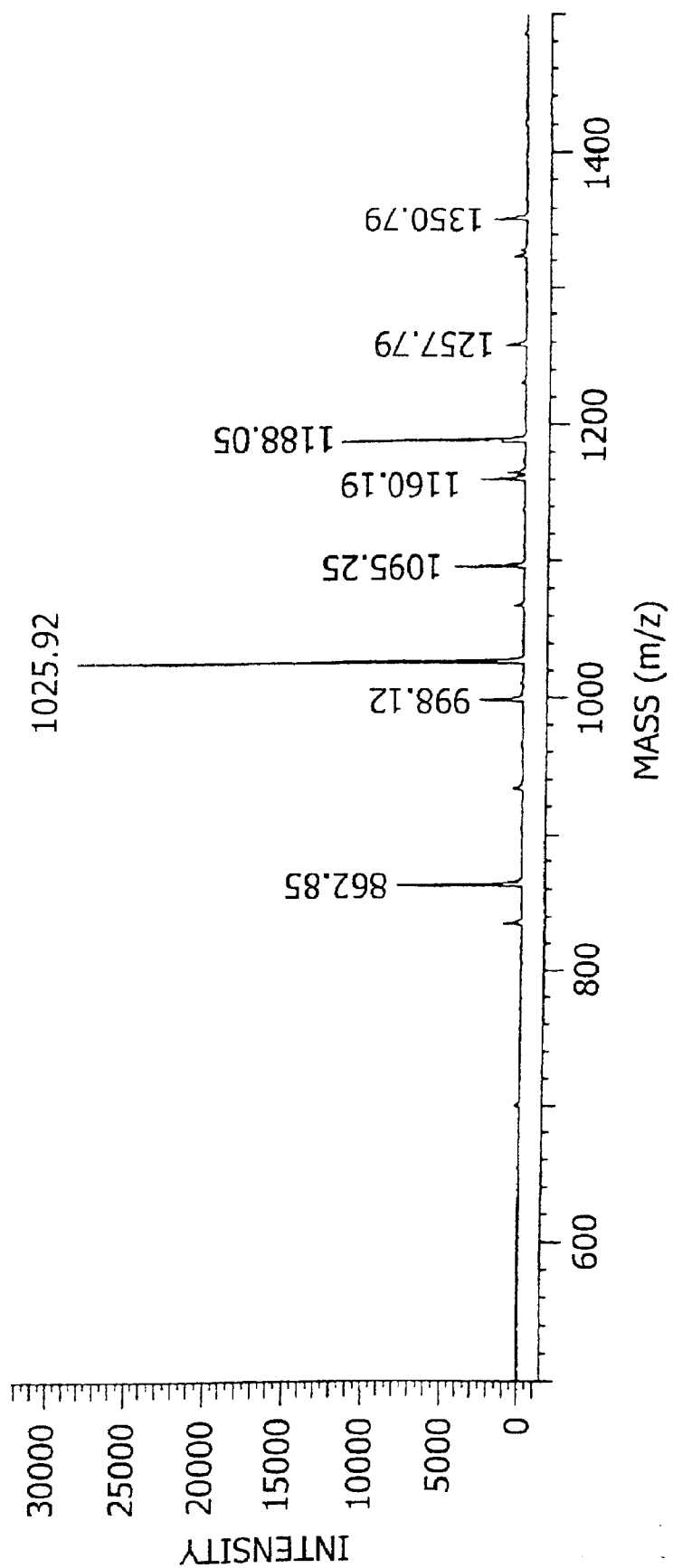
FIG. 32A  MHBA-TYROSINE CO-OLIGOMERS WITH POSITIVE ION SPECTRA

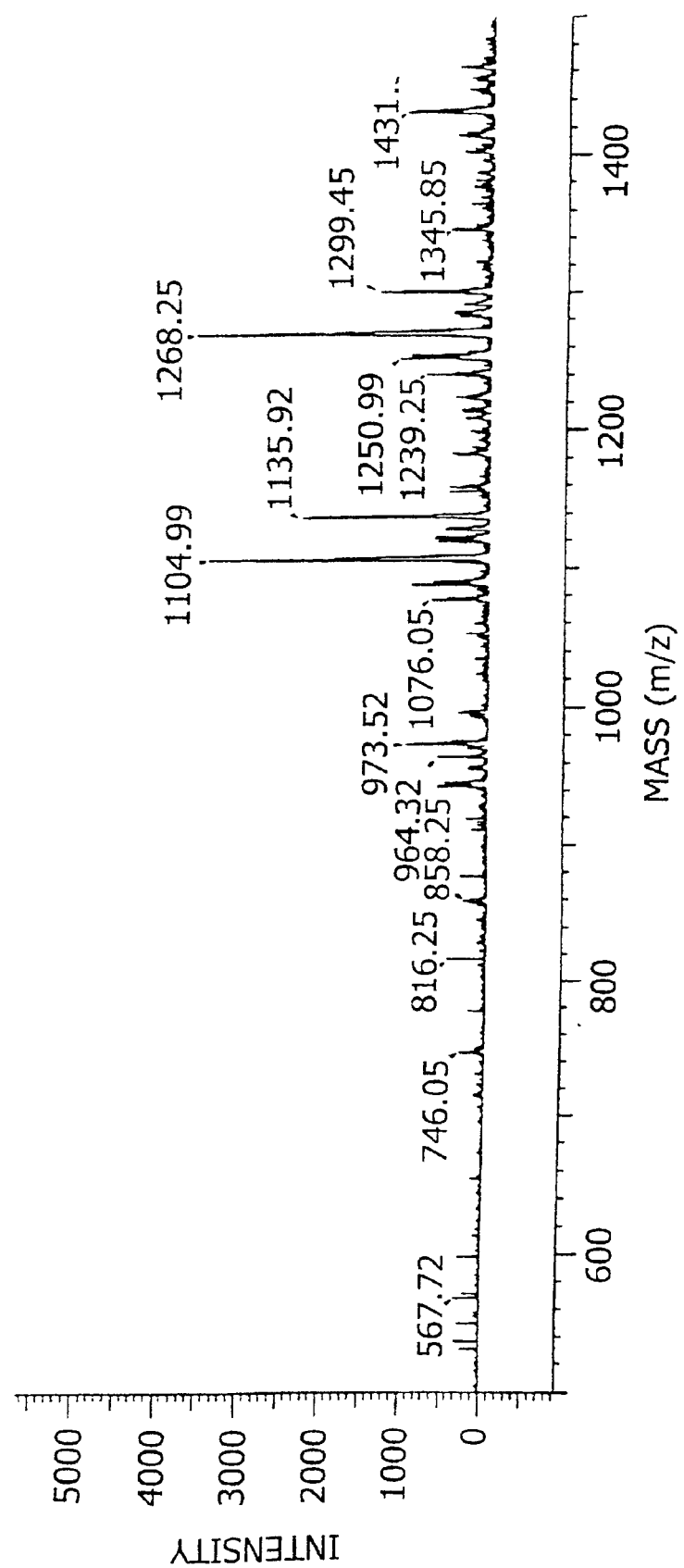
FIG. 32B  MHBA-TYROSINE CO-OLIGOMERS WITH NEGATIVE ION SPECTRA

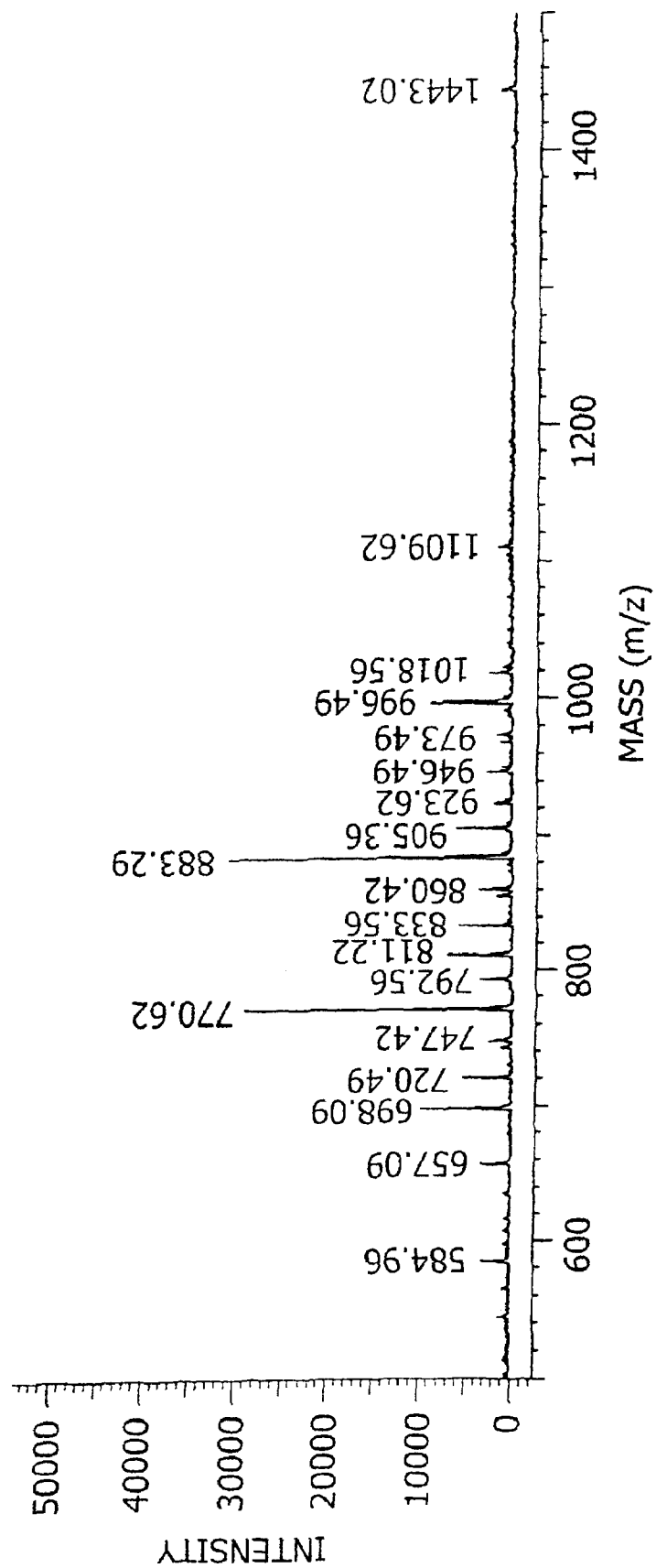
FIG. 33A  POSITIVE ION ESI-MS SPECTRA OF LEUCINE OLIGOMERS

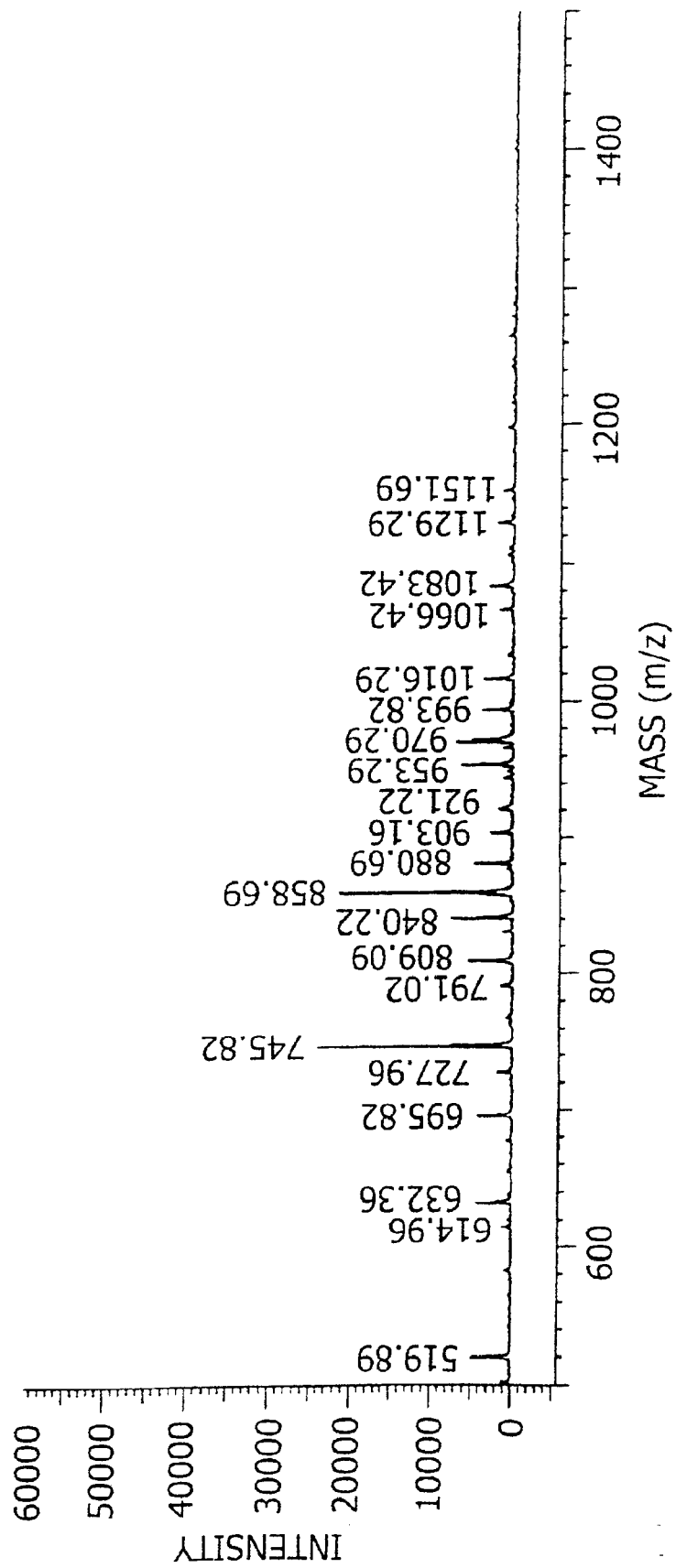
FIG. 33B  NEGATIVE ION ESI-MS SPECTRA OF LEUCINE OLIGOMERS

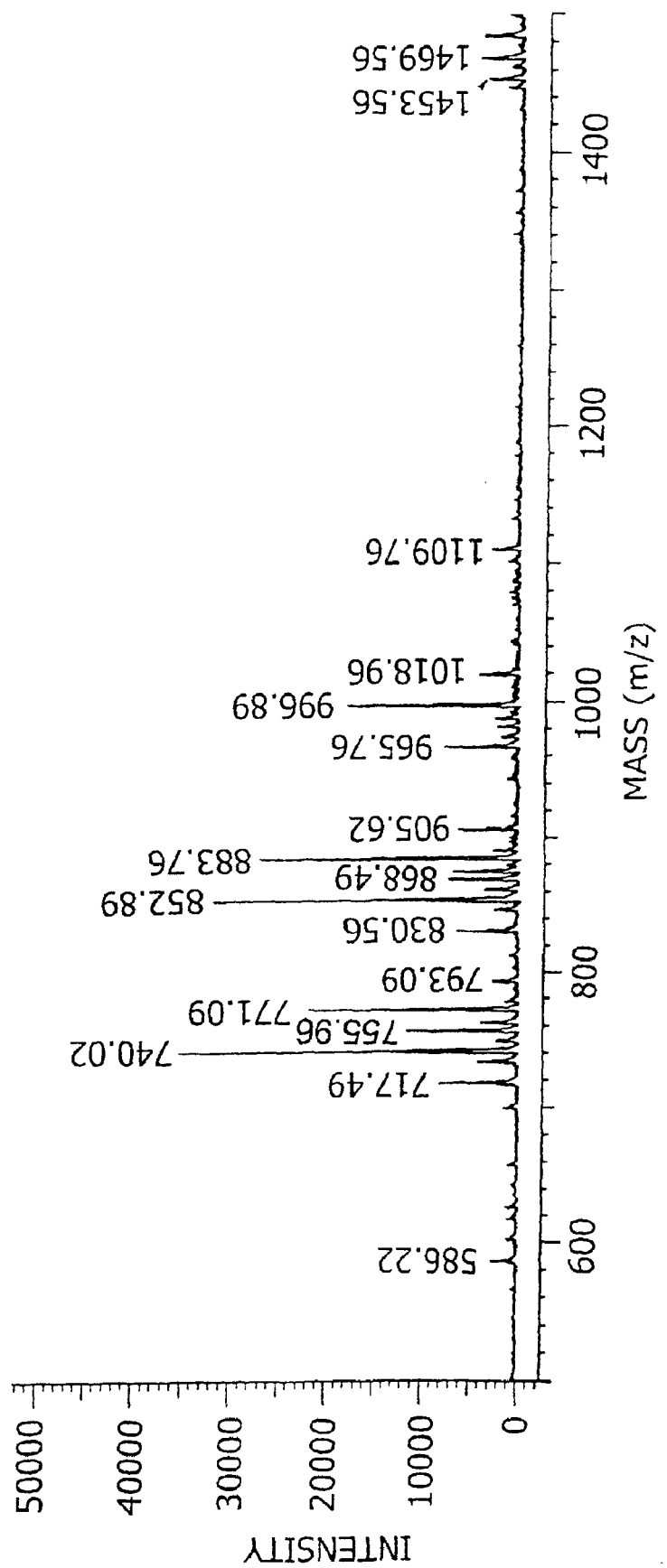
FIG. 34A POSITIVE ION ESI-MS SPECTRA OF HMB LEUCINE CO-OLIGOMERS

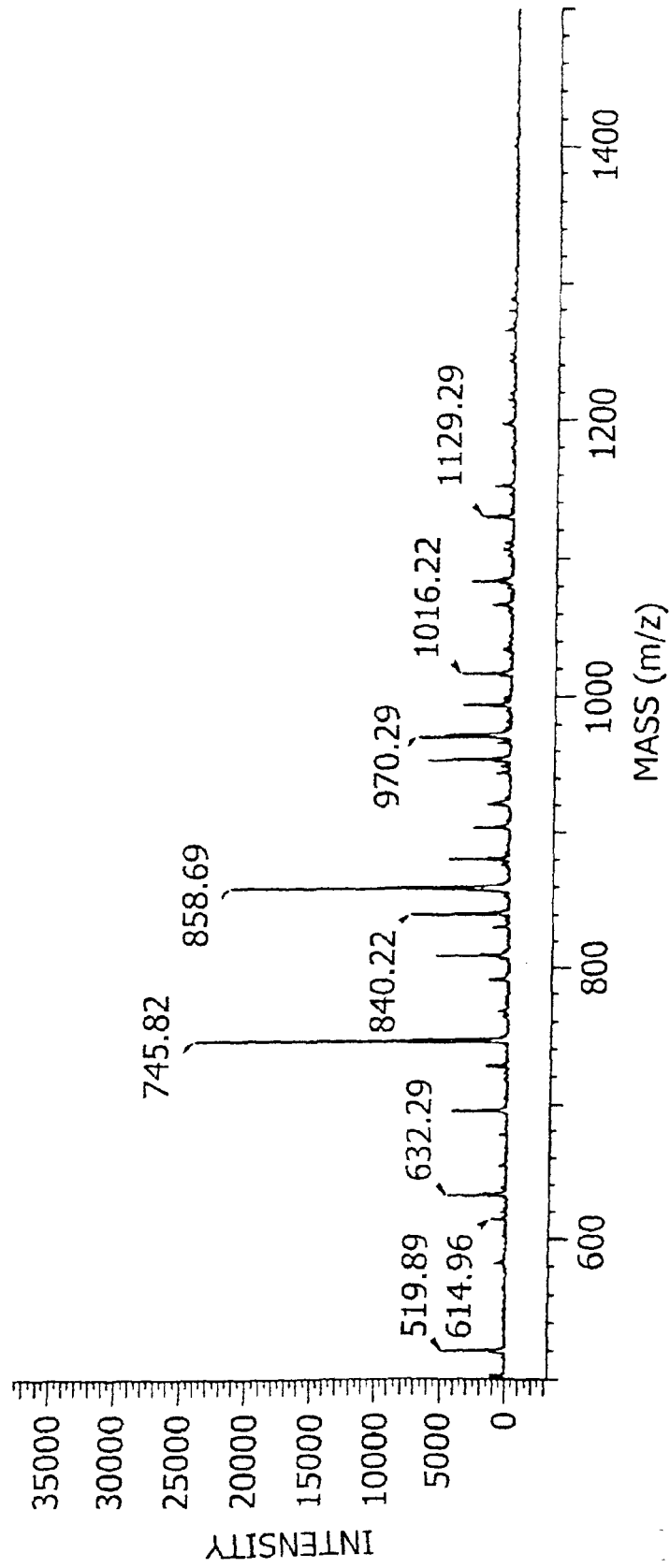
FIG. 34B  NEGATIVE ION ESI-MS SPECTRA OF HMB LEUCINE CO-OLIGOMERS

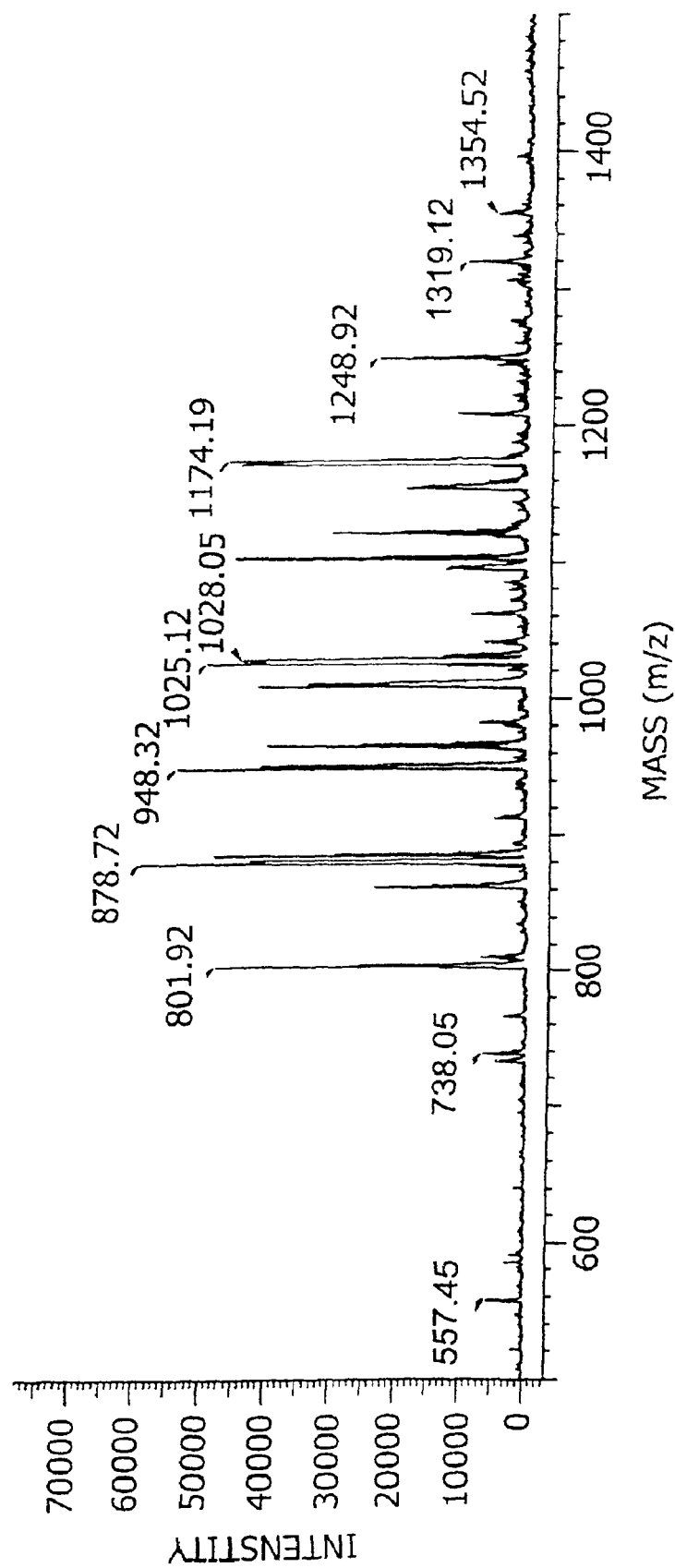
FIG. 35B NEGATIVE ION ESI-MS SPECTRA OF HMB-Phe CO-OLIGOMERS

THE EFFECTS OF AQUEOUS : NON AQUEOUS SOLVENT RATIO ON (Lys)$_n$ YIELD

YIELD vs. AQUEOUS : NON POLAR SOLVENT RATIO

FIG. 37 EFFECT OF VOLUMETRIC RATIO ON DEGREE OF (Lys)n OLIGOMERIZATION

EFFECT OF VOLUMETRIC RATIO OF AQUEOUS AND NONAQUEOUS SOLVENTS IN TWO PHASE REACTION SYSTEM

FIG. 41 DISTRIBUTION OF LYSINE OLIGOMERS FORMED IN REACTION MIXTURES WITH VARIED SUBSTRATE CONCENTRATIONS

EFFECT OF SUBSTRATE CONCENTRATION ON THE TWO PHASE SYSTEM

EFFECT OF INCUBATION PERIOD ON THE TOTAL OLIGOMERS YIELD
EFFECT OF INCUBATION PERIOD ON OLIGOMER YIELD

FIG. 44 EFFECT OF AQUEOUS TO NON-AQUEOUS SOLVENT PHASE RATIO ON OLIGOMERS YIELD
EFFECT OF PHASE RATIO (AQUEOUS TO NON-AQUEOUS)

FIG. 45 DISTRIBUTION OF (Lyn) OLIGOMERS FORMED IN REACTION MIXTURES WITH VARIED AQUEOUS TO NON-AQUEOUS SOLVENT RATIOS.

EFFECT OF VOLUMETRIC PHASE RATIO IN BIPHASIC SYSTEM

EFFECT OF INCUBATION PERIOD ON THE TOTAL LYSINE OLIGOMERS YIELD

TIME-SERIES YIELD OF LYSINE OLIGOMERIZATION IN TRI-PHASIC SYSTEM

FIG. 50 DISTRIBUTION OF (Lyn) OLIGOMERS FORMED AFTER 24 HOUR INCUBATION PERIOD
THREE PHASE SYSTEM: OLIGOMERIZATION PROFILE

ENANTIOSELECTIVE OLIGOMERIZATION OF α-HYDROXY CARBOXYLIC ACIDS AND α-AMINO ACIDS

CROSS-REFERENCE TO RELATED APPLICATIONS

This application claims priority from U.S. provisional application Ser. No. 60/288,196, filed May 2, 2001, and as a continuation-in-part of U.S. patent application Ser. No. 09/699,946, filed Oct. 30, 2000 now U.S. Pat. No. 6,605,590, which claims priority from U.S. Provisional Application Ser. No. 60/162,725, filed Oct. 29, 1999 (now abandoned). The entire texts of U.S. Provisional Application Ser. No. 60/288,196, U.S. patent application Ser. No. 09/699,946 and U.S. Provisional Application Ser. No. 60/288,196 are hereby incorporated herein by reference.

BACKGROUND OF THE INVENTION

The present invention relates to a process for the enantioselective preparation of oligomers consisting of α-amino acid isomers and co-oligomers consisting of α-hydroxy carboxylic acid isomers and α-amino acid isomers. The present invention also relates to compositions containing such oligomers and co-oligomers and methods of use thereof.

In an effort to improve nutrition, the diets of ruminant animals have been supplemented with proteins and naturally occurring α-amino acids. Unfortunately, these proteins and α-amino acids can be subjected to extensive degradation in the rumen by ruminal microorganisms, thereby rendering the protein or amino acid unavailable to the animal for absorption. This is not a very efficient utilization of the feed, which is especially problematic in animals having increased nutritional requirements such as lactating dairy cows and fast growing animals such as beef cattle.

One approach to solving this problem has been to modify or protect the dietary protein or amino acid by a variety of chemical and physical methods so that it escapes degradation in the rumen. For example, heating soybean meal has shown some promise in producing protected proteins. However, the results were highly variable. Underheating the protein resulted in no protection while overheating the protein resulted in the degradation of important essential amino acids. See, for example, Plegge, S. D., Berger, L. L. and Fahey Jr. G. C. 1982. Effect of Roasting on Utilization of Soybean Meal by Ruminants. *J. Anim. Sci.* 55:395 and Faldet, M. A., Son, Y. S. and Satter, L. D. 1992. Chemical, in vitro and in vivo evaluation of soybean heat-treated by various processing methods. *J. Dairy Sci.* 75:789. Similarly, physical coating of proteins with materials such as fats and calcium soaps of fats has been met with mixed success.

Therefore, there is a need to somehow protect the protein from degradation in the rumen in order to make it available to the animal in the intestine where it can be properly absorbed. This would allow the animal to get increased nutritional benefit from the feed. Increasing the nutritional benefit of the feed can reduce the amount of feed required by the animals.

Dietary supplements such as proteins, naturally occurring α-amino acids, vitamins, minerals, and other nutrients are also used in aquaculture, (i.e., the cultivation of aquatic animals such as fish and crustaceans). Many of such supplements are difficult to provide, however, due to being soluble in water which causes the supplements to dissolve before they can be ingested. Dietary supplements for use in aquaculture therefore are preferably in an insoluble form in order to be ingested.

The role played by short chain peptides and their derivatives in the areas of nutrition science, flavor chemistry, and pharmacology has primed the advances in peptide chemistry. The inherent advantages of enzymatic peptide synthesis has led to its evolution as an alternative to chemical coupling methods (Fruton, J. S., 1992, Adv. Enzymology, 53, 239–306). The thiol-protease papain is reported to be the most efficient catalyst for aqueous phase synthesis of homooligomers of hydrophobic amino acids like leucine, methionine, phenylalanine, and tyrosine (A. Ferjancic, A. Puigserver and H.Gaertner, *Biotech. Lett*, 13(3) (1991) 161–166). The equilibria of such reactions is tilted in favor of synthesis by the precipitation of hydrophobic oligomers. However, the difficulty involved in the analysis of higher order, water insoluble oligomers, presents a unique challenge to biochromatography.

SUMMARY OF THE INVENTION

Among the objects of the present invention, therefore, is the provision of an oligomer which is protected from degradation in the rumen of a ruminant, the provision of such an oligomer which provides nutritional or pharmacological benefit to the animal, and the provision of a process for the preparation of such oligomers.

A further object of the present invention is the provision of a co-oligomer and oligomer that provides nutritional or pharmacological benefit to animals, and the provision of a process for the preparation of such co-oligomers and oligomers.

A further object of the invention is the provision of a co-oligomeric or oligomeric coating for vitamins, minerals, or nutrients.

Another object of the present invention is the provision of a method to purify enantiomeric mixtures of α-hydroxy carboxylic acids, α-amino acids, or combinations thereof.

Briefly, therefore, the present invention is directed to a process for the preparation of an oligomer consisting of α-amino acid isomers. The process comprises forming a reaction mixture containing (i) an enzyme and (ii) an an enantiomeric mixture of α-amino acid, or derivative thereof. An oligomer is formed that incorporates one enantiomer of the enantiomeric mixture of the α-amino acid or derivative thereof in preference to the other enantiomer.

The present invention is further directed to a composition comprising a residue of an α-hydroxy carboxylic acid bonded to a peptide by an amide or an ester linkage, said peptide comprising two or more α-amino acid residues, each of said α-amino acids being independently selected from the group consisting of α-amino acids. Preferably, more than 50% of the α-amino acid residues in the peptide are of identical chirality.

The present invention is further directed to an oligomer of the formula CA-(AA)$_n$- wherein CA is the residue of an α-hydroxy carboxylic acid, each AA is the residue of an α-amino acid or derivative thereof wherein greater than one-half of the AA residues are derived from the group consisting of α-amino acids or derivatives thereof having the same chiral configuration, and n is at least 2.

The present invention is also directed to a process for providing an animal with a food ration. The process comprises providing an oligomer or a co-oligomer prepared from a mixture containing an enzyme, an α-amino acid, and optionally, an α-hydroxy carboxylic acid or derivative thereof. The feed ration is administered to the animal by oral administration, eye spray, placement in ear, placement in nasal cavity, and bucchal administration, sublingual administration, rectal administration or injection.

The present invention is further directed to an orally administered dietary supplement comprising a vitamin, mineral, or nutrient that is coated with an oligomeric coating. The coating comprises a residue of an α-hydroxy carboxylic acid bonded to a peptide by an amide linkage. The peptide comprises two or more independent α-amino acids independently selected from the group consisting of α-amino acids.

The present invention is further directed to a process for providing an animal with a dietary supplement comprising a vitamin, mineral, or nutrient. The process comprises coating the vitamin, mineral or nutrient with a composition to form a dietary supplement and administering the dietary supplement to the animal. The composition comprises a residue of an α-hydroxy carboxylic acid bonded to a peptide by an amide linkage and the peptide comprises two or more independent α-amino acids independently selected from the group consisting of α-amino acids.

The present invention is further directed to a process for purifying an enantiomeric mixture of α-amino acid or derivative thereof. The process comprises forming a reaction mixture comprising (i) an enzyme, (ii) an enantiomeric mixture of α-amino acid or a derivative thereof, and (iii) an α-hydroxy carboxylic acid or a derivative thereof. A peptide reaction product is formed from the reaction mixture comprising (i) an oligomer or co-oligomer from the combination which incorporates one of the members of the enantiomeric mixture of α-amino acid or derivative thereof in preference to a second enantiomer of the enantiomeric mixture, and (ii) unreacted second enantiomer. The oligomer or co-oligomer and unreacted second enantiomer are then separated from the reaction product and each other.

The present invention is also directed to a process for purifying an α-hydroxy carboxylic acid enantiomer or derivative thereof in an enantiomeric mixture. The process comprises forming a reaction mixture comprising (i)an enzyme, (ii) an enantiomeric mixture of an α-hydroxy carboxylic acid and (iii) an α-amino acid or a derivative thereof. A reaction product is formed from the reaction mixture comprising (i) a co-oligomer which preferentially incorporates a first enantiomer over a second enantiomer of the enantiomeric mixture, and (ii) unreacted second enantiomer. The co-oligomer and unreacted second enantiomer are then separated from the reaction product and each other.

Other objects and features of this invention will be in part apparent and in part pointed out hereinafter.

BRIEF DESCRIPTION OF THE DRAWINGS

FIG. 14B is a positive ion total ion chromatogram of persulfonated methionine oligomers.

FIG. 15A is a chromatogram of persulfonated HMB-methionine co-oligomers using a UV absorption detector.

FIG. 15B is a positive ion total ion chromatogram of persulfonated HMB-methionine co-oligomers.

FIG. 20B is a positive ion ESI spectra of $(Met)_8$ sulfone peak eluting at 14.26 minutes.

FIG. 20C is a positive ion ESI spectra of $(Met)_9$ sulfone peak eluting at 15.60 minutes.

FIG. 21A is a chromatogram of persulfonated methionine oligomers using a UV absorption detector.

FIG. 21B is a total ion chromatogram ESI-negative ion of persulfonated methionine oligomers.

FIG. 22A is a chromatogram of persulfonated HMB-methionine co-oligomers using a UV absorption detector.

FIG. 22B is a total ion chromatogram ESI-negative ion of persulfonated HMB-methionine co-oligomers.

FIG. 23 is a negative ion ESI spectra of HMB-$(Met)_5$ sulfone peak eluting at 11.57 minutes.

FIG. 28A is a positive ion ESI-MS spectra of HMB-methionine co-oligomers synthesized with HMB methyl ester and methionine ethyl ester.

FIG. 28B is a negative ion ESI-MS spectra HMB-methionine co-oligomers synthesized with HMB methyl ester and methionine ethyl ester.

FIG. 29 is a parent ion SSI-MS spectra HMB-methionine co-oligomers synthesized with HMB methyl ester and methionine ethyl ester.

FIG. 30 is a daughter ion spectrum of (Met)$_6$-ethyl ester.

FIG. 31A is a positive ion ESI-MS spectra of tyrosine (Tyr)n oligomers wherein n is the number of tyrosine residues in the oligomers.

FIG. 31B is a negative ion ESI-MS spectra of tyrosine (Tyr)n oligomers wherein n is the number of tyrosine residues in the oligomers.

FIG. 32A is a positive ion spectra of HMB-tyrosine co-oligomers.

FIG. 32B is a negative ion spectra of HMB-tyrosine co-oligomers.

FIG. 33A is a positive ion ESI-MS spectra of leucine oligomers.

FIG. 33B is a negative ion ESI-MS spectra of leucine oligomers.

FIG. 34A is a positive ion ESI-MS spectra of HMB-leucine co-oligomers.

FIG. 34B is a negative ion ESI-MS spectra of HMB-leucine co-oligomers.

FIG. 35B is a negative ion ESI-MS spectra of HMB-phenylanaline co-oligomers.

DETAILED DESCRIPTION OF THE PREFERRED EMBODIMENTS

Figure 1:
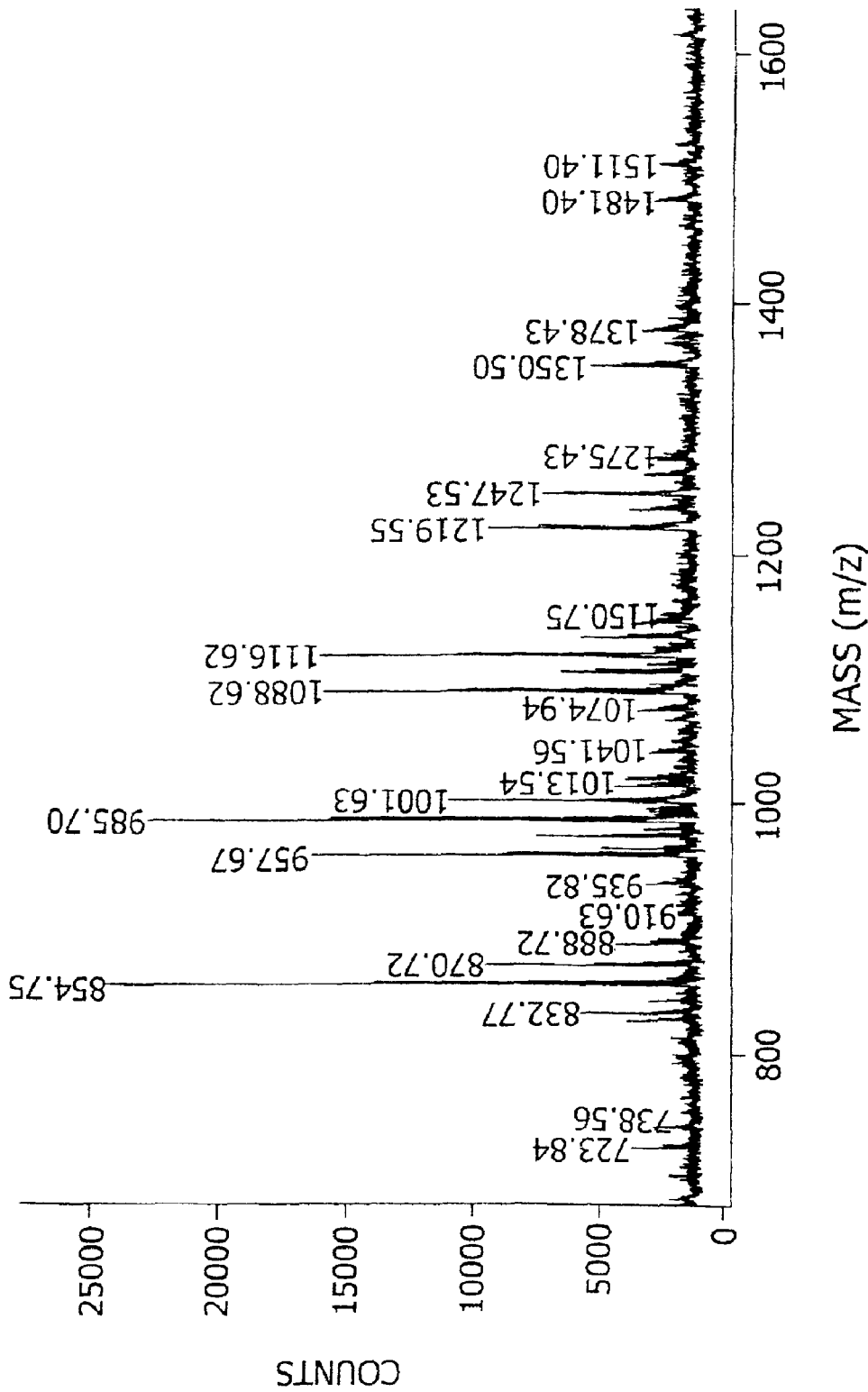
FIG. 1 is a MALDI-TOF graph of methionine oligomers and co-oligomers from a papain catalyzed synthesis.

In accordance with the present invention, it has been discovered that oligomers and co-oligomers of α-hydroxy carboxylic acids and α-amino acids may be prepared in an enzymatically catalyzed reaction.

The α-hydroxy carboxylic acid/α-amino acid oligomers enzymatically synthesized by the process of the present invention may possess altered properties from those of the α-amino acid monomers. For example, it has been suggested that the α-hydroxy carboxylic acid/α-amino acid oligomers, unlike proteins, peptides, or amino acid monomers, are not recognized in the rumen by ruminal microorganisms. As a result, the ruminal microorganisms do not break down the oligomers and the oligomers are available for absorption by the ruminant.

Further, the solubility properties of many of the α-hydroxy carboxylic acid/α-amino acid oligomers of the present invention are also different from their monomeric counterpart. Thus, while many α-amino acid monomers, such as methionine, are soluble in water, the α-hydroxy carboxylic acid/α-amino acid oligomers and α-amino acid oligomers formed from methionine monomers are insoluble.

This alteration advantageously permits the oligomers to be introduced in aqueous environments without being dissolved in the solution.

In general, the oligomers of the present invention comprise the residue of an α-hydroxy carboxylic acid bonded to the residue of an α-amino acid by an amide or an ester linkage. Thus, the oligomers correspond to the general formula CA-(AA)$_n$ wherein CA comprises the residue of an α-hydroxy carboxylic acid, (AA)$_n$ is an oligomeric segment comprising the residue of one or more independent α-amino acids, n is at least 1 and CA is bonded to (AA)$_n$ by an amide or an ester linkage. In accordance with a preferred embodiment, the α-hydroxy carboxylic acid is bonded to the residue of an α-amino acid with an amide bond to effectively create an α-amino acid oligomer that is "end-capped" by an α-hydroxy carboxylic acid residue.

If the reaction mixture does not contain an α-hydroxy carboxylic acid, an α-amino acid oligomer is formed that corresponds to the formula (AA)$_n$ wherein each AA is the residue of one or more independent α-amino acids, n is at least 2 and the amino acid residues are bonded to each other by an amide linkage or an ester.

It is important to note that when n is greater than 1, (AA)$_n$ may comprise more than one independent α-amino acid residue. Stated another way, (AA)$_n$ comprises a peptide comprising two or more independent α-amino acids. Thus, the composition of the oligomer may be advantageously tailored for specific applications. For example, in a preferred embodiment, the oligomer may be designed to meet the essential amino acid requirements of a particular animal by incorporating two or more different amino acid residues (e.g., methionine and lysine residues) into an oligomer. Such an example is an oligomer comprising lysine and methionine residues in a 3:1 ratio, which would meet the essential amino acid requirements of a ruminant.

Several variables affect the value of n, such as the amino acid monomer utilized, the reaction solution composition, and the method of isolating the co-oligomer products. Typically, n is less than 20. In some embodiments, n ranges from about 1 to about 10, more typically from about 2 to about 8 and, in some embodiments, from about 3 to about 5. For example, in oligomers comprising methionine residues, n typically ranges from about 4 to about 12, with an average of about 6 to about 8.

The oligomers of the present invention may be obtained (and used) as a dimer, trimer, tetramer, pentamer, hexamer, septamer, octamer, nonamer, decamer, etc. in which a residue of the α-hydroxy carboxylic acid is linked to a residue of an α-amino acid via an amide or ester linkage. Alternatively, an oligomeric segment may be obtained which is chemically or enzymatically linked to another moiety, for example, through the α-hydroxy group of the α-hydroxy carboxylic acid residue, the carboxy terminus of the α-amino acid residue (for oligomers comprising an amide linkage between the α-hydroxy carboxylic acid residue and the α-amino acid residue) or the amino terminus of the α-amino acid residue (for oligomers comprising an ester linkage between the α-hydroxy carboxylic acid residue and the α-amino acid residue).

In a preferred embodiment, the oligomer or oligomeric segment corresponds to the structure:

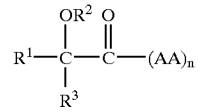

wherein
  $R^1$ is hydrogen, hydrocarbyl or substituted hydrocarbyl,
  $R^2$ is hydrogen, hydrocarbyl, substituted hydrocarbyl, or a hydroxy protecting group,
  $R^3$ is hydrogen, hydrocarbyl or substituted hydrocarbyl,
  each AA is the residue of an α-amino acid selected from the group consisting of α-amino acids independently of any other α-amino acid residue, and
  n is at least 1.

α-Hydroxy Carboxylic Acid Residue

In general, the oligomer or oligomeric segments of the present invention may comprise the residue of any α-hydroxy carboxylic acid. Preferred α-hydroxy carboxylic acids correspond to the general structure $R^1R^3C(OR^2)$COOH wherein $R^1$ is hydrogen, hydrocarbyl or substituted hydrocarbyl; $R^2$ is hydrogen, a hydroxy protecting group, hydrocarbyl, or substituted hydrocarbyl; and $R^3$ is hydrogen, hydrocarbyl or substituted hydrocarbyl, preferably hydrogen. For example, the α-hydroxy carboxylic residue may be the residue of any of the following naturally occurring α-hydroxy carboxylic acids (with $R^1$ for such acid being given in brackets): lactic acid [—CH$_3$], mandelic acid [—C$_6$H$_5$], malic acid [—CH$_2$COOH], and tartaric acid [—CH(OH)COOH]. In addition, the α-hydroxy carboxylic acid residue may be the residue of an α-hydroxy acid analog of a naturally occurring α-amino acid, more preferably the residue of the α-hydroxy analog of an essential α-amino acid, and still more preferably the residue of the α-hydroxy analog of methionine, i.e., 2-hydroxy-4-(methylthio)butyric acid.

In general, the α-hydroxy carboxylic acid residue may comprise the residue of an α-hydroxy carboxylic acid having the D- configuration, the L-configuration, or a racemic or other mixture of the D- and L-isomers. In some embodiments, however, it is generally preferred that the α-hydroxy carboxylic acid residue comprise the residue of an α-hydroxy carboxylic acid having the L-configuration.

Further, it is important to note that the α-hydroxy carboxylic acid residue incorporated into the oligomer may comprise the residue of more than one α-hydroxy carboxylic acid. Thus, the residue may comprise a homo-oligomer containing one or more α-hydroxy carboxylic acid monomers or a hetero-oligomer containing two or more independent α-hydroxy carboxylic acid monomers.

α-Amino Acid Residue(s)

In general, the oligomers of the present invention may comprise the residue of any α-amino acid. Preferred α-amino acids correspond to the general structure $R^aR^bC$(NH$_2$)COOH wherein $R^a$ is hydrogen, hydrocarbyl, substituted hydrocarbyl or heterocyclo; and $R^b$ is hydrogen. For example, the α-hydroxy amino residue(s) may be the residue(s) of any of the naturally occurring α-amino acids, e.g., asparagine, glycine, alanine, valine, leucine, isoleucine, phenylalanine, proline, serine, threonine, cysteine, methionine, tryptophan, tyrosine, glutamine, aspartic acid, glutamic acid, lysine, arginine, and histidine. Preferably, the α-amino acid residue(s) include the residue(s) of one or more essential α-amino acids, i.e., isoleucine, phenylalanine, leucine, lysine, methionine, threonine, tryptophan, histidine and valine. Still more preferably, the α-amino acid residue(s) include the residue(s) of methionine and/or lysine.

In general, the α-amino acid residue may comprise the residue of an α-amino acid having the D-configuration, the L-configuration, or a racemic or other mixture of the D- and L-isomers. In some embodiments, however, it is generally preferred that the α-amino acid residue comprise the residue of an α-amino acid having the L-configuration.

Further, it is important to note that the α-amino acid residue incorporated into the oligomer may comprise the residue of more than one α-amino acid. Thus, the residue may comprise a homo-oligomer containing one or more α-amino acid monomers or a hetero-oligomer containing two or more independent α-amino acid monomers.

Enzymatic Oligomerization

The oligomers of the present invention are enzymatically synthesized in a mixture. The mixture comprises at least one α-hydroxy carboxylic acid or a derivative thereof, at least one α-amino acid or a derivative thereof, and an enzyme.

The α-hydroxy carboxylic acid may be present in the mixture as a free acid or as a carboxylic acid derivative, e.g., the corresponding ester, acid halide, amide, anhydride, or ketene. Preferably, the α-hydroxy carboxylic acid and its derivatives have the formula $R^1R^3C(OR^2)COY$ or $R^1RC(OR^2)=C=O$ wherein $R^1$, $R^2$ and $R^3$ are as previously defined and Y is hydroxy (for the free acid), halogen (for acid halide derivatives), hydrocarbyloxy (for ester derivatives), amino (for amide derivatives), and hydrocarbylcarboxy (for anhydride derivatives). In some embodiments, the α-hydroxy carboxylic acid is preferably present in the mixture in the form of an ester, i.e., where Y is $—OR^5$ and $R^5$ is hydrocarbyl, more preferably alkyl, alkene, or aryl, still more preferably lower alkyl. In other embodiments, the α-hydroxy carboxylic acid is preferably present in the mixture in the form of an amide, i.e., where Y is $—NR^6R^7$ and $R^6$ and $R^7$ are independently hydrogen or hydrocarbyl, more preferably lower alkyl, still more preferably hydrogen.

The mixture may contain more than one α-hydroxy carboxylic acid species. Thus, for example, the mixture may contain the hydroxy analog of methionine (in one or more of its free acid, acid halide, amide, anhydride or ketene forms) and, in addition, one or more other α-hydroxy carboxylic acids such as lactic acid, mandelic acid, malic acid, or tartaric acid (in one or more of their respective free acid, acid halide, amide, anhydride or ketene forms).

In addition to, or instead of α-hydroxy carboxylic acid monomers, the mixture may further contain oligomers (e.g., dimers, trimers, tetramers, pentamer, hexamer, septamer, octamer, nonamer, decamer, etc.) of one or more α-hydroxy carboxylic acids. For example, the mixture may contain a homo-oligomer formed from HMB or another α-hydroxy carboxylic acid or a hetero-oligomer of an α-hydroxy carboxylic acid (e.g., HMB) and at least one other α-hydroxy carboxylic acid.

Similarly, the α-amino acids may be present in the mixture as a free acid or as a carboxylic acid derivative, e.g., the corresponding ester, acid halide, amide, anhydride, or ketene. In general, the α-amino acid and its derivatives have the formula $R^aR^bC(NH_2)COY$ or $R^aC(OR^2)=C=O$ wherein $R^a$, $R^2$ and $R^b$ are as previously defined and Y is hydroxy (for the free acid), halogen (for acid halide derivatives), hydrocarbyloxy (for ester derivatives), amino (for amide derivatives), and hydrocarbylcarboxy (for anhydride derivatives). In some embodiments, the α-amino acid is preferably present in the mixture in the form of an ester, i.e., where Y is $—OR^5$ and $R^5$ is hydrocarbyl, more preferably alkyl or aryl, still more preferably lower alkyl. In other embodiments, the α-amino acid is preferably present in the mixture in the form of an amide, i.e., where Y is $—NR^6R^7$ and $R^6$ and $R^7$ are independently hydrogen or hydrocarbyl, more preferably lower alkyl, still more preferably hydrogen.

The mixture may contain more than one α-amino acid species. Thus, for example, the mixture may contain one α-amino acid (in one or more of its free acid, acid halide, amide, anhydride or ketene forms) and, in addition, one or more other α-amino acids (in one or more of their respective free acid, acid halide, amide, anhydride or ketene forms). By way of further example, the mixture may contain methionine (in one or more of its free acid, acid halide, amide, anhydride or ketene forms) and, in addition, one or more other nutritionally important α-amino acid(s) such as lysine, tryptophan and/or phenylalanine (in one or more of their respective free acid, acid halide, amide, anhydride or ketene forms).

In addition to, or instead of α-amino acid monomers, the mixture may contain oligomers (e.g., dimers, trimers, tetramers, pentamer, hexamer, septamer, octamer, nonamer, decamer, etc.) of one or more α-amino acids. For example, the mixture may contain a homo-oligomer formed from methionine, lysine or other α-amino acid or a hetero-oligomer of an α-amino acid (e.g., methionine) and at least one other nutritionally important α-amino acid such as lysine, tryptophan and/or phenylalanine.

The reaction mixture further comprises an enzyme. The enzyme may be dissolved in the mixture or, alternatively, it may be adsorbed or otherwise immobilized onto a variety of substrates. For example, the enzyme may be immobilized onto controlled pore glass, agarose, sepharose, nylon, or polyethylene glycol. Enzymes may also be adsorbed, for example, onto activated charcoal, ion exchange resins, silica, polyacrylamide, collagen, starch, bentonite, ultramembrane filters, cellulose, alumina, titania, and polyvinylchloride. In addition, enzymes may be retained by entrapment, microencapsulation, liposome formation, hollow fiber, inorganic bridge formation, and aggregation.

The type of enzyme selected will determine the direction that an oligomerization process proceeds. For example, enzymes generally characterized as a protease when included in a reaction mixture along with, for example, an α-hydroxy carboxylic acid ethyl ester and an α-amino acid ethyl ester, will cause a peptide reaction product to be formed from the reaction mixture. The peptide reaction product comprises an oligomer comprising α-amino acids and the α-hydroxy carboxylic acid bonded together by amide bonds. Examples of suitable protease enzymes include serine proteinases (e.g., Trypsin, α-Chymotrypsin, Elastase, Carboxypeptidase, and Subtilisin), thiol proteinases (e.g., Papain, Ficin, Bromelain, Streptococcal proteinase, Cathepsins, Calpains, Clostripain, and Actinidin), metalloproteinases (e.g., Thermolysin), acid proteinases (e.g., Pepsin, Penicillopepsin, Chymosin, Cathepsin, and Renin), liver esterase (e.g., pig liver esterase), alkaline protease, carbonic anhydrase, nonribosomal peptide synthetase, thrombin, cardosins A or B, or pronase.

If, however, an enzyme such as a lipase enzyme is used, the reaction mixture containing the lipase enzyme, an α-hydroxy carboxylic acid, and an α-amino acid or derivative thereof, instead forms a polyester reaction product. Enantioselective lipase enzymes may be obtained from a variety of microorganisms such as *Candida cylindracea, Candida lipolytica, Candida antarctica* (bacteria) and fungi such as *Rhizopus oryzae, Aspergillus niger*, and the like. The reaction product will therefore comprise an oligomer wherein the α-amino acids and the α-hydroxy carboxylic acid are bonded together by ester bonds. If the reaction mixture comprises a lipase enzyme and an ester of an α-hydroxy carboxylic acid or a derivative thereof, an oligomer of α-hydroxy carboxylic acid will form wherein the monomers are linked together by ester bonds.

In a preferred embodiment, the mixture contains an enzyme which catalyzes the formation of peptide bonds. Exemplary enzymes include serine proteinases (e.g., Trypsin, α-Chymotrypsin, Elastase, Carboxypeptidase, and Subtilisin), thiol proteinases (e.g., Papain, Ficin, Bromelain, Streptococcal proteinase, Cathepsins, Calpains, Clostripain, and Actinidin), metalloproteinases (e.g., Thermolysin), acid proteinases (e.g., Pepsin, Penicillopepsin, Chymosin, Cathepsin, and Renin), liver esterase (e.g., pig liver esterase), alkaline protease, carbonic anhydrase, nonribosomal peptide synthetase, thrombin, cardosins A or B, or pronase.

Enantioselective Enzymatic Oligomerization

It has further been found that the present invention may be utilized to enzymatically synthesize oligomers, co-oligomers, or segments thereof, consisting of α-hydroxy carboxylic acid isomers and α-amino acid isomers or α-amino acid isomers wherein one enantiomer of the α-hydroxy carboxylic acids, α-amino acids, or derivatives thereof is incorporated into the co-oligomer or oligomer in preference to the other enantiomer. Stated another way, it has been found that by using an enantioselective enzyme in the process of the present invention, peptide or ester reaction products comprising co-oligomers, oligomers or segments thereof can be formed from a reaction mixture comprising an enantiomeric mixture of α-hydroxy carboxylic acids, α-amino acids, or derivatives thereof, wherein one enantiomer of the enantiomeric mixture is incorporated into the reaction product in preference to the other enantiomer of the mixture.

As previously described for enzymatic oligomerization, the oligomers of the present invention are enantioselectively synthesized in a mixture. The mixture comprises at least one at least one α-amino acid or a derivative thereof as described above, an enantioselective enzyme; and, optionally a α-hydroxy carboxylic acid or a derivative thereof as described above.

The α-hydroxy carboxylic acids and α-amino acids may be present in the mixture as enantiomeric mixtures. An enantiomeric mixture contains enantiomeric pairs of the α-hydroxy carboxylic acids, α-amino acids, or derivatives thereof. The proportion of each species may vary from a racemic mixture that contains equal proportions of the D- and L-isomer configurations (e.g., 50% of the L-isomer and 50% of the D-isomer), to enantiomeric mixtures wherein one species is proportionally greater than its opposite species (e.g., an enantiomeric mixture containing 70% L-isomer and 30% D-isomer).

In one embodiment of the present invention, the reaction mixture contains a racemic mixture of α-amino acid. In another embodiment, the reaction mixture contains a racemic mixture of α-hydroxy carboxylic acid. In still another embodiment, the reaction mixture contains racemic mixtures of both α-hydroxy carboxylic acid and α-amino acid.

In general, the mixture contains an enzyme which enantioselectively catalyzes the formation of peptide bonds between α-amino acids having identical chiral configurations (e.g., L-isomers of amino acids). Thus, the co-oligomer or oligomer formed from the mixture comprises a residue of an α-hydroxy carboxylic acid bonded to a peptide by an amide linkage or an ester linkage, wherein the peptide comprises two or more independent α-amino acid residues having identical chiral configuration.

In another embodiment, the enzyme further enantioselectively catalyzes the formation of the amide or ester linkage between the α-hydroxy carboxylic acid residue and the α-amino acid residue such that the oligomer comprises one α-hydroxy carboxylic acid enantiomer linked to the α-amino acid oligomer in preference to another α-hydroxy carboxylic acid enantiomer. For example, a reaction mixture containing papain, an enantiomeric mixture of methionine ethyl ester isomers and an enantiomeric mixture of HMB ethyl ester isomers will form oligomers consisting of L-HMB linked to one or more L-methionine residues. The enantiospecificity of the enzyme is dependent upon the α-amino acid and α-hydroxy carboxylic acid being oligomerized. Exemplary enantioselective enzymes include thiol proteinases (e.g., Papain, Bromelain, Cathepsin s, Cathepsin b, and Cathepsin c) and serine proteinases (e.g., some forms of Subtilisin). In a preferred embodiment, the enantioselective enzyme enzymatically links the carboxy terminus of the α-hydroxy carboxylic acid to the amino terminus of the α-amino acid.

It is important to note that either of the α-hydroxy carboxylic acid residue or the α-amino acid residues may comprise an oligomer (i.e., a dimer, trimer, etc.) as described above and still be enantioselectively incorporated into the oligomers of the present invention. For example, if the enantioselective enzyme in the reaction mixture is suitable for incorporating oligomers comprising the L-enantiomer, the enzyme will catalyze the oligomerization of any α-hydroxy carboxylic acid residue or α-amino acid residue having an L-configuration.

The enantioselective enzyme may be dissolved in the mixture or, alternatively, it may be adsorbed or otherwise immobilized onto a variety of substrates. For example, the enzyme may be immobilized onto controlled pore glass, agarose, sepharose, nylon, or polyethylene glycol. Enantioselective enzymes may also be adsorbed, for example, onto activated charcoal, ion exchange resins, silica, polyacrylamide, collagen, starch, bentonite, ultramembrane filters, cellulose, alumina, titania, and polyvinylchloride. In addition, enzymes may be retained by entrapment, microencapsulation, liposome formation, hollow fiber, inorganic bridge formation, and aggregation.

In one embodiment, the oligomer formed from the enantioselective oligomerization comprises a composition comprising a residue of an α-hydroxy carboxylic acid bonded to a peptide by an amide or an ester linkage, wherein the peptide comprises two or more α-amino acid residues and each of the α-amino acids of the peptide are independently selected from the group consisting of α-amino acids. Preferably, more than 50% of the α-amino acid residues in the peptide are of identical chirality and, more preferably, essentially all of the α-amino acid residues in the peptide are of identical chirality.

In a preferred embodiment, the oligomer or oligomeric segment formed by an enantioselective enzyme corresponds to the structure:

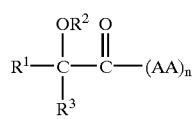

wherein,
R$^1$ is hydrogen, hydrocarbyl or substituted hydrocarbyl,
R$^2$ is hydrogen, hydrocarbyl, substituted hydrocarbyl, or a hydroxy protecting group,
R$^3$ is hydrogen, hydrocarbyl or substituted hydrocarbyl,
each AA is the residue of an α-amino acid or derivative thereof wherein greater than one-half of the AA residues are derived from α-amino acids or derivatives thereof having the same chiral configuration, and
n is at least 2.

For example, a mixture of papain, an enantiomeric mixture of HMB ethyl ester, and an enantiomeric mixture of D,L-methionine ethyl ester in a reaction mixture has been found to form homo-oligomers of L-methionine and hetero-oligomers of L-HMB/L-methionine wherein the L-HMB is linked through its carboxy terminus to the amino terminus of the methionine oligomer. The homo-oligomers and hetero-oligomers may be separated out of the solution by precipitation, filtration, selective extraction, column chromatography, lyophilization, and evaporation techniques. Typically, an oligomer comprising about nine methionine amino acids will precipitate out of solution and may be easily filtered or centrifuged away from the reacting mixture containing the free hydroxy acids and α-amino acids. Soluble methionine oligomers comprised of lower numbers of methionine residues can be separated from the free amino and hydroxy acids using membrane filtration. Once the reaction is allowed to run to near completion, the remaining reaction mixture contains papain, a significant amount of monomers of D-HMB ethyl ester and D-methionine ethyl ester (e.g., about 95% of the total amount of HMB ethyl ester and methionine ethyl ester isomers), and a small amount of L-HMB ethyl ester and L-methionine ethyl ester. Papain may be removed from the solution by size exclusion chromatography or similar separation technique known in the art. The remaining monomers of D-HMB ethyl ester and D-methionine ethyl ester may be removed from solution by rotary evaporation for purification or transformed to their respective L-isomer form through base racemization and recycled.

If the reaction mixture does not contain an α-hydroxy carboxylic acid, but does contain an enantioselective enzyme and an α-amino acid or derivative thereof, an α-amino acid oligomer is formed that corresponds to the formula (AA)$_n$. AA is the residue of an α-amino acid comprising two or more independent α-amino acids wherein greater than one-half of the AA residues are derived from α-amino acids or derivatives thereof having the same chiral configuration, n is at least 2, and the amino acid residues are bonded to each other by an amide linkage. Typically, n will be less than 20. In some embodiments, n will range from about 2 to about 10, more typically from about 2 to about 8 and, in some embodiments, from about 3 to about 5. In methionine oligomers, for example, n typically will range from about 4 to 12, with an average of 6 to 8.

Enzymatic Reaction Mixtures

In one embodiment of the present invention, the enzymatic reaction is carried out in a single phase, aqueous solution under conditions typically employed in enzyme catalyzed reactions for the preparation of oligomers and co-oligomers of α-amino acids. Such systems are typically used in enzymatic biochemical reaction. See, e.g., Lehninger, Nelson, and Cox, Principles of Biochemistry, 1993, Worth Publisher, NY, N.Y.

In a second embodiment of the present invention, the enzymatic reaction is carried out in a two-phase system comprising an aqueous phase and an organic phase. In general, the organic phase comprises an organic solvent selected from the group consisting of alkanes, alkenes, aryls and suitable derivatives thereof. See, e.g., Olmsted and Williams, Chemistry the Molecular Science, 1994, Mosby Publisher, St. Louis, Mo.

In a third embodiment of the present invention, the enzymatic reaction is carried out in a reverse micelle system. Such a system comprises a continuous organic phase, a dispersed aqueous phase, and a surfactant to obtain and stabilize micelle phase. In general, the organic phase comprises an organic solvent selected from the group consisting of alkyl, aryl, and suitable derivatives thereof, and the surfactant is selected from the group consisting of ionic or non-ionic surfactants. Such reverse micelle systems are typically used for biotechnological reactions. See, e.g., Vicente, Aires-Barros, and Empis, *J. Chem. Tech. Biotechnol.* 1994, 60, 291.

In a fourth embodiment of the present invention, the enzymatic reaction is carried out in a three-phase system comprising an aqueous phase, a first organic phase and a second organic phase with the two organic phases being immiscible. In general, the first organic phase comprises an organic solvent selected from the group consisting of hydrocarbon solvents and the second organic phase comprises an organic solvent selected from the group consisting of halogenated hydrocarbon, perhalogenated hydrocarbon, and halogenated hydrocarbyl solvents. Such three phase systems are routinely used for chemical and biochemical reactions.

In general, the reaction may be carried out over a relatively wide range of temperatures, e.g., about 4° C. to about 50° C., typically about 35 to about 40° C. The pH of the aqueous phase is typically about 5.5 to about 9. Depending upon whether the reaction is carried out in a single phase, aqueous solution or in a multi-phase system, the ratio of the water phase to the organic phase may range from 100:0 to 0.1:99.9 parts by weight, respectively. Reaction time may varying from minutes to hours (e.g., from about 10 minutes to about 24 hours or more) depending on the desired yield and the synthesis may be achieved both with and without physical agitation of the reaction mixture.

Separation

Specific oligomers and co-oligomers can be separated from the reaction mixtures through precipitation, filtration, selective extraction, column chromatography, lyophilization, and evaporation techniques. Often, the oligomeric and co-oligomeric products are precipitates which may be easily filtered or centrifuged away from the peptide and ester reaction product mixture containing free hydroxy acids and unreacted α-amino acids. For example, soluble oligomer and co-oligomeric products can be separated from reaction product mixture using membrane filtration. Alternatively, free amino acids and α-hydroxy acids may be removed from the product mixture using ion exchange or other applicable chromatographic technique. The selection of separation procedure is dependent on the desired oligomers and co-oligomers.

When enantioselective enzymes are utilized to form co-oligomers consisting of α-hydroxy carboxylic acid isomers and α-amino acid isomers having identical chiral configurations from a reaction mixture containing a racemic mixture of α-hydroxy carboxylic acid isomers and a racemic mixture of α-amino acids, the reaction mixture after the reaction is formed will contain the enzyme and a greater proportion of the non-selected enantiomers of α-hydroxy carboxylic acid and α-amino acid than the non-selected enantiomers. The enzyme may be removed from solution by filtration and recycled, thereby leaving a solution primarily containing monomers of the non-selected enantiomers. Further, the non-selected enantiomers may be separated from the solution by rotary evaporation or by other methods known in the art. After separation, the non-selected enantiomers may be transformed into the monomeric form of the selected isomer through base racemization and recycled. For example, when the L-isomer of methionine is oligomerized or co-oligomerized by papain in a reaction mixture containing a racemic mixture of methionine and HMB, at the end of the reaction, the mixture will primarily be comprised of papain, D-methionine, and D-HMB. Papain may be simply filtered from the reaction mixture by size exclusion chromatography leaving a solution primarily containing D-methionine (e.g., approximately 95% or more of the remaining racemic mixture of methionine) which may be isolated by rotary evaporation.

Alternatively, the process of the present invention can be used to recover the selected enantiomer from the separated oligomer. For example, the recovered oligomer may be hydrolyzed with acid to separate the first, selected enantiomer or derivative thereof from other hydrolyzates. The separated enantiomer may then be racemized and recycled for further use.

Uses

Biological systems such as ruminants, poultry, swine, and aquatic animals readily absorb and utilize the L-isomers of amino acids but are unable to utilize the corresponding D-isomer without first transforming the D-isomer into the L-isomer through an oxidation followed by transamination enzymatic reactions. As such reactions require additional time and energy to be expended by the animal before the amino acids can be utilization by the animal, feed supplements of L-isomer oligomers and co-oligomers are advantageous as they can be utilized by the animal with minimal expenditure of energy, which ultimately improves the growth rate of the animals.

The enantioselective oligomerization and co-oligomerization of specific enantiomers of α-hydroxy carboxylic acids, α-amino acids, or derivatives thereof results in the purification of the species in the original enantiomeric mixtures. First, by selectively oligomerizing or co-oligomerizing enantiomeric species, such as the L-enantiomers, the resulting oligomers and co-oligomers formed are therefore a more pure form of L-enantiomers. The L-enantiomers may then be isolated through addition of acid to the oligomers and co-oligomers thereby hydrolyzing them into the L-enantiomers with which they are comprised. The L-isomers may be further isolated from each other through chromatographic or other separation means known in the art.

Conversely, while the L-isomers are being selectively oligomerized and co-oligomerized, the reaction mixture contains an increasingly greater proportion of the non-selected enantiomer species, for example, the D-enantiomers. Thus, as the reaction progresses, the remaining unreacted enantiomers, such as D-α-hydroxy carboxylic acids, D-α-amino acids, or derivatives thereof, may be recovered from the reaction mixture by rotary evaporation or other means. The D-isomers of α-hydroxy carboxylic acids, α-amino acids, or derivatives thereof may then be transformed to their respective L-isomer form through base racemization and reused as reactants in additional oligomerization and co-oligomerization reactions.

Depending upon the desired application, the α-hydroxy carboxylic acid/α-amino acid co-oligomer and α-amino acid oligomer compositions of the present invention may be provided to animals as an amino acid supplement. The α-hydroxy carboxylic acid/α-amino acid co-oligomer and α-amino acid oligomer compositions may be fed or otherwise administered orally, or sprayed into the eye, ear or nasal cavity of an animal, preferably a ruminant. Alternatively, the compositions may be injected, or administered bucchally (i.e., to the gums), sublingually (i.e., beneath the tongue) or rectally.

The α-hydroxy carboxylic acid/α-amino acid co-oligomer compositions of the present invention or α-amino acid oligomer compositions enzymatically formed in the absence of an α-hydroxy carboxylic acid may also be used to supplement the diets of animals not possessing rumens, such as poultry, swine, and aquatic animals. As with ruminants, these compositions may be fed or otherwise administered orally, bucchally, sublingually, rectally, sprayed into the eye, ear or nasal cavity of an animal, or injected into the animal.

These compositions may be further used in aquaculture by applying the compositions to an aquatic habitat in a particle size that is able to be ingested by the target animal. The compositions may be used in aquaculture as particles of the α-amino acid oligomer or α-hydroxy carboxylic acid/α-amino acid co-oligomer itself or as an ingredient in the animal's feed rations. While oligomers and co-oligomers may be utilized in varying sizes, feed mills typically manufacture feed supplements in particle sizes of about 0.25 mm or more for incorporation into feed rations. The feed ration pellets containing the oligomer or co-oligomer ingredient would be sized according to the animal to which it is being fed. For example, fish, such as carp and trout, may be fed the oligomer or co-oligomer compositions as an ingredient of a feed ration that is applied to the surface of the water. Feed mills typically produce fish feed rations in particle sizes that range between about 4 mm to about 5 mm in diameter. Conversely, for smaller aquatic animals, such as shrimp, that cannot ingest large particles due to small mouth size, the compositions may be applied to the surface of the water as pure forms of the oligomer or co-oligomer or as ingredients of a feed ration in smaller feed particle sizes. Feed mills typically produce rations for smaller aquatic animals in particles that are at least 1.6 mm in diameter, preferably between about 2 mm to about 3 mm in diameter, more preferably between about 2.2 mm to about 2.4 mm in diameter. The length of the feed ration pellets are typically manufactured to be two to three times the length of the diameter. While feed mills may produce feed rations in particular size ranges, the dimensions of the ration that incorporates the oligomer or co-oligomer composition may be varied therefrom without diminishing the effectiveness of the oligomer or co-oligomer.

In another embodiment, the α-hydroxy carboxylic acid/α-amino acid co-oligomer or α-amino acid oligomer compositions may be used as a protective coating for vitamins, minerals, and other nutrient supplements that are ingested by both humans and other animals, for example, ruminants, poultry, swine, and aquatic animals. Vitamins and other nutritional supplements (e.g., vitamin A, acetate or palmitate ester, and the like) which are ingested often must be protected against acids and proteolytic enzymes present in the stomach and rumen in order to be available for absorption by the animal in the intestine. These supplements may often also be soluble in water or sensitive to oxidation such that they cannot remain in a solid form that can be ingested and utilized in an aqueous environment. Currently, protective coatings, such as fat and gelatin based coatings, are applied to vitamins and nutrients to protect against their degradation in the stomach or rumen or dissolution in water. These coatings may be made from animal products such as beef fat and gelatin. Such sources have recently come under scrutiny due to potential diseases carried by the animals which may affect the availability and quality of fats and gelatin used for coatings.

The α-hydroxy carboxylic acid/α-amino acid co-oligomer or α-amino acid oligomer compositions provide a superior alternative to animal-based coatings. As some oligomer or co-oligomer compositions may be resistant to degradation in the stomach and rumen, as well as insoluble in water, they may be used as vitamins, minerals, and other nutrient coatings. Thus, in ruminants, the co-oligomer compositions may coat supplements in order for the vitamins, minerals, and other nutrients to bypass microbial degradation that occurs in the rumen. Once in the small intestine, the co-oligomer compositions are completely degraded wherein the ruminant may absorb the α-hydroxy carboxylic acids, amino acids, and the previously coated vitamins, minerals, and nutrients. Once absorbed, the ruminant may convert the α-hydroxy carboxylic acids from the coating to its respective amino acid for utilization by the ruminant. Since the α-hydroxy carboxylic acid/α-amino acid co-oligomer and α-amino acid oligomer coatings are enzymatically synthesized, they do not introduce the risk of infecting the ruminant with a disease that may have been carried by an animal from which a fat or gelatin based coating is derived.

For non-ruminants, gastric acids and enzymes present in the stomach begin to degrade the coating as it passes through the stomach to the intestine. Once in the intestine, the coating is completely degraded, and the previously encapsulated vitamins, minerals, and other nutrients may be absorbed.

Some supplements, such as vitamin A, are soluble in water. Left uncoated, the soluble supplements would dissolve into the surrounding water and pollute it rather than provide the aquatic animals with the vitamins, minerals, and other nutrient supplements they need. As the α-hydroxy carboxylic acid/α-amino acid co-oligomer or α-amino acid oligomer compositions are also insoluble in water, they also may be beneficially used to coat vitamins, minerals and other nutrient supplements for use in aquaculture.

The application of α-hydroxy carboxylic acid/α-amino acid co-oligomer or α-amino acid oligomer coatings to vitamins and other nutritional supplements may be achieved by methods known in the art. For example, the oligomer or co-oligomer may be dissolved in a volatile solvent and subsequently spray coated on a fluidized bed of the supplements. As the solvent evaporates, a coating of α-hydroxy carboxylic acid/α-amino acid co-oligomer or α-amino acid oligomer remains on the supplements which may then be provided to the animal.

Definitions

The term "aquaculture" refers to the cultivation of aquatic animals including, but not limited to, freshwater and salt water fish (e.g., carp, trout, catfish, bass, sea bass, cod, salmon, and fish related thereto) and crustaceans (e.g., shrimp, crabs, lobster, freshwater shrimp, and the like).

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Preferably, these moieties comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy; nitro, amino, amido, nitro, cyano, and thiol.

The alkyl groups described herein are preferably lower alkyl containing from one to six carbon atoms in the principal chain and up to 20 carbon atoms. They may be straight or branched chain and include methyl, ethyl, propyl, isopropyl, butyl, hexyl and the like.

The alkenyl groups described herein are preferably lower alkenyl containing from two to six carbon atoms in the principal chain and up to 20 carbon atoms. They may be straight or branched chain and include ethenyl, propenyl, isopropenyl, butenyl, isobutenyl, hexenyl, and the like.

The alkynyl groups described herein are preferably lower alkynyl containing from two to six carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic hydrocarbon groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include furyl, thienyl, pyridyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, and thiol.

The acyl moieties described herein contain hydrocarbyl, substituted hydrocarbyl or heterocyclo moieties.

The terms "hydroxyl protecting group" and "hydroxy protecting group" as used herein denote a group capable of protecting a free hydroxyl group ("protected hydroxyl") which, subsequent to the reaction for which protection is employed, may be removed without disturbing the remainder of the molecule. A variety of protecting groups for the hydroxyl group and the synthesis thereof may be found in "Protective Groups in Organic Synthesis" by T. W. Greene, John Wiley and Sons, 1981, or Fieser & Fieser. Exemplary hydroxyl protecting groups include acetyl (Ac), benzyl (PhCH$_2$—), 1-ethoxyethyl (EE), methoxymethyl (MOM), (methoxyethoxy)methyl (MEM), (p-methoxyphenyl) methoxymethyl (MPM), tert-butyldimethylsilyl (TBS), tert-butyldiphenylsilyl (TBPS), tert-butoxycarbonyl (Boc), tetrahydropyranyl (THP), triphenylmethyl (Trityl, Tr), 2-methoxy-2-methylpropyl, benzyloxycarbonyl (Cbz), trichloroacetyl ($OCCCl_3$), benzyloxymethyl (BOM), tert-butyl (t-Bu), triethylsilyl (TES), trimethylsilyl (TMS), and triisopropylsilyl (TIPS).

The abbreviation "HMB" shall mean the 2-hydroxy analog of methionine, i.e., 2-hydroxy-4-(methylthio)butyric acid.

The terms "chiral," "chiral configuration," and "enantiomer" refer to a particular stereoisomer of a molecule. For example, L-methionine and L-HMB.

The term "identical chirality" or "identical chiral configuration" refers to the chiral carbon of two or more molecules having the same stereoisomeric configuration. For example, all L-isomers of α-amino acid have identical chiral configuration. Thus, in the general α-amino acid structure, $R^a R^b C (NH_2)COOH$, wherein $R^a$ is hydrogen, hydrocarbyl, substituted hydrocarbyl or heterocyclo; and $R^b$ is hydrogen, the —COOH, —NH2, $R^a$, and $R^b$ constituents of L-isomers of α-amino acid have the same spatial arrangement around the chiral carbon. Similarly, the two or more L-enantiomers of a specific α-hydroxy carboxylic acid, such as two molecules of L-HMB, will have identical configuration to each other.

The term "enantioselective" refers to the selection of a specific enantiomer of an enantiomeric mixture and interactions with said enantiomer. For example, an enantioselective enzyme, such as papain, selectively catalyzes the linkage of L-methionine ethyl esters to form an oligomer of L-methionine residues.

EXAMPLES

The following Examples set forth one approach that may be used to carry out the process of the present invention. Accordingly, these examples should not be interpreted in a limiting sense.

Example 1

Synthesis of Methionine Oligomers and HMB-Methionine Co-Oligomers

This example demonstrates the enzymatic synthesis of oligomers comprising methionine and co-oligomers comprising HMB-methionine, as well as their characterization using reverse-phase HPLC and matrix assisted laser desorption ionization-time of flight mass spectroscopy (MALDI-TOF MS) analysis.

Co-Oligomerization

In a first synthesis, the experiment was generally conducted in accordance with reaction conditions for the papain-catalyzed oligomerization of methionine analogs as described by Arai et al. in *Agric. Biol. Chem.*, 43(5), 1069–1074 (1979). The oligomerization comprised forming a reaction mixture at a temperature of 37° C. consisting of nanopure filtered water (10 mL) containing HMB ethyl ester (0.7 M) and methionine ethyl ester (0.7 M) along with L-cysteine (0.1 M), EDTA (10 mM), sodium citrate (1M) and 1% papain (by weight of the monomer) at a pH of 5.5. The mixture was allowed to incubate for 24 hours. After 10 minutes, aliquots were removed at regular intervals to monitor the degree of oligomerization and co-oligomerization and the disappearance of the substrate.

In a second synthesis, the experiment was conducted in accordance with reaction conditions for the papain-catalyzed oligomerization of methionine analogs as described by Jost et al. in *Helv. Chim. Acta,* 63 (1980) 375–384 (1980). The oligomerization comprised forming a reaction mixture consisting of L-methionine ethyl ester (5 g) and HMB ethyl ester (5 g) dissolved in nanopure water (50 mL) containing sodium bicarbonate buffer (0.1 mole) and L-cysteine (4 mmole). The pH was adjusted to 9 and the solution was made up to 100 mL and incubated for 24 hours at 37° C. after adding papain (2 g).

Analysis of Oligomers

In all cases, aliquots were removed from the oligomerization reaction mixtures and heated to 80° C. for 10 minutes to denature the enzyme. The mixture was centrifuged and the supernatant was analyzed on a reverse-phase HPLC to monitor the synthesis of methionine oligomers of order 3 or less along with the disappearance of the substrate. Attempts at resolving the higher order oligomers with RPLC and gel permeation liquid chromatography (GPC) were unsatisfactory especially for oligomers with 4–10 monomer residues. For example, the experiments revealed that underivatized oligomers could not be eluted from C-18 or C-8 columns with the common mobile phases due to poor solubility of oligomers in these mobile phases. The oligomers were soluble in dimethyl sulfoxide (DMSO) and tetrahydrofuran (THF) a common mobile phase in GPC for separations. However, oligomers with less than ten residues could not be resolved from the solvent in GPC separations. A persulfonation procedure was therefore adopted. Persulfonation of oligomers enhanced the polarity of the oligomers to a point that these could be separated on a C-18 column with a moderately polar mobile phase (M. Spindler, R. Stadler and H. J. Tanner, *J. Agri. Food Chem.,* 32(6) (1984)1366–1371).

Persulfonation of Oligomers

The problem of analysis of higher order oligomers was addressed by the oxidation of the methionine and the HMB to their relatively hydrophilic sulfones with performic acid. The mixture was washed thoroughly until no traces of the monomers and the salts were left behind. The mixture was then freeze dried and a part of it was subjected to persulfonation with a method which was adapted from a procedure outlined by Spidler and coworkers. The procedure involved oxidation of all sulfide moieties in the oligomers with performic acid. The performic acid for the purpose was prepared by oxidation of formic acid (HCOOH) with hydrogen peroxide ($H_2O_2$). A solution of 30% $H_2O_2$ (0.5 mL) was mixed with 88% HCOOH (4.5 mL) and phenol (25 mg). The mixture was allowed to stand for 30 minutes at room temperature. After 30 minutes, the mixture was cooled to 0° C. for 15 minutes in an ice bath. The finely divided oligomer powder (10 mg) was then contacted with the performic acid mixture in the ice bath. After stirring for 15 minutes, the oligomer—performic acid mixture was placed in a refrigerator overnight. The excess performic acid was reduced with 48% hydrobromic acid (0.7 mL). The residual bromine and formic acid were removed with a rotary evaporator at 50–60° C.

Liquid Chromatography

The oligomer sulfone residues in the rotary evaporator round bottom flasks were dissolved in a 40:60 acetonitrile/water mixture (5 mL) and filtered through a membrane filter. A 10 µL aliquot of the solution was injected into a HPLC. The separation of persulfonated oligomers was achieved with a C-18 column using a phosphate buffer—acetonitrile mobile phase. A linear gradient was used to facilitate separations. In this gradient the mobile phase composition was changed from 100% eluant A (phosphate buffer, pH 6.5) to 60% A and 40% B (20% Acetonitrile) in 20 minutes. The mobile phase flow rate was maintained at 1 mL min$^{-1}$. The separated oligomers were detected with a UV/VIS diode array detector.

TOF Experiments

Aliquots of purified oligomers dissolved in DMSO were introduced into the mass spectrometer along with a thioglycerol matrix. The mass spectrometer operating parameters were:

| | |
|---|---|
| Accelerating Potential | +20 KV |
| Grid Voltage | 80% |
| Low Mass Gate | 191.0 |
| Flight tube pressure | $3.3\ e^{-7}$ torr |

MALDI-TOF Analysis

The MALDI-TOF spectra of methionine (Met) oligomers are shown in FIG. 1. The spectra contain distinct ions which are separated by mass 131. This mass (131) represents the repeating Met moiety ($C_5H_9NOS$), since the masses of the N and C terminal methionine residues are 132 and 148 respectively. Therefore, a methionine hexamer $(Met)^6$, $(^N Met\text{-}(Met)_4\text{-}Met^C)+H^+$ should appear at m/z 805 and $(Met)^7$ should appear at m/z 936. However, the m/z values of the dominant ions did not correspond to this series, instead, one set of dominant ions appeared at m/z 826, 957, 1088, 1219, 1350 and 1481. These ions most likely correspond to $((Met)^n+Na^+)$, where n is an integer between 6 and 11. The second group of ions appeared at m/z 724, 855, 986, 1117, 1248 and 1379. These ions most likely correspond to the series $(^N Met\text{-}(Met)\text{-}Met\text{-}O\text{—}C_2H_5)+Na^+$. A third set of ions appeared at m/z 739, 870, 1001 and 1134, these ions most likely correspond to $^N Met\text{-}(Met)_n\text{-}Met\text{-}O\text{—}C_2H_5+K^+$. A fourth set of unidentified ions seem to be present at regular intervals in the clusters and which might be assigned the mass values, 842, 973, 1104, 1235 and 1366 corresponding to the series $^N Met\text{-}(Met)_n\text{-}Metc)+K^+$. In all these cases "n" varied between 6 to 11.

Figure 2:
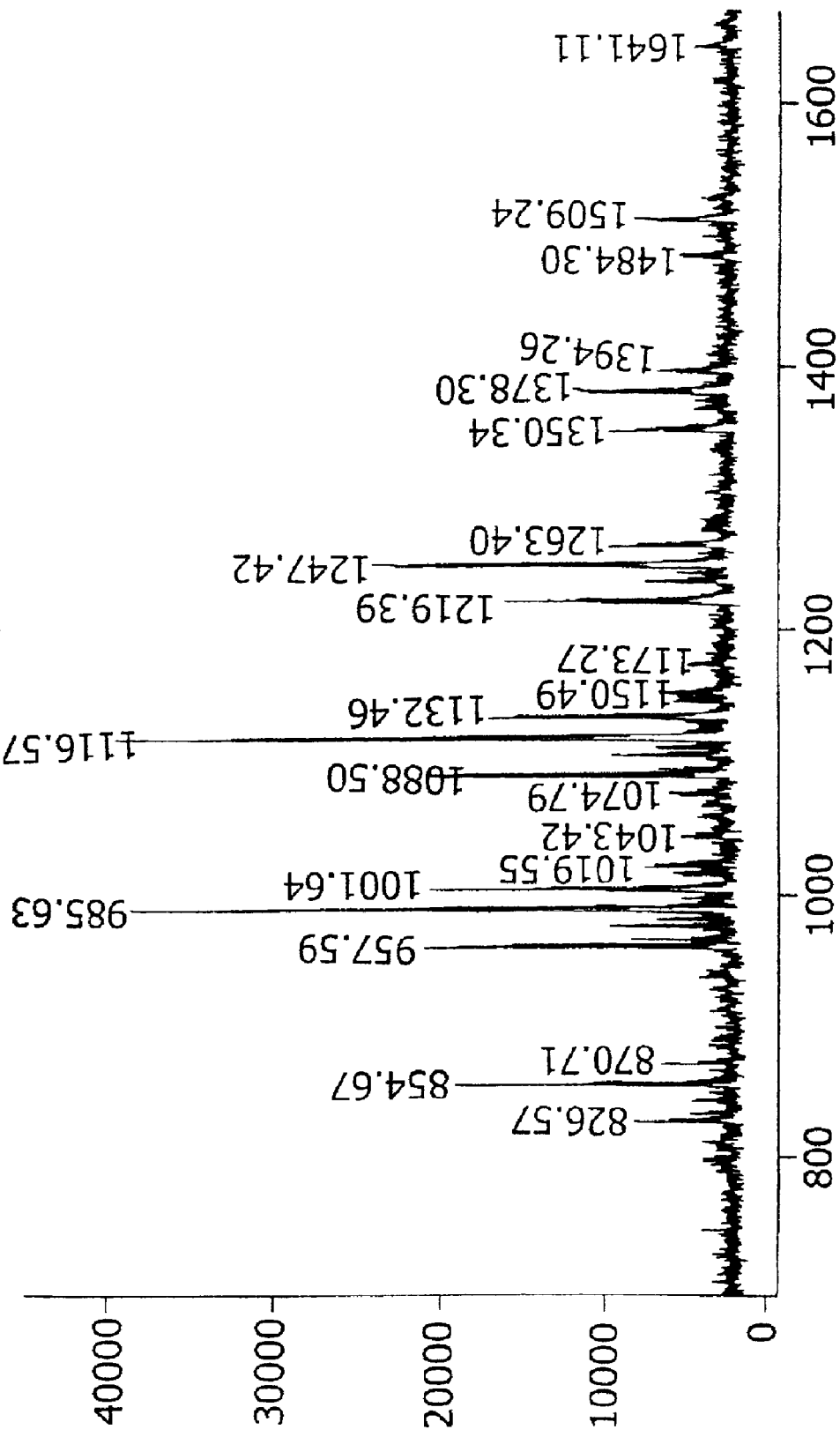
FIG. 2 is a MALDI-TOF graph of HMB-methionine co-oligomers from a papain catalyzed synthesis.

The spectra of HMB—Met co-oligomers is shown in FIG. 2. In this spectra, ions corresponding to the series $(^N Met\text{-}(Met)_n\text{-}Met^C)+Na^+$, $(^N Met\text{-}(Met)_n\text{-}Met\text{-}O\text{—}C_2H_5)+Na^+$, $^N Met\text{-}(Met)_n\text{-}Met^C+K^+$, and $^N Met\text{-}(Met)_n\text{-}Met\text{-}O\text{—}C_2H_5K^+$ were readily observed. However, the ions, which should correspond to $(HMB\text{-}(Met)_n\text{-}Met^C)+H^+$ or $+Na^+$ m/z 806, 937 and 1118; 827, 958 and 1089 were not observed in the spectra. The apparent absence of these ions, however, does not necessarily mean the absence of $HMB\text{-}(Met)^n$ co-oligomers in the product mixture. The absence of the ions can be attributed to two factors. The first relates to the low resolving power of the MALDI-TOF MS, which would prevent the resolution of the $H^+$ $HMB\text{-}(Met)^n\text{-}Met^C$ ions at m/z 806, 937, 1118 from the $H^{+N}Met\text{-}(Met)^n\text{-}Met^C$ ions at m/z 805, 936, 1117. The second and more probable cause is the low intensity of the $H^+HMB\text{-}(Met)^n\text{-}Met^C$ ion due to the absence of a good protonation site in $HMB\text{-}(Met)^n$ co-oligomers.

HPLC Separations of Oligomers Sulfones

Figure 3:
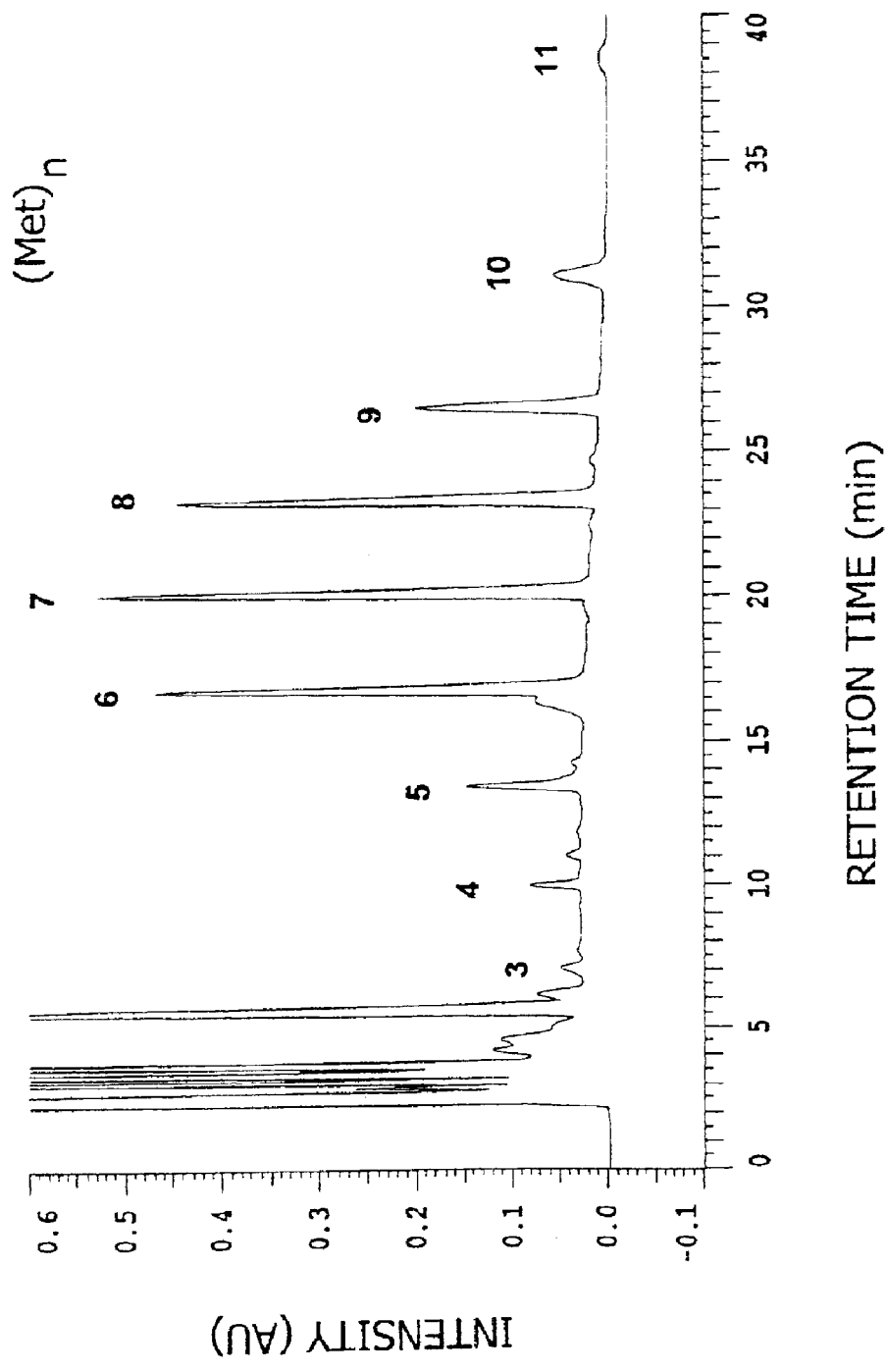
FIG. 3 is a HPLC graph of methionine sulfone oligomers.

The chromatographic separations of poly-methionine sulfones are shown in FIG. 3. A number of well-resolved peaks can be readily observed. Of these, nine did not appear in the reagent blank and most likely represent the poly-methionine sulfones. This chromatographic separation is nearly identical to the chromatographic separations reported by Kasai et al. (T. Kasai, T. Tanaka, and S. Kiriyama, *Biosci. Biotech. Biochem.*, 56(11) (1992) 1884–1885). However, because of a difference in the separation column or variations in the eluant composition, the retention times reported by Kasai et al. for most oligomers were approximately 0.5–0.6 minutes longer than retention times observed by the present inventors.

Figure 4:
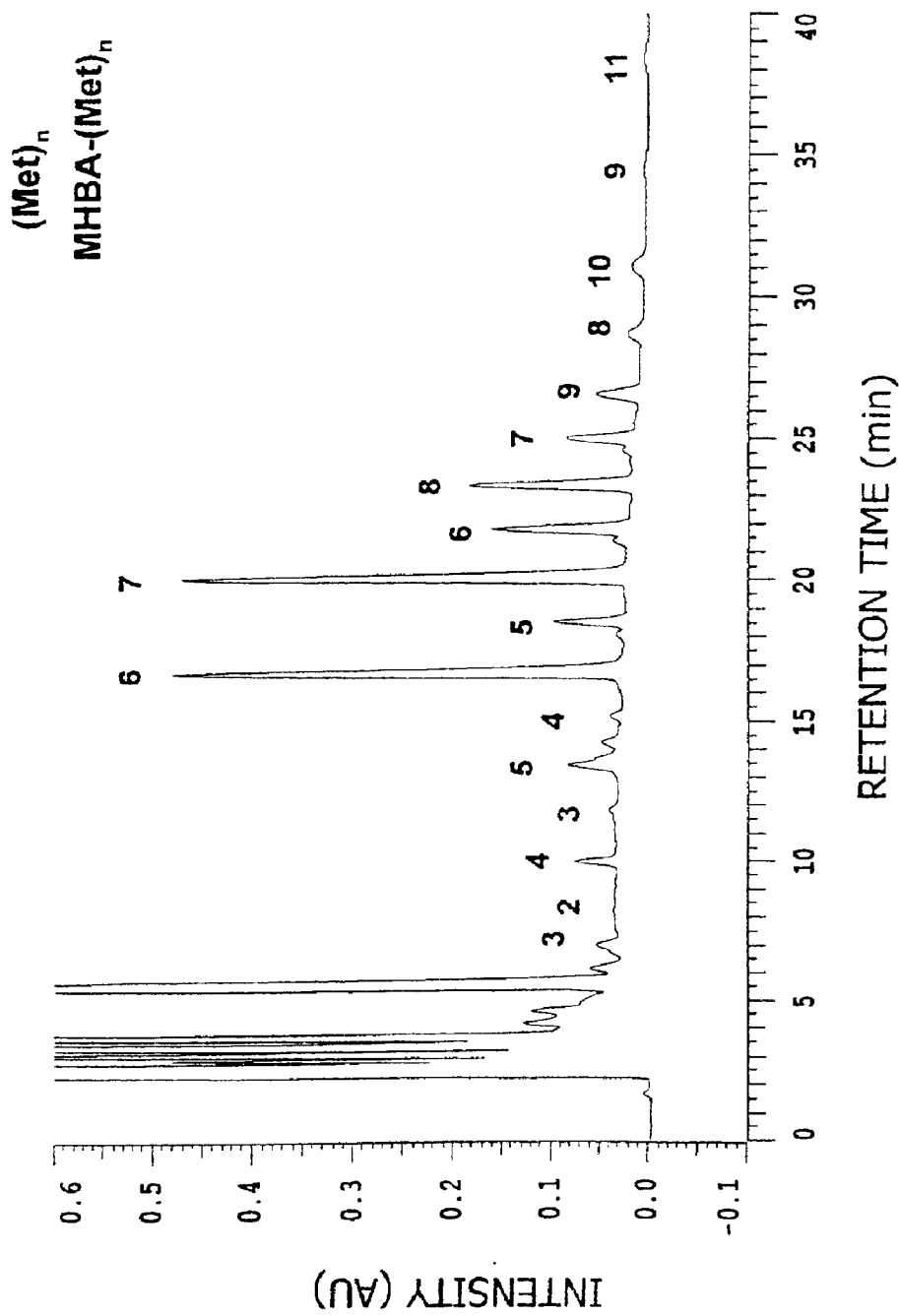
FIG. 4 is a HPLC graph of HMB-methionine sulfone co-oligomers after a incubation period of 10 minutes.
Figure 5:
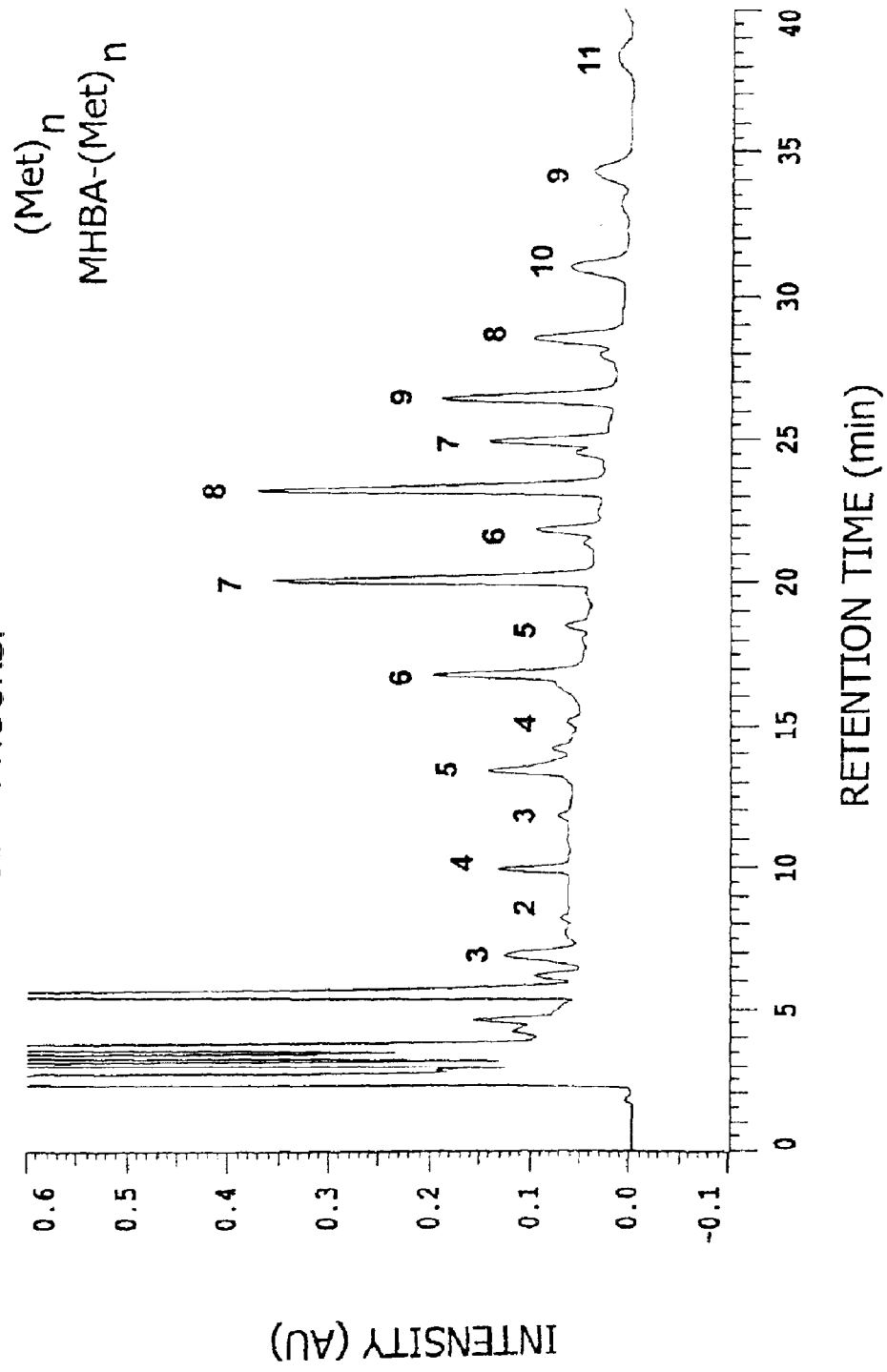
FIG. 5 is a HPLC graph of HMB-methionine sulfone co-oligomers after a incubation period of 24 hours.
Figure 6:
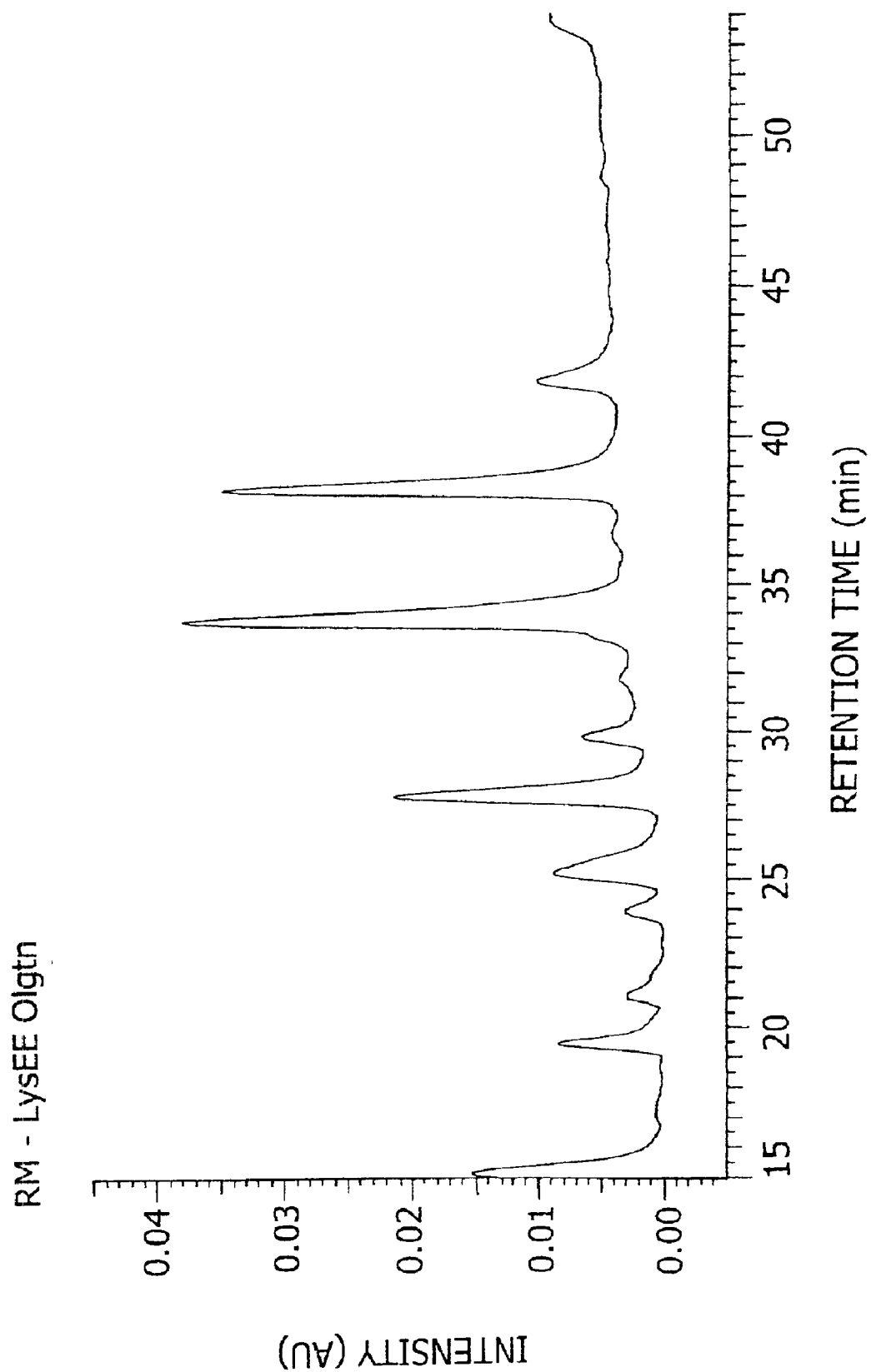
FIG. 6 is a ion-pair liquid chromatography and MALDI-TOF mass spectrometry graph of lysine oligomers synthesized in a reverse micellar system.
Figure 7:
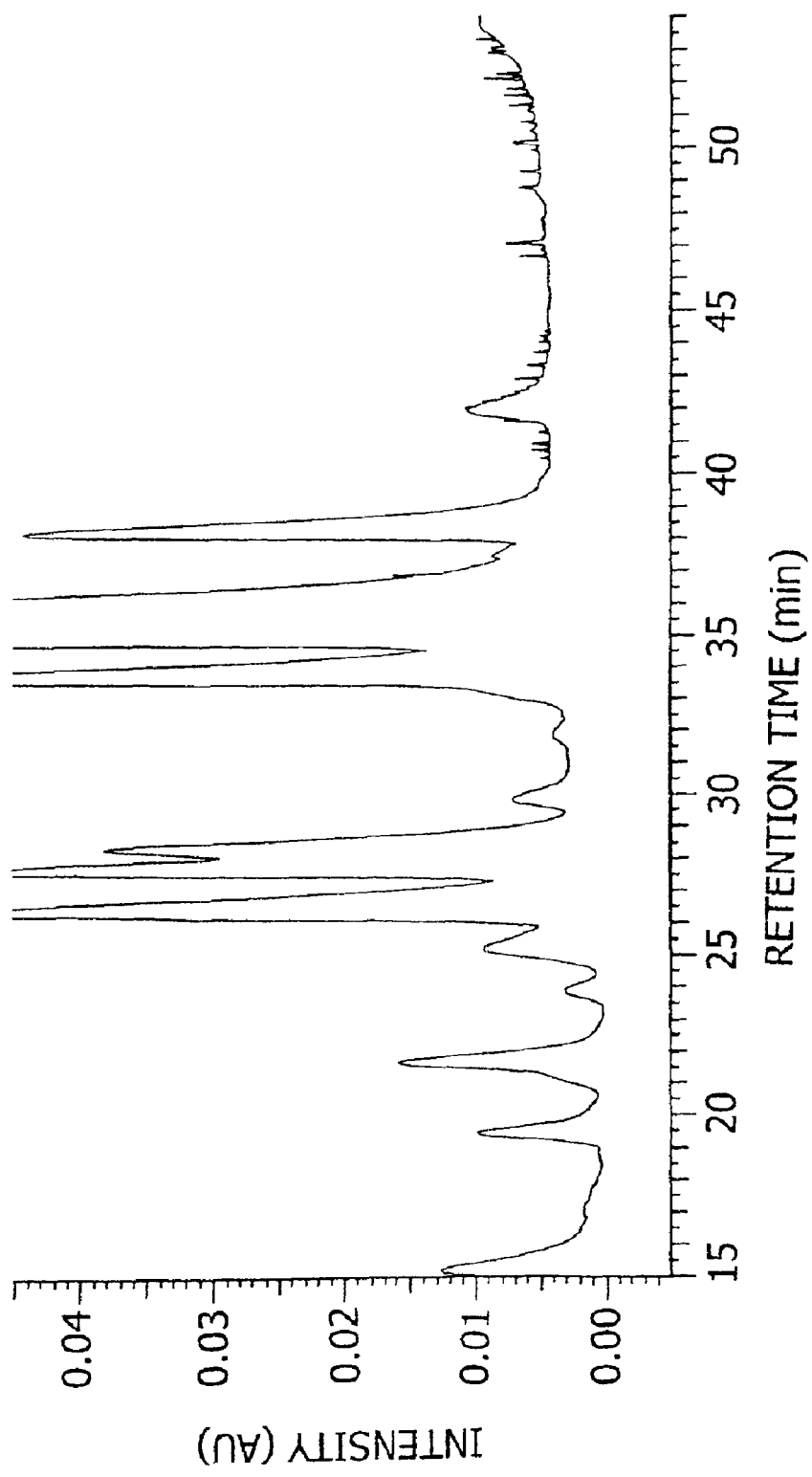
FIG. 7 is a ion-pair liquid chromatography and MALDI-TOF mass spectrometry graph of HMB-lysine co-oligomers synthesized in a reverse micellar system.
Figure 8:
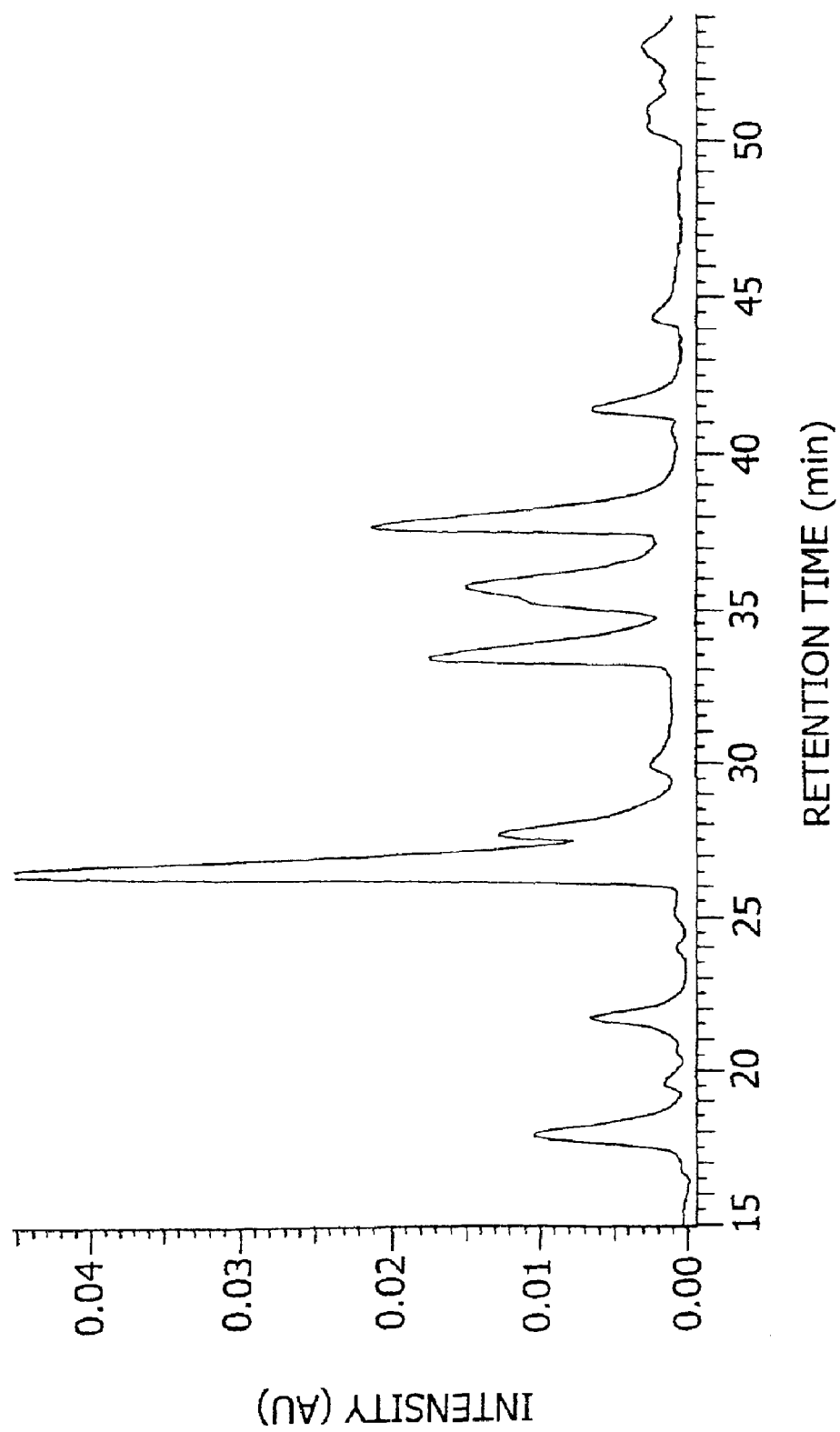
FIG. 8 is a ion-pair liquid chromatography and MALDI-TOF mass spectrometry graph of HMB-lysine co-oligomers synthesized in a 2-phase system.
Figure 9:
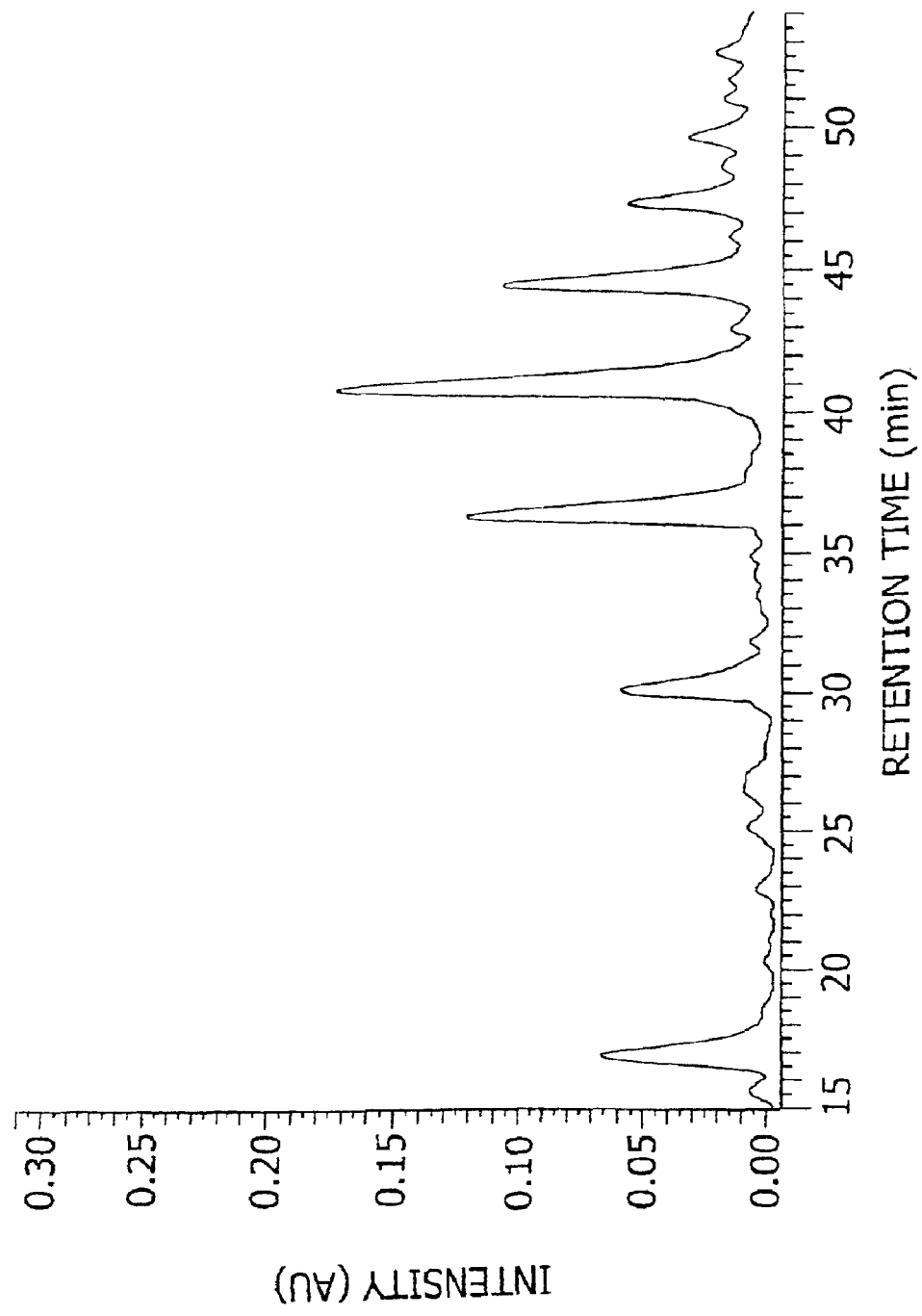
FIG. 9 is a ion-pair liquid chromatography and MALDI-TOF mass spectrometry graph of lysine oligomers synthesized in a 2-phase system.
Figure 10:
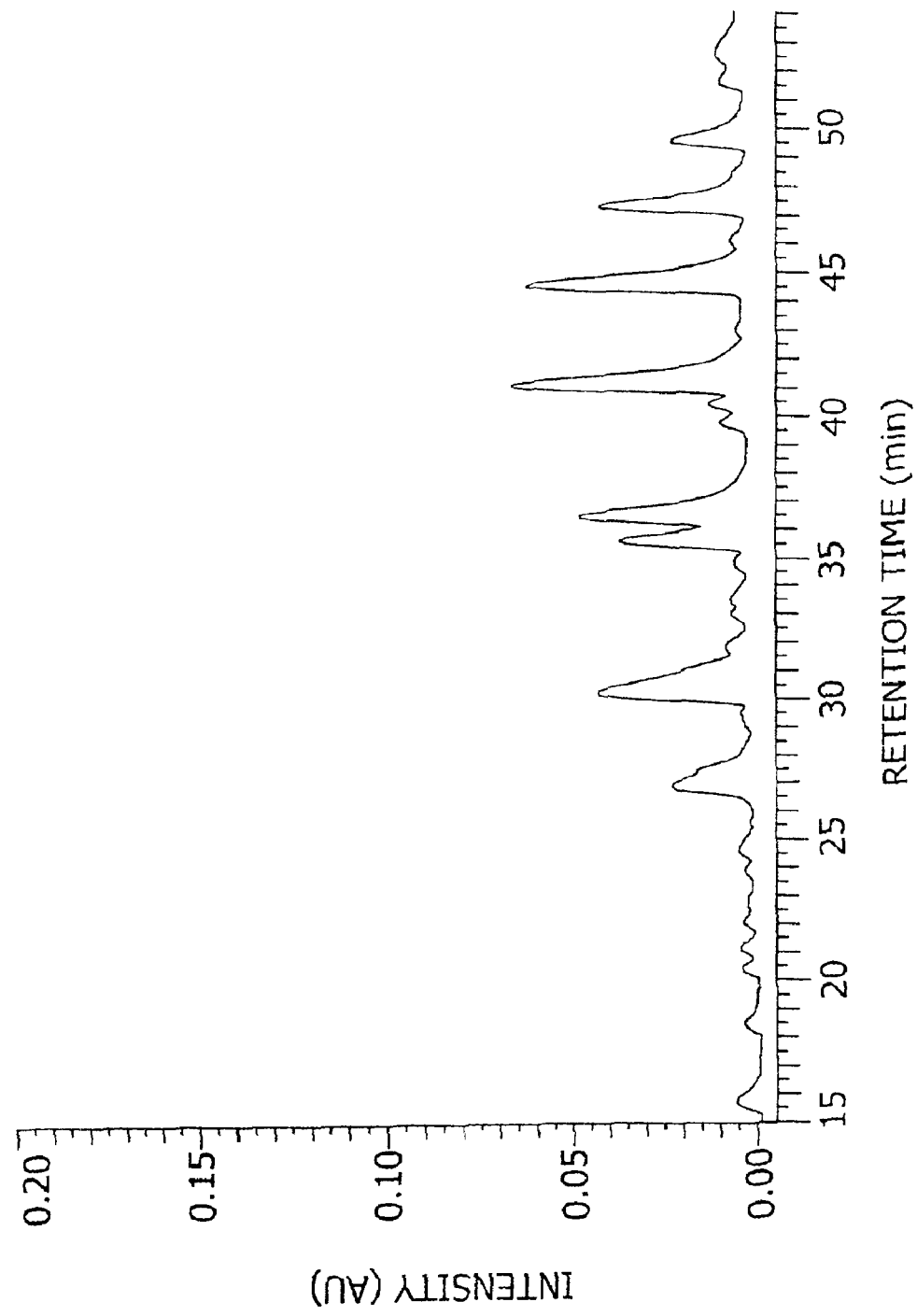
FIG. 10 is a ion-pair liquid chromatography and MALDI-TOF mass spectrometry graph of lysine oligomers synthesized in a 3-phase system.
Figure 11:
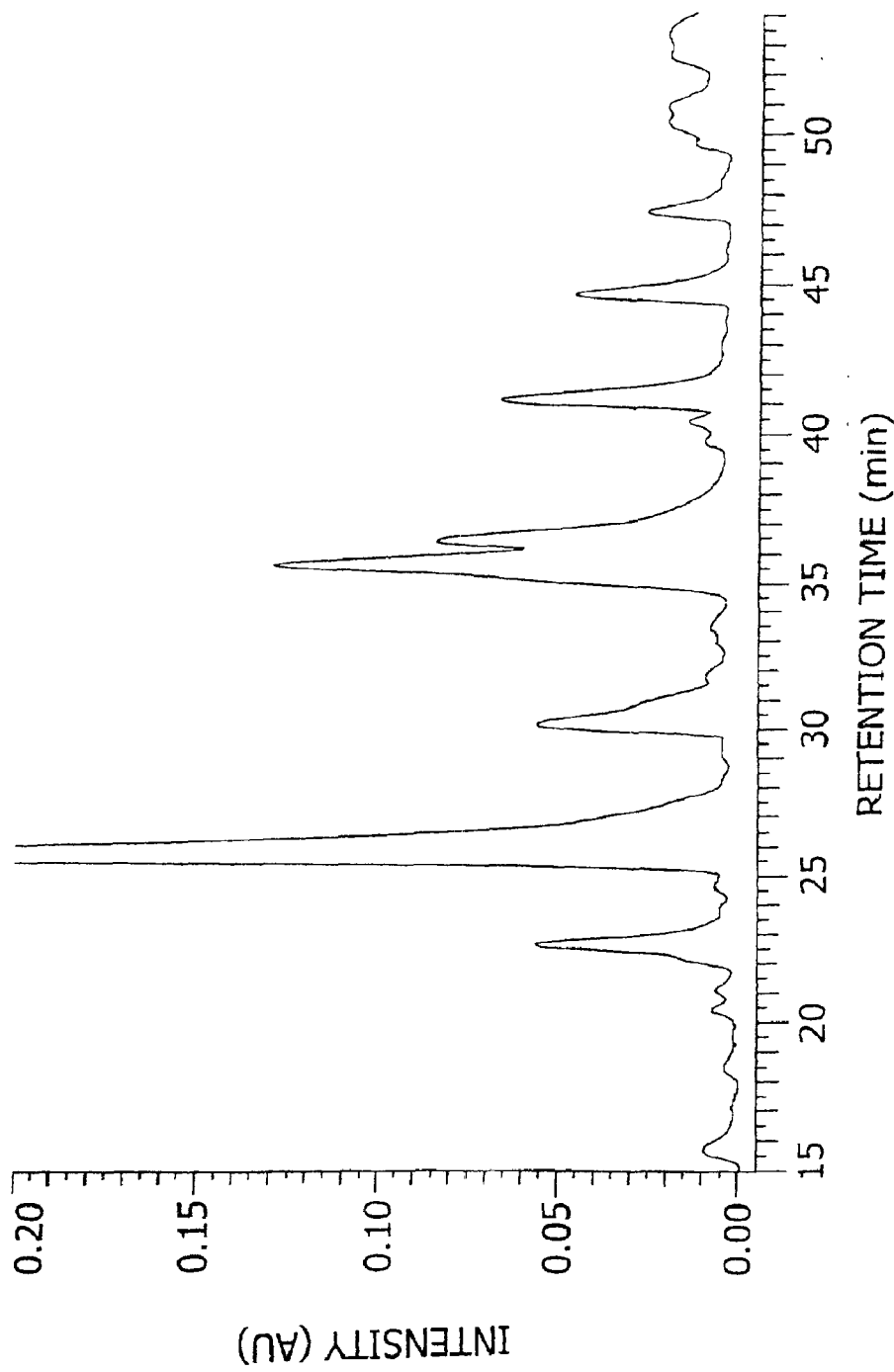
FIG. 11 is a ion-pair liquid chromatography and MALDI-TOF mass spectrometry graph of HMB-lysine co-oligomers synthesized in a 3-phase system.
Figure 12:
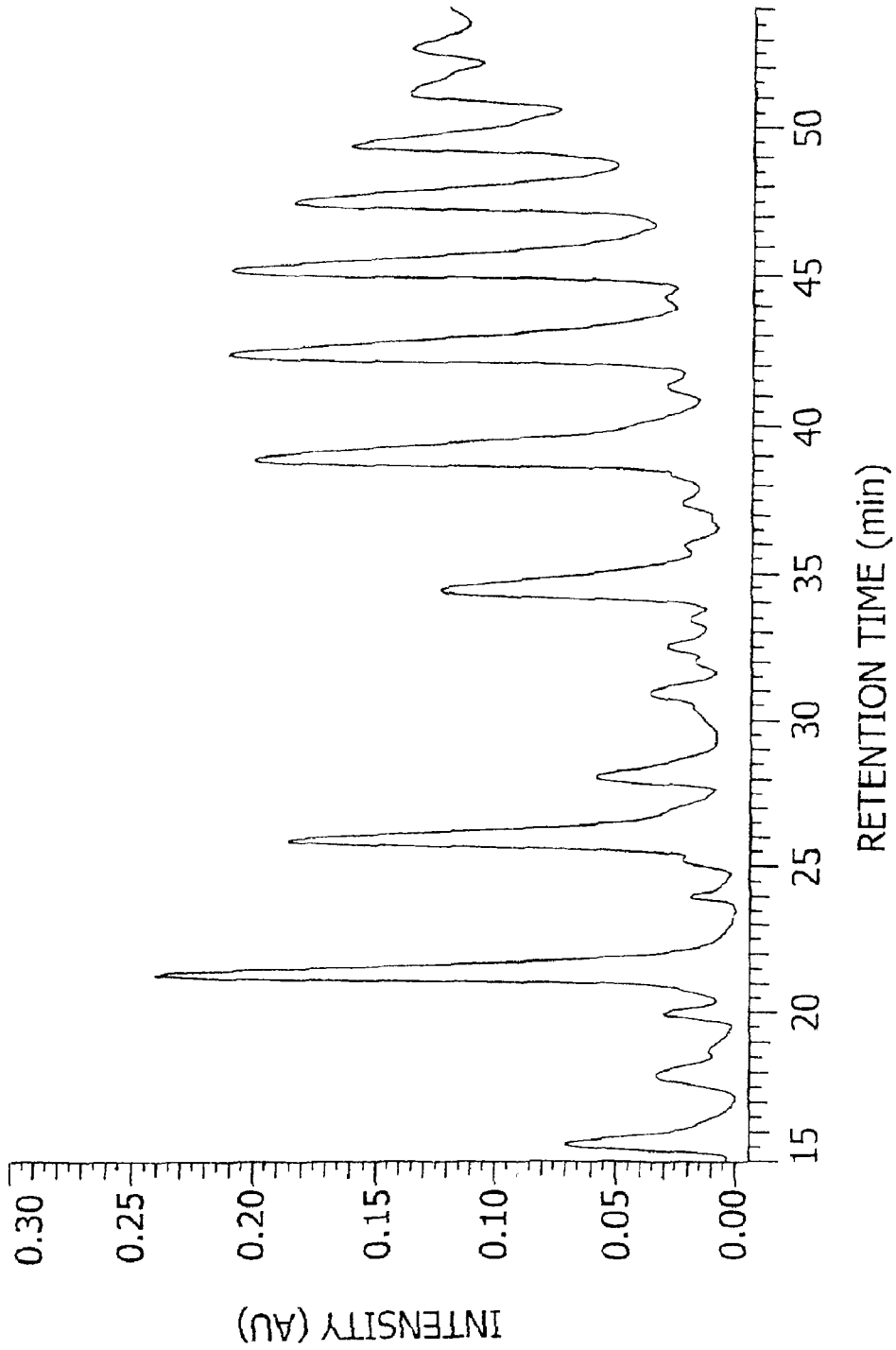
FIG. 12 is a ion-pair liquid chromatography and MALDI-TOF mass spectrometry graph of lysine oligomers synthesized in a reduced volume 2-phase system.
Figure 13:
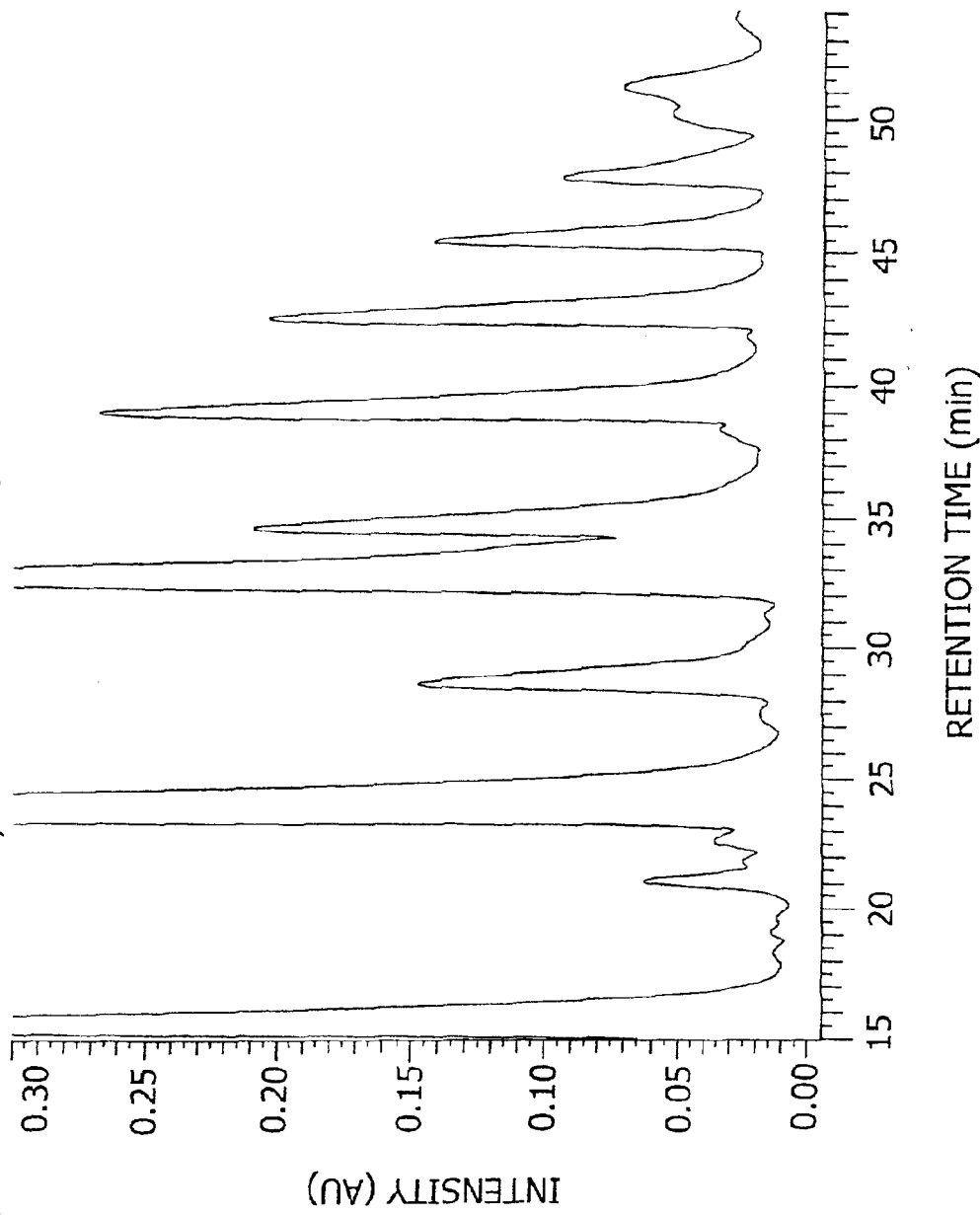
FIG. 13 is a ion-pair liquid chromatography and MALDI-TOF mass spectrometry graph of HMB-lysine co-oligomers synthesized in a reduced volume 2-phase system.

The chromatographic separation of HMB-poly-methionine sulfones is shown in FIG. 4. This chromatogram contained a number of peaks, which were not present in the poly methionine sulfone chromatogram. This indicates that HMB is incorporated in the $(Met)^n$ oligomer. The incorporation most likely occurs at the N-terminal end. The resulting $HMB\text{-}(Met)^n$ co-oligomers, with the terminal hydroxyl, should be less polar than the corresponding $(Met)^n$ oligomers with the terminal amine moiety. Therefore, the HMB containing co-oligomers should elute later than the corresponding Met oligomers and this appears to be the case. The elution times for methionine sulfones and HMB methionine sulfones are given in Table 1. The chromatographic separations of methionine oligomer (sulfones) obtained after different incubation periods indicate that the relative abundance of methionine oligomers is dependent on the incubation period. The abundance of longer chain co-oligomers was higher in co-oligomers obtained after 24 hours incubation (FIG. 5) relative to the co-oligomers obtained after 10 minutes incubation (FIG. 4). It can be readily observed that the concentrations of longer chain co-oligomers increased with an increase in the incubation period. Chromatographic results also indicate that presence of HMB may affect the relative distribution of methionine oligomers. These results are significant in light of the reports in the literature, which suggest that the uptake of methionine oligomers is dependent on the size of the oligomers.

TABLE 1

Elution Times of Met Oligomer and HMB-Met Co-Oligomer Sulfones

| Oligomer | Elution Time (mins) Present Study | Elution Time (mins) Kasai et al. |
|---|---|---|
| $(Met)_4$ | 10.0 | NR |
| $HMB\text{-}(Met)_3$ | 11.8 | NA |
| $(Met)_5$ | 13.4 | 14.0 |
| $HMB\text{-}(Met)_4$ | 15.1 | NA |
| $(Met)_6$ | 16.8 | 17.8 |
| $HMB\text{-}(Met)_5$ | 18.5 | NA |
| $(Met)_7$ | 20.1 | 21.0 |
| $HMB\text{-}(Met)_6$ | 21.8 | NA |
| $(Met)_8$ | 23.3 | 24.0 |
| $HMB\text{-}(Met)_7$ | 24.9 | NA |
| $(Met)_9$ | 26.5 | 26.9 |
| $HMB\text{-}(Met)_8$ | 28.6 | NA |
| $(Met)_{10}$ | 31.1 | 29.5 |
| $HMB\text{-}(Met)_9$ | 34.2 | NA |

NR: Not Reported
NA: Not Available

Example 2

Oligomerization and Co-Oligomerization of Lysine and HMB

This example demonstrates four alternative procedures for the enzymatic synthesis of oligomers comprising lysine and co-oligomers comprising HMB-lysine. The experiment was designed to compare three novel synthesis procedures to that of Puigserver et. al.[1] who reported a procedure for papain catalyzed polymerization of lysine.

In general, protease-catalyzed synthesis of water insoluble amino acid oligomers in aqueous media is driven by precipitation. The synthesis of water soluble oligomers of amino acids, such as lysine can be controlled only in mixed phase systems where the equilibria is shifted in favor of the synthesis of polypeptides due to enhanced partitioning of peptide in the organic phase. Puigserver et. al. reported a procedure for papain catalyzed polymerization of lysine which involved the binding of papain to modified PEG (MW 2000 or 5000). The bound enzyme was then used to synthesize poly lysine in a two phase reaction mixture. The following summarizes the experiment to use Puigserver's method to explore the feasibility of the co-oligomerization of lysine and HMB in comparison to three novel synthesis methods.

PEG bound Papain system (Puigserver's Method): 10 mM of substrate was added to 98 mL of toluene along with 0.8 mL of Diisopropyl amino ethyl and 0.2 mL of mercaptoethanol, followed by 17 mM of $PEG_{2000}$ modified Papain. The mixture was allowed to incubate for 24 hours, before being evaporated and redissolved in deionized water and analyzed on a ion-pair liquid chromatography column.

Two Phase Toluene:Water System: This solvent system was evaluated with varied phase ratios, two of which are described below:
a) 10 mM of substrate was added to 98 mL of toluene along with 0.8 mL of Diisopropyl amino ethyl and 0.2 mL of mercaptoethanol, followed by 1 mL of aqueous papain suspension. The mixture was allowed to incubate for 24 hours, before being evaporated and redissolved in DI water and analyzed on a ion-pair liquid chromatography column.
b) 100 mM of substrate was added to 8.9 mL of toluene along with 0.08 mL of Diisopropyl amino ethyl and 0.02 mL of mercaptoethanol. This was followed by 1 mL of aqueous papain suspension, which resulted in a two phase system. The mixture was allowed to incubate for 24 hours, before being evaporated and redissolved in DI water and analyzed on an ion-pair liquid chromatography column.

Reverse Micellar System: 10 mM of substrate was dissolved in 98 mL of a reverse micellar solution containing 150 mM of AOT (3.33 g), 0.8 mL of diisopropyl amino ethyl and 0.2 mL of mercaptoethanol in isooctane. 1 mL of aqueous papain solution was added to the mixture and allowed to incubate for 24 hours, at the end of which the mixture was heated to denature the enzyme and the oligomeric and co-oligomeric products extracted with 1 M NaCl solution. The solution was later analyzed on a ion-pair liquid chromatography column.

Three Phase DFP:Octane:Water System: To a two phase system comprising of 4.45 mL of DFP and 4.45 mL of octane was added 100 mM of substrate along with 0.08 mL of Diisopropyl amino ethyl and 0.02 mL of mercaptoethanol. The addition of 1 mL of aqueous papain suspension which is insoluble in either of the phases converts this system to a three phase system. The mixture was allowed to incubate for 24 hours, before being evaporated and redissolved in DI water and analyzed on a ion-pair liquid chromatography column Results: The yield and the degree of oligomerization and co-oligomerization were determined with ion-pair liquid chromatography and MALDI-TOF mass spectrometry. These results appear in FIGS. 6 to 13. In general, Puigserver's method was found to be cumbersome and did not yield any discernable HMB-lysine co-oligomers. Reaction conditions and results are further summarized in Table 2.

TABLE 2

Procedure for the various methods used to synthesize lysine oligomers and HMB-lysine co-oligomers

| Components | Lysine Oligomerization | | | | | HMB-lysine Co-oligomerization | | | | |
|---|---|---|---|---|---|---|---|---|---|---|
| | Pgsr[f] | 2-f[g] | RM[h] | 3-f[i] | RV 2-f[j] | Pgsr[f] | 2-f[g] | RM[h] | 3-f[i] | RV 2-f[j] |
| LysEE.2HCl (mM) | 10 | 10 | 10 | 100 | 100 | 5 | 10 | 10 | 50 | 50 |
| HMB analog mM | | | | | | 5 | 10 | 10 | 50 | 50 |
| i-$Pr_2NH_2Et$ (% v/v)[a] | 0.8 | 0.8 | 0.8 | 0.8 | 0.8 | 0.8 | 0.8 | 0.8 | 0.8 | 0.8 |
| $SCH_2CH_2OH$ (% v/v)[b] | 0.2 | 0.2 | 0.2 | 0.2 | 0.2 | 0.2 | 0.2 | 0.2 | 0.2 | 0.2 |
| Papain (% v/v)[c] | | 1 | 1 | 10 | 10 | | 1 | 1 | 10 | 10 |
| Toluene (% v/v) | 98 | 98 | | | 89 | 98 | 98 | | 0 | 89 |
| Isooctane (% v/v) | | | 98 | | | | | 98 | | |
| DFP (% v/v)[d] | | | | 44.5 | | | | | 44.5 | |
| Octane (% v/v) | | | | 44.5 | | | | | 44.5 | |
| AOT (mM)[e] | | | 150 | | | | | 150 | | |
| PEG-Papain (mM) | 17 | | | | | 17 | | | | |
| Yields (%) | 0 | 17 | 22 | 95 | 90 | 0 | 17 | 22 | 95 | 90 |

[a]Di-isopropyl amino ethyl
[b]Mercaptoethanol
[c]Aqueous suspension of papain obtained from Sigma
[d]Decafluoropentane
[e]Aerosol-OT, Dioctyl sulfor succinate
[f]Puigserver's method
[g]Two-phase method
[i]Three Phase Method
[h]Reverse Micellar method
[i]Three Phase method
[j]Reduced volume (10%) m
[1]Anne Frejancic, Antoine Puigserver and Hubert Gaertner, Papain-Catalyzed Polymerization of Amino Acids in Low Water Organic Solvents, Biotech. Lett., 1991, 13 (3), 161–166.

Example 3

HMB-methionine and HMB-lysine co-polymers were synthesized enzymatically through a papain-catalyzed reaction along with poly-methionine and poly-lysine (as controls) as described in Examples 1 and 2. The biological release of the amino acids from the oligomers was examined using several digestive enzymes including pepsin, trypsin, chymotrypsin, intestinal peptidase and carboxypeptidase. The oligomers were dissolved at 10 mg/mL in 0.15 HCl (pH 2.5) or 50 mM $KPO_4$ (pH 7.5). Samples (0.5 mL) were incubated with 10 units of each enzyme for 2 hours at 37° C. The extent of digestion was quantified by measurement of newly released amino groups and their reaction with o-Phthalaldehyde (OPA) and 2,4,6-trinitrobenzene sulfonic acid (TNBSA). Acid hydrolysis was prepared by complete hydrolysis of 10 mg/mL polymers in 6 M HCl for 24 hours at 110° C. Results are summarized below in Table 3.

Results show that HMB-methionine and HMB-lysine can be hydrolyzed by strong acid and heat. HMB-met is digested only 3.5% by pepsin and not at all by the other proteases. Poly-lysine can be digested by intestinal peptidase (20% in 2 hours at 37° C.) but not by other proteases. HMB-lysine is not digested by any of the proteases tested. In conclusion, these data suggest the lack of enzymatic digestion of HMB-met and HMB-lysine co-oligomer was caused by a structural difference instead of solubility of the co-oligomers.

TABLE 3

ENZYMATIC DIGESTION OF AMINO ACID POLYMERS

| Enzyme | Poly-Lys (~8mer) | HMB-met | Poly-met | HMB-Lys | Poly-Lys (~4mer) |
|---|---|---|---|---|---|
| pepsin | 0 | 0.030 (3%) | 0.062 (15%) | 0 | 0 |
| trypsin | 0.008 (15%) | 0 | 0 | 0 | 0 |
| chymotrypsin | 0 | 0 | 0 | 0 | 0 |
| intestinal peptidase | 0.013 (25%) | 0 | 0.052 (13%) | 0 | (TNBSA, ~20%) |
| carboxy-peptidase A | 0 | 0 | 0 | 0 | 0 |
| acid hydrolysis (-initial value) | 0.052 | 0.868 | 0.406 | 0.063 | 0.093 |

Figure 14A:
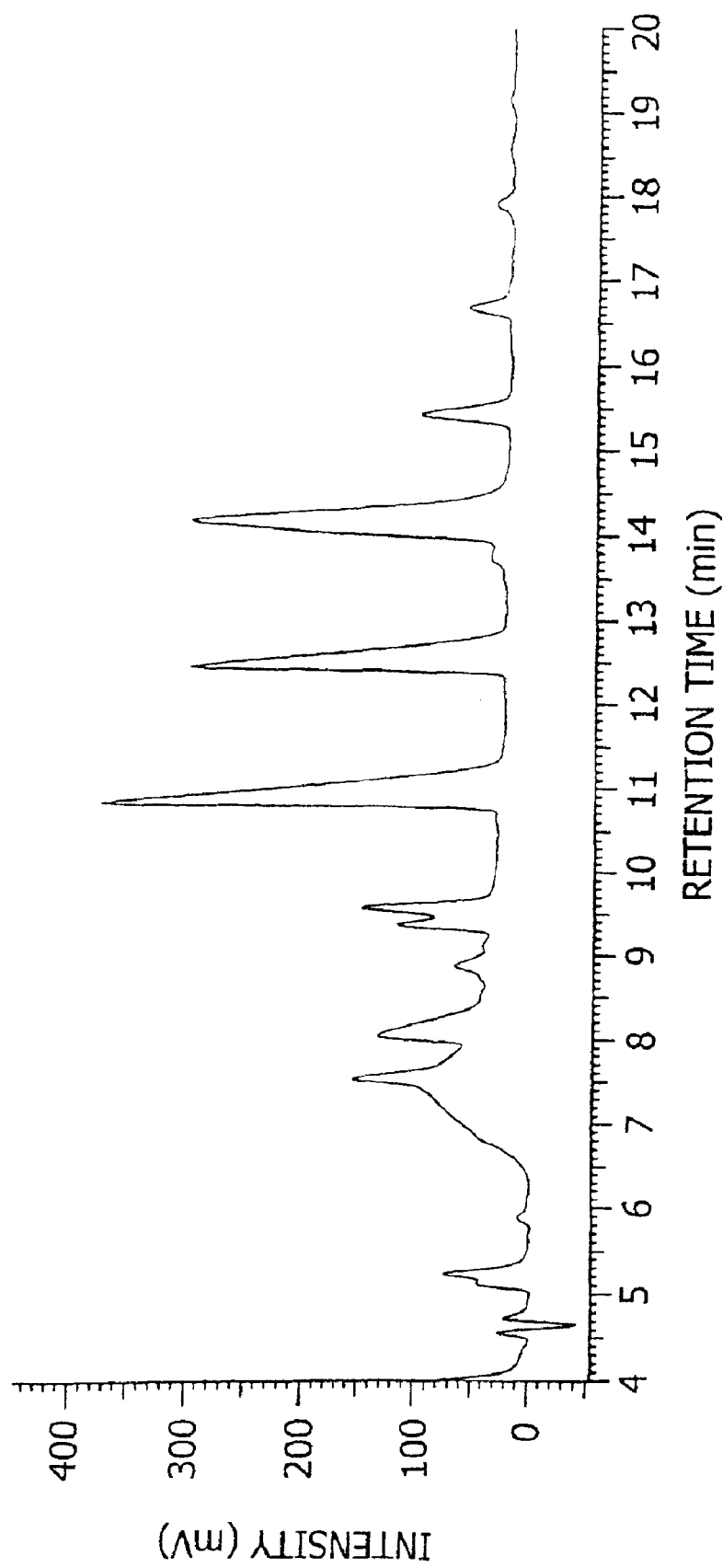
FIG. 14A is a chromatogram of persulfonated methionine oligomers using a UV absorption detector.
Figure 16:
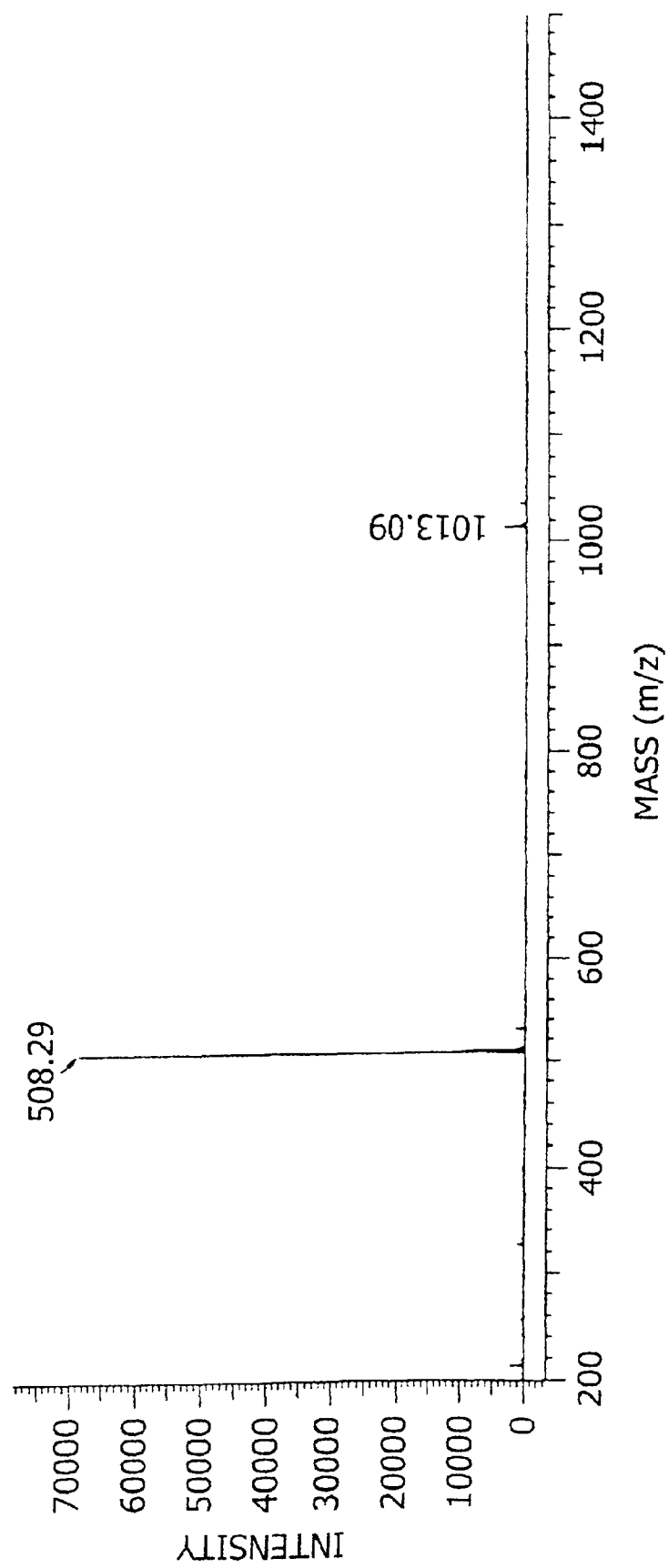
FIG. 16 is a positive ion ESI spectra of $(Met)_3$ sulfone peak eluting at 5.27 minutes.
Figure 17:
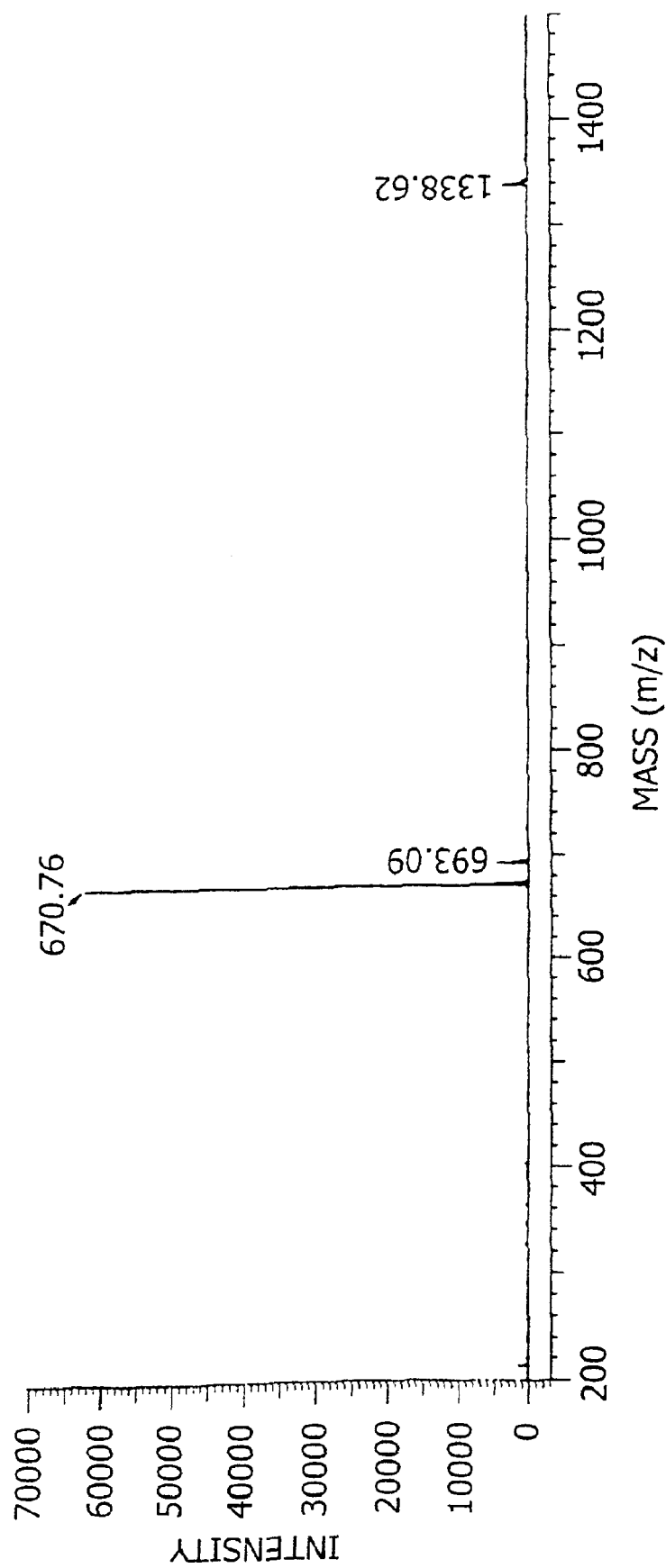
FIG. 17 is a positive ion ESI spectra of $(Met)_4$ sulfone peak eluting at 7.70 minutes.
Figure 18:
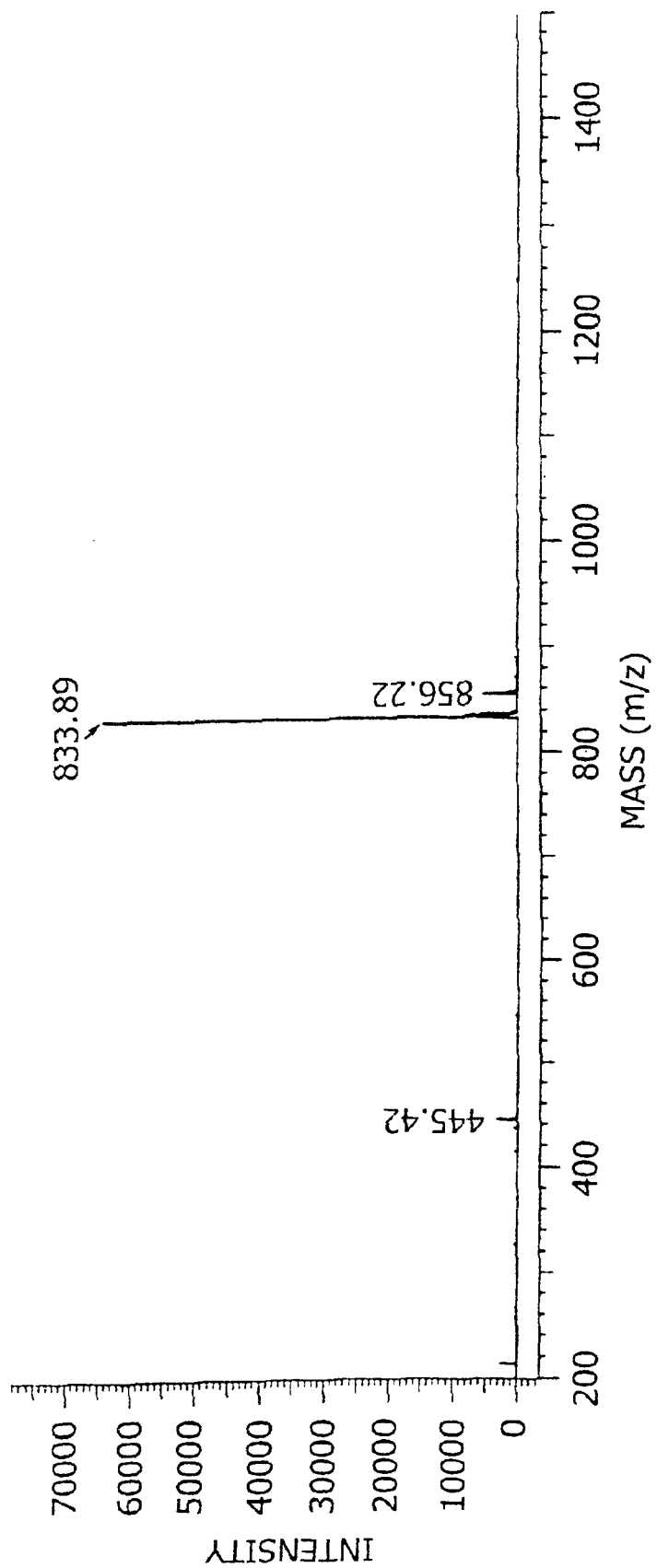
FIG. 18 is a positive ion ESI spectra of $(Met)_5$ sulfone peak eluting at 9.47 minutes.
Figure 19:
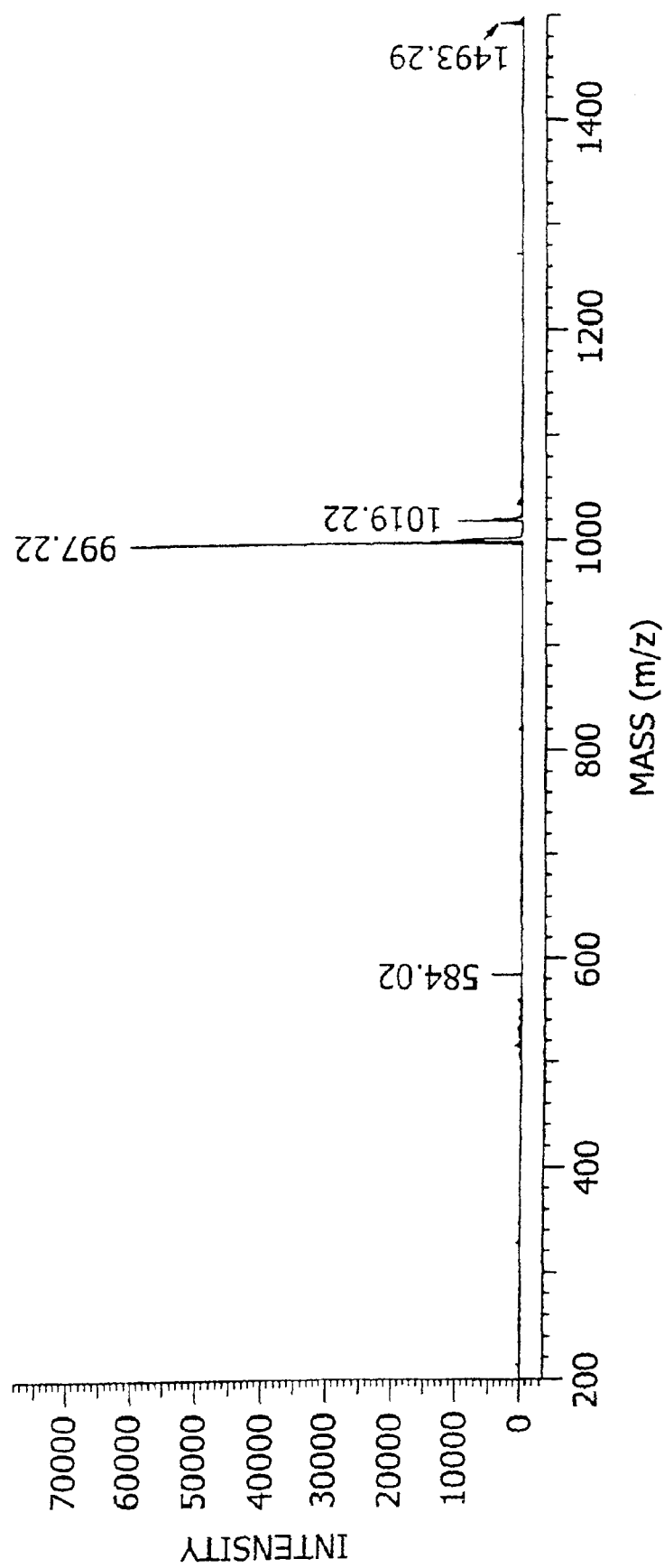
FIG. 19 is a positive ion ESI spectra of $(Met)_6$ sulfone peak eluting at 11.09 minutes.
Figure 20A:
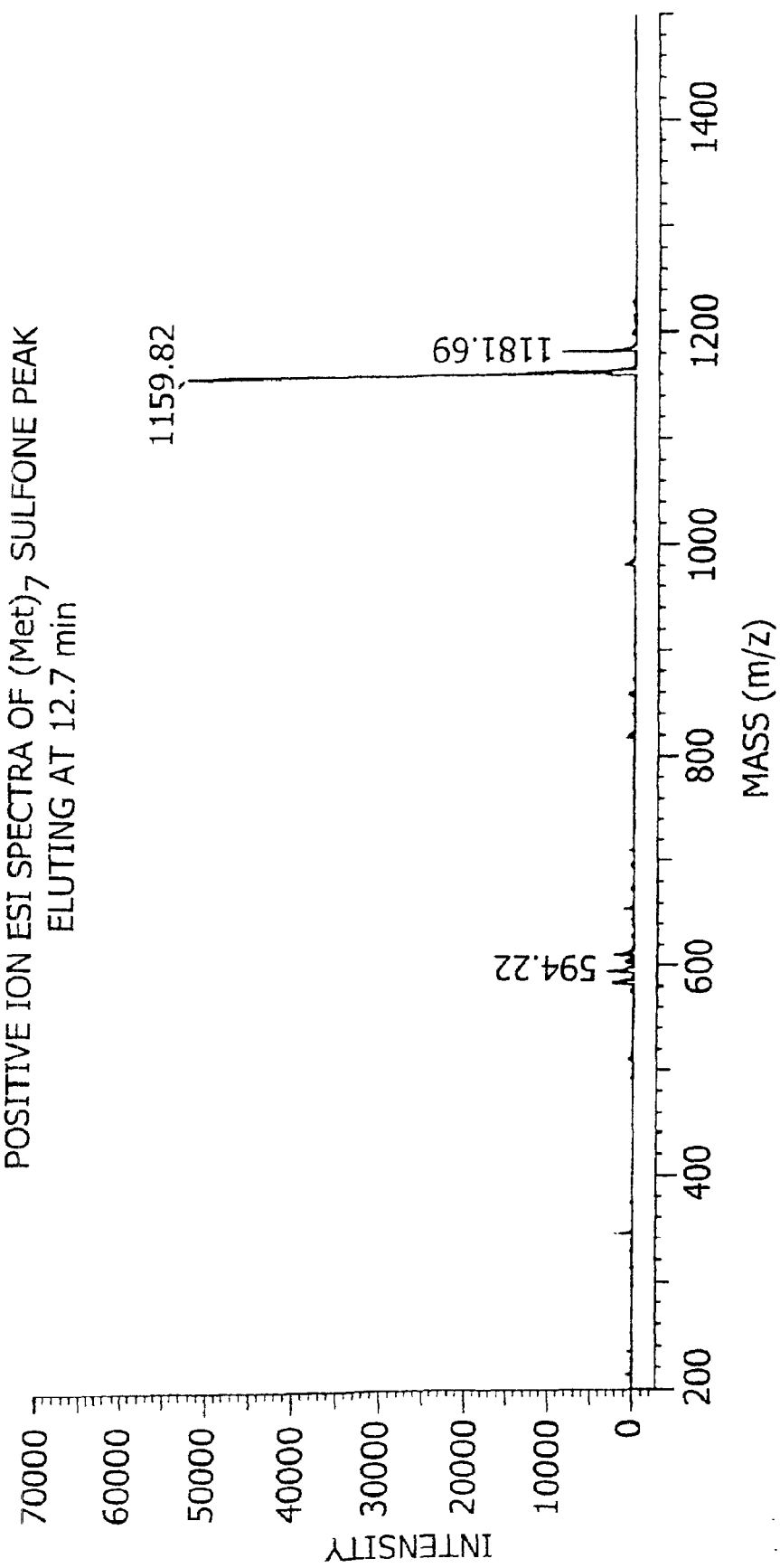
FIG. 20A is a positive ion ESI spectra of $(Met)_7$ sulfone peak eluting at 12.7 minutes.

Readings were from OPA analysis of 20 μg samples
Hydrolysis was done at 37° C. for 2 hours
(%) refers to % of acid hydrolysis number Example 4
Characterization of Methionine Oligomers and HMB-Methionine Co-oligomers Met oligomers and HMB-Met co-oligomers produced through papain mediated enzymatic reactions at pH 5.5 and pH 9.0 according to the procedure described in Example 1 were subjected to persulfonation. Persulfone derivatives were separated with the reverse phase liquid chromatography (RPLC). The separated oligomers and co-oligomers were monitored with a UV absorption spectrophotometeric detector and an electrospray ionization interface (ESI) mass spectrometer. The absorption wavelength was set at 210 nm. The mass spectrometer was operated in positive and negative ion modes. The outputs of the UV absorption detector and the positive ion ESI-MS are shown in FIGS. 14 and 15.

The chromatogram of (Met)n persulfones obtained with the UV detector and the positive ion total ion chromatogram (TIC) were similar to the chromatograms obtained from earlier with a earlier experiments using a RPLC-Diode Array Detector (DAD) system. These results had indicated the formation of Met homo-oligopeptides and HMB-Met co-oligomers. The results were supported by data obtained from the matrix assisted laser desorption ionization-mass spectrometry (MALDI-MS) experiments.

The experiments with ESI-MS in the positive ion mode confirmed the formation of methionine oligomers. The ESI-MS spectrum for individual LC peaks provides conclusive evidence for the formation of (Met) to (Met) oligomers. The mass difference between in the molecular masses of successive oligomers was found to be 163, which corresponds to the sulfonated methionine residue.

Spectra corresponding to different peaks are shown in FIGS. 16–20. The general formula for the separated oligomers is:

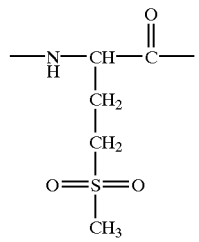

The positive ion TIC of HMB-(Met)n co-oligomers obtained with ESI-MS did not contain extra peaks observed in the LC-UV chromatogram. The spectra of individual peaks in the HMB-Met co-oligomers did not provide any evidence for HMB-(Met)n co-oligomers formation. These results were not unexpected, the lack of pseudo-molecular positive ions in the MALDI-TOF spectra of HMB-(Met)n in the earlier experiments had led us to the conclusion that HMB is attached at the N-terminal end of the polymethionine chain. The lack of protonated ions in the HMB-Met co-oligomers is the result the weak proton affinity of the terminal hydroxyl group.

The confirmation of the HMB-(Met)n was obtained by monitoring negative ions formed through electron attachment to the (Met)n and HMB-(Met)n chains. The TIC of HMB-(Met)n in this case contained extra components (peaks) which corresponded to the extra peaks observed in the LC-UV chromatograms FIGS. 21 and 22.

Figure 24:
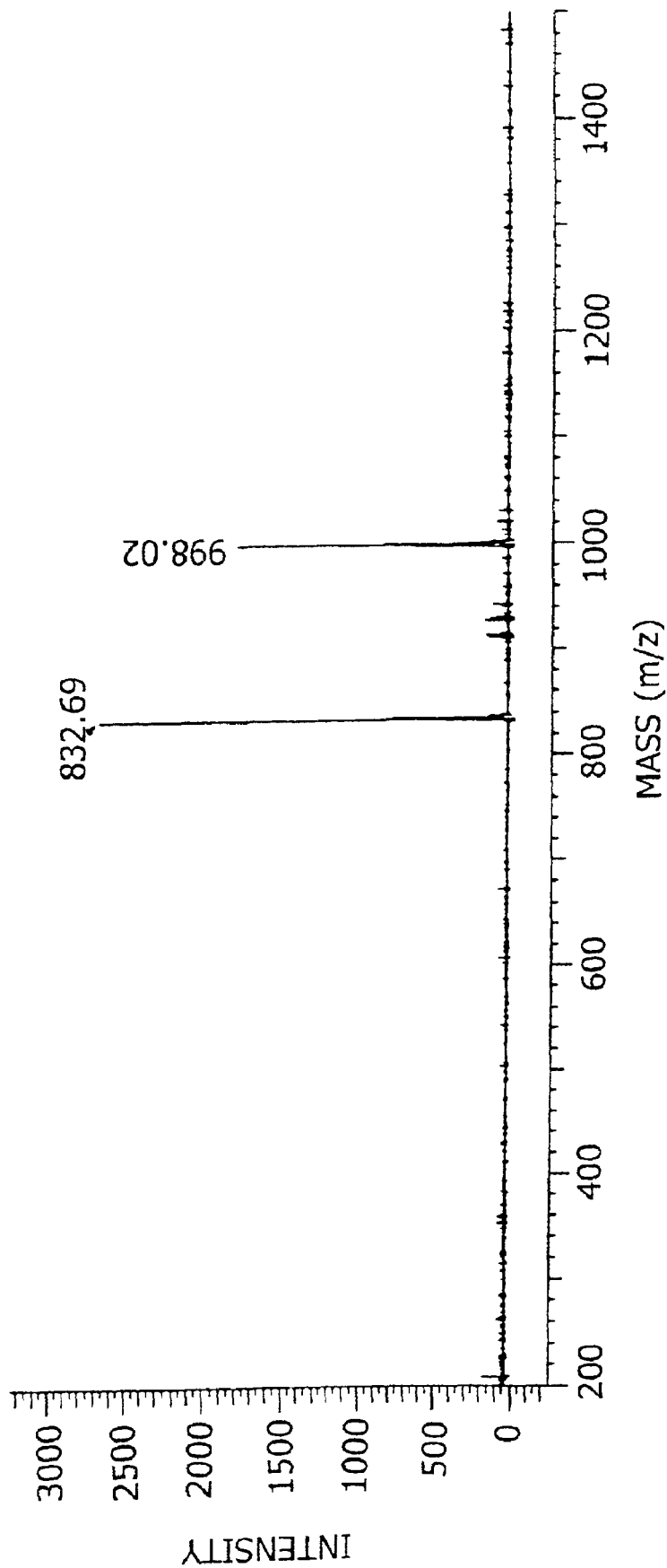
FIG. 24 is a negative ion ESI spectra of HMB-$(Met)_6$ sulfone peak eluting at 13.86 minutes.
Figure 25:
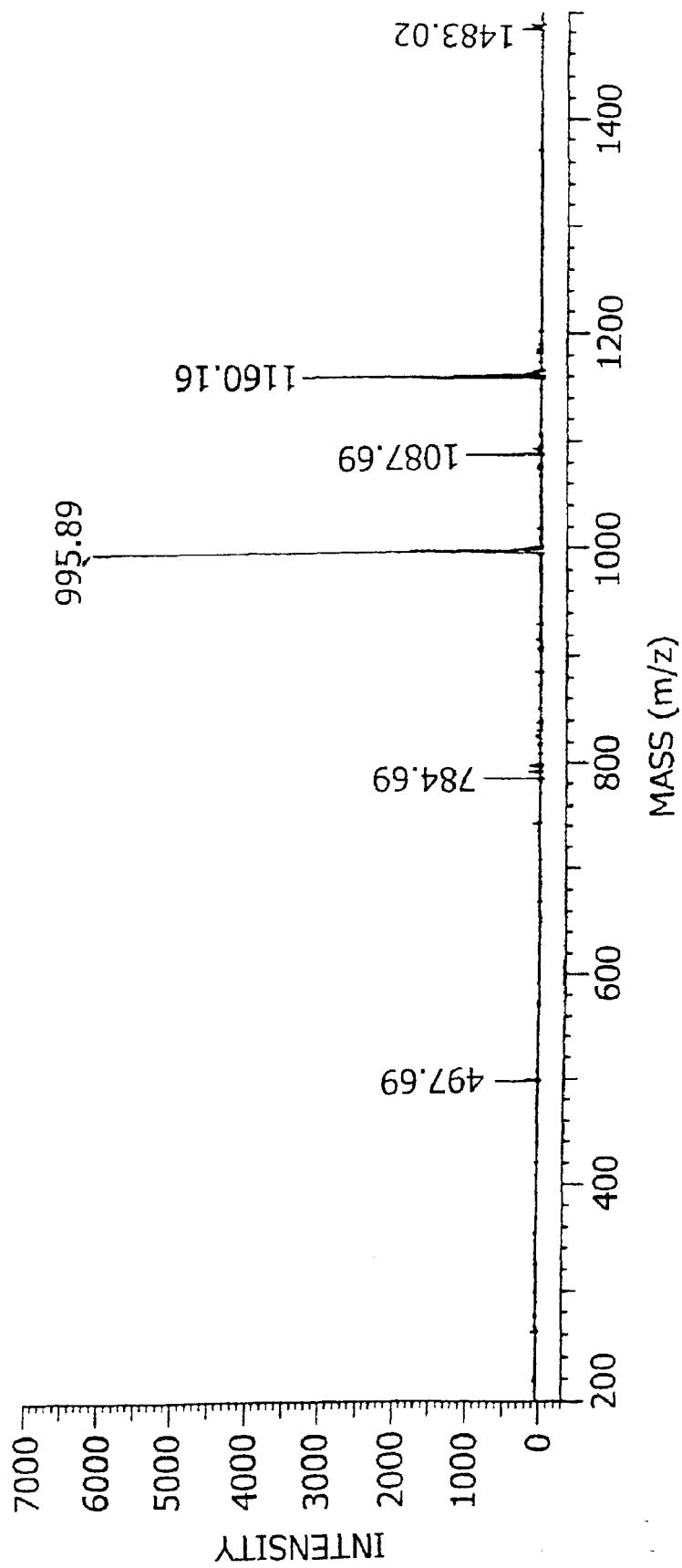
FIG. 25 is a negative ion ESI spectra of HMB-$(Met)_7$ sulfone peak eluting at 15.31 minutes.

A few representative spectra for the HMB-(Met)$_n$ peaks are shown in FIGS. 23–25. As expected, the molecular ions for HMB-(Met)n appear at one mass unit higher than the corresponding (Met)n ions. In addition, the retention times of HMB-(Met)n peaks are longer than the corresponding (Met)n peaks. This is to be expected since the terminal amine group of the (Met)n imparts higher polarity to methionine oligomers than the terminal hydroxyl to the HMB-(Met)n co-oligomers.

The presence of sulfonated methionine residue in both (Met)n oligomers and the HMB-(Met)n co-oligomers chains is again revealed by mass difference of 163 amu between the molecular masses of the separated chromatographic peaks. The mass difference corresponds to the mass of the methionine sulfone residue.

Figure 26:
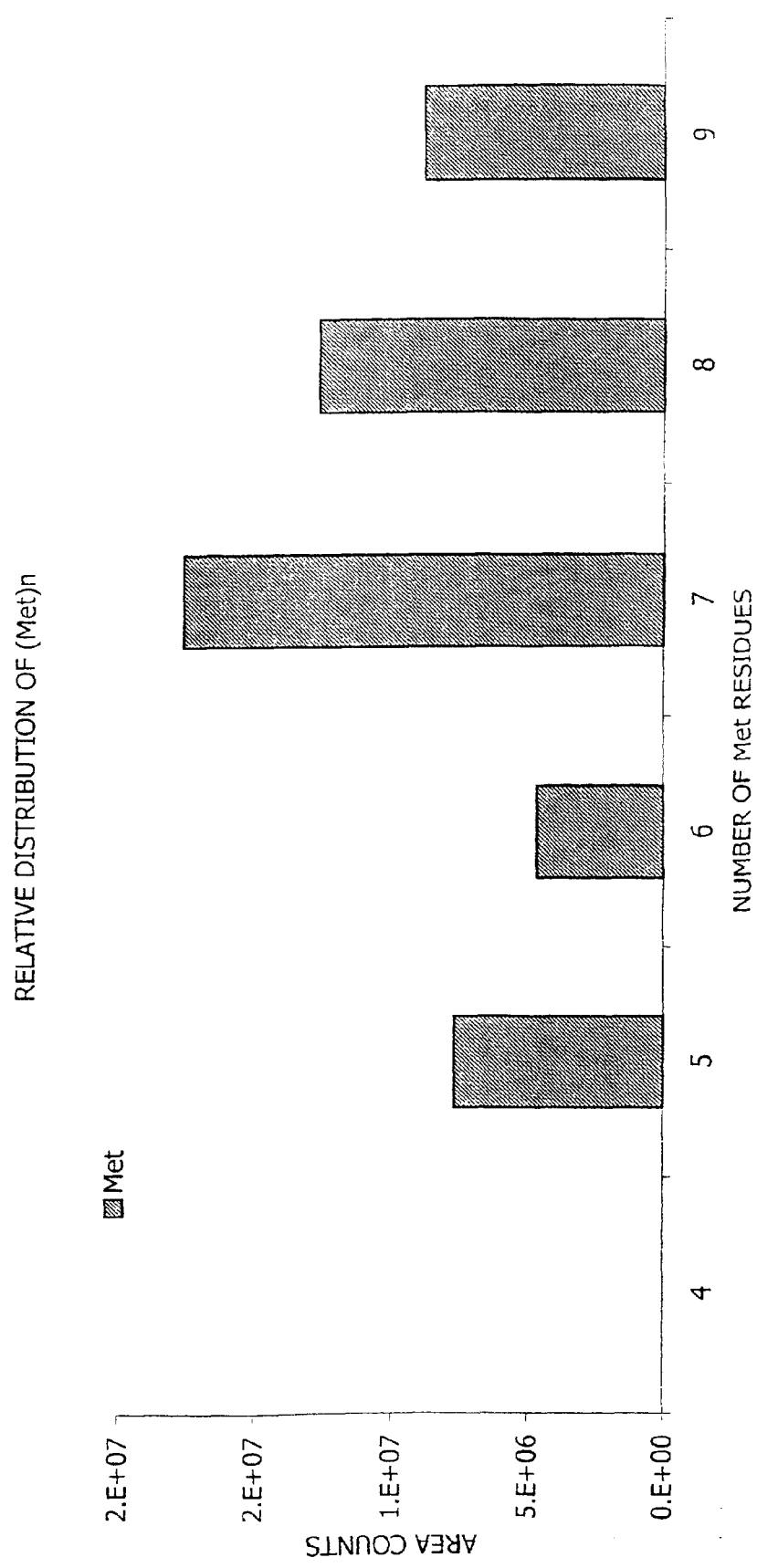
FIG. 26 is a bar graph of the relative distribution of $(Met)_n$ wherein n is the number of methionine residues in the methionine oligomers.
Figure 27:
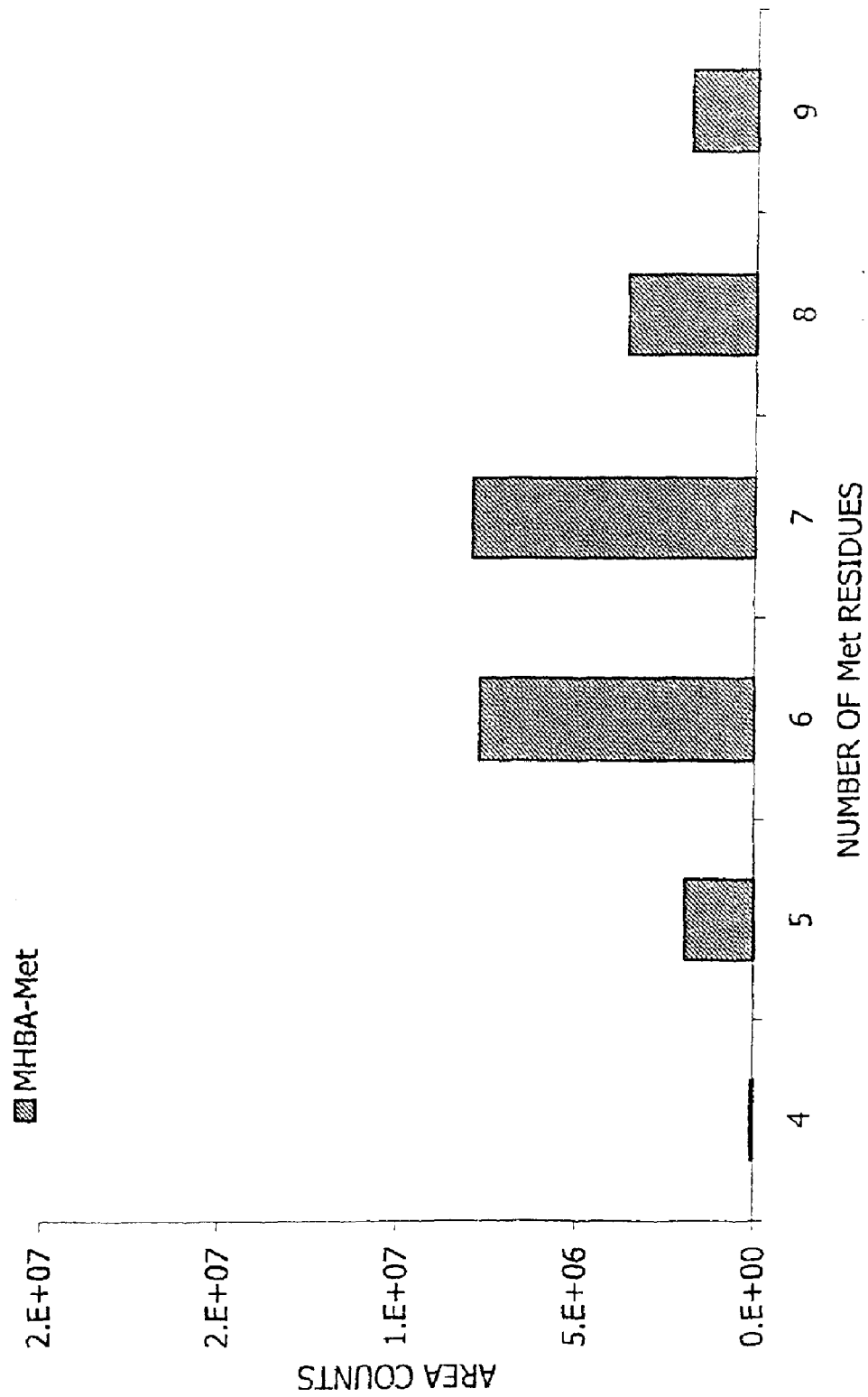
FIG. 27 is a bar graph of the relative distribution of HMB-$(Met)_n$ wherein n is the number of methionine residues in the HMB-methionine co-oligomers.

Both the positive ion and negative ion LC-ESIMS data show that the predominant (Met)n are composed of four to ten methionine residues. Likewise, the negative ion LC-ESI data shows that the predominant HMB-(Met)n co-oligomers contain one HMB residue and four to nine methionine residues. The relative distribution of (Met)n oligomers and HMB-(Met)n co-oligomers is presented in FIGS. 26 and 27.

Example 5
Synthesis of HMB-(Met)n Co-oligomers with HMB-methyl Ester and Met-ethyl Ester
ESI-MS Results Further experiments were conducted to confirm that HMB is attached at the N-terminal of the oligomers chain. In one such experiment methyl ester of HMB and ethyl ester of methionine were prepared. Equimolar amounts of mixed esters were subjected to papain mediated oligomerization and co-oligomerization at pH 5.5 with the procedure outlined in Example 1. The product was washed with water until it was free of monomers. The product was then freeze-dried, dissolved in DMSO and introduced in the MS through an ESI interface. The positive and negative ion spectra obtained for the mixed co-oligomers are shown in FIGS. 28A and 28B respectively.

The positive ion spectra (FIG. 28A) of shows two series of ions that are 28 mass units apart. One series containing ions m/z 674, 805, 936, 1067, 1198 and 1229 correspond to ((Met)$_n$+H$^+$) ions. The other series of ions which occur at m/z 702, 833, 964, 1095, 1226 and 1357 correspond to ((Met)n-OET)+H$^+$ ions. Ions in both series are 131 mass units or one methionine residue (C$_5$H$_9$NOS) apart. In both series, the value of n lies between 4–10.

Incorporation of HMB at the C-terminal end of the polymethionine chain should have resulted in a series of ions corresponding to ((Met)n-HMB-OCH$_3$)+H$^+$ ions. Such ions, if formed, would appear at m/z 688, 819, 958, 1081, 1212 and 1343. However, none of the peaks of this series were observed in the spectra. Similar results were obtained in the case of the negative ions (FIG. 28B). The absence of the methyl group provides indirect evidence that HMB is incorporated at the N-terminal end. It should be pointed out that dominant ions obtained in negative ion mode were adduct ions and contained a dimethyl sulfone moiety.

Example 6
Sonic Spray—MS-MS Results

The polymethionine and HMB-polymethionine prepared from Met-ethyl ester and HMB-ethyl ester were also subjected to MS-MS experiments. The freeze-dried precipitates were dissolved in DMSO (2 μg/μl) and the solution was introduced into the mass spectrometer with the sonic spray interface at the rate of 1 mL/hr. The solution was mixed with 1:1 acetonitrile:water mixture containing 0.1% acetic acid. The total fluid volume entering the SSI-MS was maintained at 0.2 mL/min. The parent ion and spectra obtained with the system are shown in FIG. 29.

Ions of (Met)n-O Et+H$^+$ corresponding to methionine hexamer, heptamer, octamer and nanomer were observed at m/z 833, 964, 1095 and 1225 amu respectively. For MS-MS experiment, the ion at m/z 833 was excited with an auxiliary Vrf and subjected to collision induced dissociation. The daughter spectrum of (Met)$_6$-EE is shown in FIG. 30. The prominent fragment ion was observed at m/z 657, this ion results from the cleavage of the amide bond resulting in the loss of Met-O Et (C$_7$H$_{14}$NO$_2$S) moiety from the C-terminal end. Similar results were obtained with molecular ions resulting from HMB-(Met)$_n^-$. Daughter ions resulting from the loss of HMB-O Methyl (C$_6$H$_{12}$NO$_2$S) moiety were not observed, indicating the absence of HMB-O Methyl at the C-terminal end.

Example 7
Papain Catalyzed Synthesis of HMB-Tyrosine Co-Oligomers

Synthesis of tyrosine oligomers and HMB-tyrosine co-oligomers was initiated with tyrosine ethyl ester (Tyr-OMe) and HMB ethyl ester as the monomer substrate. The overall synthesis and purification approach was similar to the one used for methionine and HMB-methionine described in Example 1.

Tyr-OMe (equal amounts (wt %) in the case of HMB-OEt and Tyr-OMe) were dissolved in 9.5 mL of 1M citrate buffer. EDTA and L-Cysteine were added. The reaction mixture was adjusted to a pH of 5.5 and 0.5 mL of papain suspension was added to the mixture. The reaction mixture was incubated in a shaker for 24 hours. The enzyme was then denatured by heating the reaction mixture to 80° C. for 10 minutes. The reaction mixture was cooled to room temperature.

The reaction mixture was filtered to collect the precipitate. The oligomer and co-oligomers in the precipitate were dissolved in DMSO to separate them from the monomers which are relatively insoluble in the solvent. The separated solvent was then evaporated to re-precipitate the oligomer and co-oligomers, which were then washed with water and freeze-dried.

The recipe for the tyrosine oligomers and HMB-tyrosine co-oligomers experiment are provided in Table 4.

TABLE 4

Reaction Mixtures Used for Tyrosine Oligomerization and HMB-Tyrosine Co-Oligomerization

| Components | MW | Moles | Wt |
| --- | --- | --- | --- |
| AA-ester | | | 3 g |
| L-Cys.HCl.H$_2$O | 175.6 | 100 mM | 0.1756 g |
| EDTA (anhyd) | 292.0 | 10 mM | 0.0292 g |
| Na Citrate | 294.1 | 1 M | 2.941 |
| Papain | 21428D | 7*10$^{-5}$ M | 15 mg |
| Volume | | | 10 mL |
| pH | | | 5.5 |

The reaction achieved a reaction rate similar to that observed with methionine in Example 1. Approximate oligomer yield was 70–80%. The freeze-dried oligomer precipitates were solubilized in DMSO. The solution concentration was brought to approximately 2 μg/μl. The solution was mixed with 1:1 acetonitrile:water mixture containing 0.1% acetic acid. The total fluid volume entering the ESI-MS was maintained at 0.2 mL min.$^{-1}$ The positive mass spectrum of the tyrosine oligomers is shown in FIG. 31.

Two sets of prominent ions appeared in the Tyr oligomers spectra. One series of ions appeared at m/z 834, 997, 1160 and 1323, while the other series of ions were found at m/z 862, 1025, 1188 and 1351. The ions in the first series represent (Tyr)n+H$^+$, while the ions in the second series represent (Tyr)n-OEt+H$^+$. The ions in the two series are 28 amu (C$_2$H$_4$) apart indicating the presence of O-Et at the C-terminal end in one series. Ions within the two series are separated by 163 amu, corresponding to the repeating unit of the Tyr residue (C$_9$H$_9$NO$_2$). Thus, the protonated ion at 862 most probably represents the tyrosine oligomers with five residues and an ethyl ester attached to the C-terminal end. Similarly, the ion at m/z 1025 most likely results from the (Tyr)$_6$_OEt+H$^+$. The ion at m/z 997 results from (Tyr)$_6$+H$^+$. The presence of oligomers with 5 to 8 Tyr residues is clearly evident, furthermore, the (Tyr)$_6$ was found to be the most prominent oligomer.

The positive ion mass spectrum of HMB-tyrosine co-oligomer is shown in FIG. 32A. The dominant ions in this spectrum were the same ions observed in the positive ion spectrum of polytyrosines, FIG. 31A. However, additional ions appeared at m/z 831, 994 and 1157. These ions appear at a mass difference of 133, suggesting the presence of a HMB residue in the co-oligomer. The peak at m/z 831 most probably represents the co-oligomer with one HMB residue and 4 tyrosine residues with the ethyl ester moiety (HMB-(Tyr)$_4$OEt+H$^+$). Similarly, the residues at m/z 994 and 1157 represent co-oligomers with one HMB residue and 6 and 7 tyrosine residues respectively. The weak intensity of these ions in part relate to lower proton affinity of the hydroxyl group.

Example 8
Papain Catalyzed Synthesis of HMB-Leucine Co-Oligomers

The papain-catalyzed synthesis of leucine and HMB co-oligomers was performed. Synthesis of leucine oligomers and HMB-leucine co-oligomers was initiated with leucine ethyl ester and HMB ethyl ester as the substrates. The overall synthesis and purification approach was similar to the one used in the case of methionine and HMB-methionine. Reaction rates similar to those obtained with methionine and tyrosine were achieved. Approximate oligomer yield was 58%. The freeze-dried oligomer precipitates were solubilized in DMSO. The solution concentration was brought to approximately 2 µg/µl The solution was mixed with 1:1 acetonitrile:water mixture containing 0.1% acetic acid. The total fluid volume entering the ESI-MS was maintained at 0.2 mL min.$^{-1}$ The positive mass spectrum of the leucine oligomers is shown in FIG. 33A.

Four sets of ions appeared in the positive ion spectra of $(Leu)_n$. One set of ions corresponding to $(Leu)_n+H^+$ appeared at m/z 698, 811 and 924. The other set of ions appeared at m/z 720, 833 and 947 and correspond to $(Leu)_n+Na^+$. Another set of ions appeared at m/z 747, 860 and 973 which correspond to $(Leu)_6$-OEt+Na$^+$, $(Leu)_7$-OEt+Na$^+$ and $(Leu)_8$-OEt+Na$^+$. However, the two prominent ions in the spectra appear to be $(Leu)_6$-OEt Na+Na$^+$ and (Leu)$_7$-OEt Na+Na$^+$. These results clearly show that the dominant oligomers are $(Leu)_5$, $(Leu)_6$, $(Leu)_7$ and $(Leu)_8$. The mass difference of 28 amu ($C_2H_4$) indicates the presence of O-Et at the C-terminal. Ions within the two series are separated by 113 amu, corresponding to the repeating unit of the Leu residue ($C_6H_{11}NO$). Thus, the doubly sodiated ($Na_2$) ion at m/z 770 and 883 most probably represents leucine oligomers with six and seven residues and a ethyl ester attached to the C-terminal end.

The negative ion mass spectrum of the leucine oligomers is shown in FIG. 33B. The overall appearance of the spectra is similar to that of the positive ion spectra. The two dominant ion in this spectra correspond to $(Leu)_6$-OEt+Na and $(Leu)_7$-OEt+Na.

The positive and the negative ion spectra of HMB-Leu co-oligomers are shown in FIG. 34. As expected, the positive spectra contained all of the dominant ions observed in the positive ion ESI-MS spectra of $(Leu)_n$. However, three additional strong ions at m/z 740, 853 and 866 were also found. These masses correspond to sodiated co-oligomers HMB-$(Leu)_5$+Na$^+$, HMB-$(Leu)_6$+Na$^+$ and HMB-$(Leu)_7$+Na$^+$ respectively. Thus, formation of co-oligomers with one HMB residue with five to seven leucine residues is clearly evident.

Example 9
Papain Catalyzed Synthesis of HMB-Phenylalanine Co-Oligomers

Papain catalyzed synthesis of phenylalanine and HMB co-oligomers was also conducted. Synthesis of phenylalanine oligomers and HMB- phenylalanine co-oligomers was initiated with phenylalanine ethyl ester and HMB ethyl ester as the substrates. The overall synthesis and purification approach was similar to the one used in the case of methionine and HMB-methionine in Example 1. The oligomerization reaction did not proceed when phenylalanine was the only substrate present in the reaction mixture. The reaction did proceed when HMB-ethyl ester was added to the reaction mixture. Reaction rates similar to those with methionine and tyrosine were achieved. Approximate oligomer yield was 90%. The freeze-dried oligomer precipitates were solubilized in DMSO. The solution concentration was brought to approximately 2 µg/µl. The solution was mixed with 1:1 acetonitrile:water mixture containing 0.1% acetic acid. The total fluid volume entering the ESI-MS was maintained at 0.2 mL min.$^{-1}$ As stated earlier, phenylalanine homo-oligomers were not formed.

Figure 35A:
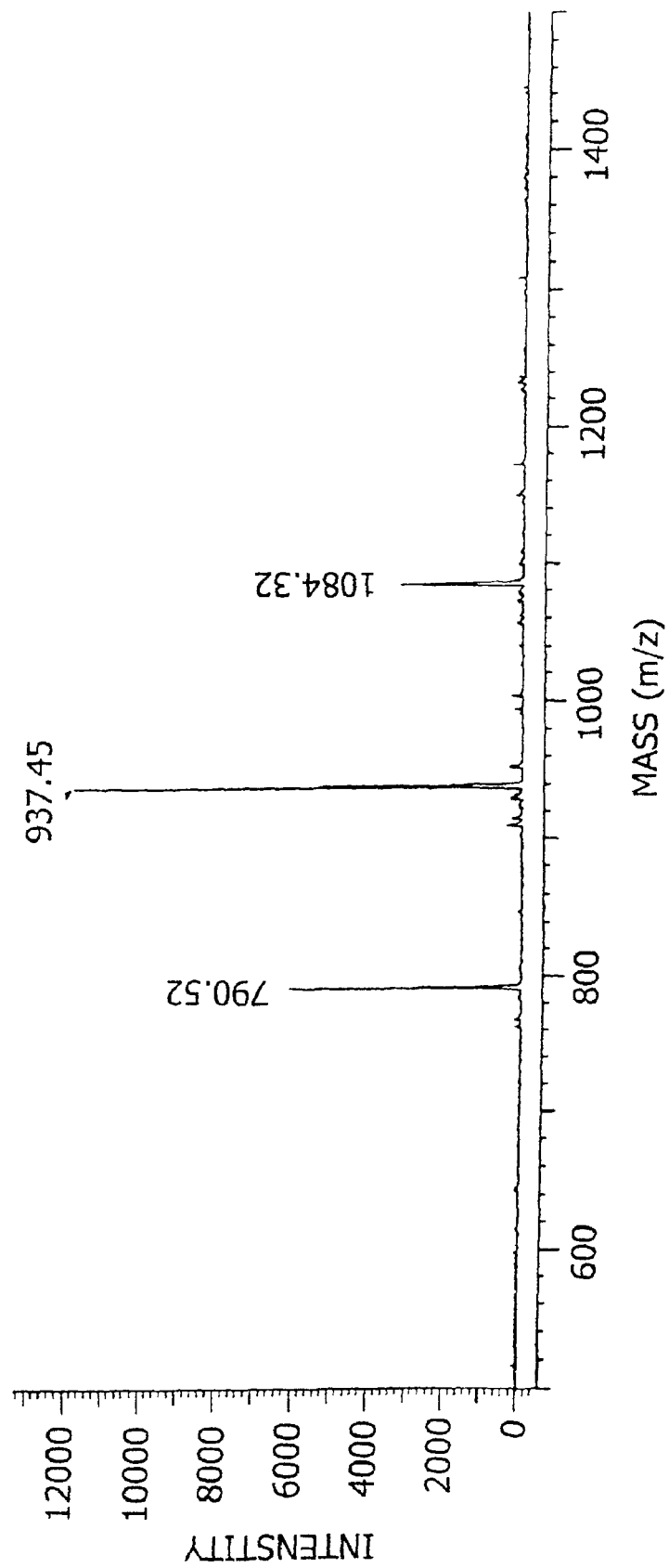
FIG. 35A is a positive ion ESI-MS spectra of HMB-phenylanaline co-oligomers.

The ESI-MS results of HMB-PheHMB co-oligomerization reaction are given in FIG. 35. The positive ion spectra of HMB-Phe co-oligomers are depicted in FIG. 35A, while the negative ion spectra are depicted in FIG. 35B. The positive spectra of the co-oligomers yielded three ion peaks at m/z 790, 937 and 1084. The mass difference between these ions is 147 or a difference of one phenylalanine residue ($C_6H_6NO$=147). The m/z values of the ions most likely correspond to HMB-$(Phe)_4$-OEt+Na$^+$, HMB-$(Phe)_5$-OEt+Na$^+$ and HMB-$(Phe)_6$-OEt+Na$^+$. Thus, formation of co-oligomers with one HMB residue and four to six Phe residues is clearly evident.

Example 10
Optimization of (Lys)n Oligomers and HMB-(Lys)n Co-oligomers Synthesis Experiments were conducted to optimize the reaction conditions for papain catalyzed synthesis of lysine oligomers and lysine co-oligomers with HMB. Reactions were carried out in two systems. The first system consisted of an aqueous phase and an immiscible organic phase, while the second system comprised a three-phase system consisting of an aqueous phase sandwiched between two mutually immiscible organic phases.

A. Two Phase Reaction System

The two-phase reaction system consisted of a small amount of polar phase and a larger amount of an immiscible non-polar phase. The polar phase comprised water, isopropyl amino ethyl and mercaptoethanol. This phase also contained the amino acid ester substrate and papain. During optimization, parameters such as the volume ratio of the aqueous and the non-aqueous phase, composition of additives, concentrations of the additives, concentrations of the substrates, and the concentration of the enzyme were varied. The effect of these parameters on the degree of oligomerization and yield were monitored. The results of the experiments are summarized below:

A.1 Aqueous: Organic Phase Ratio

Figure 36:
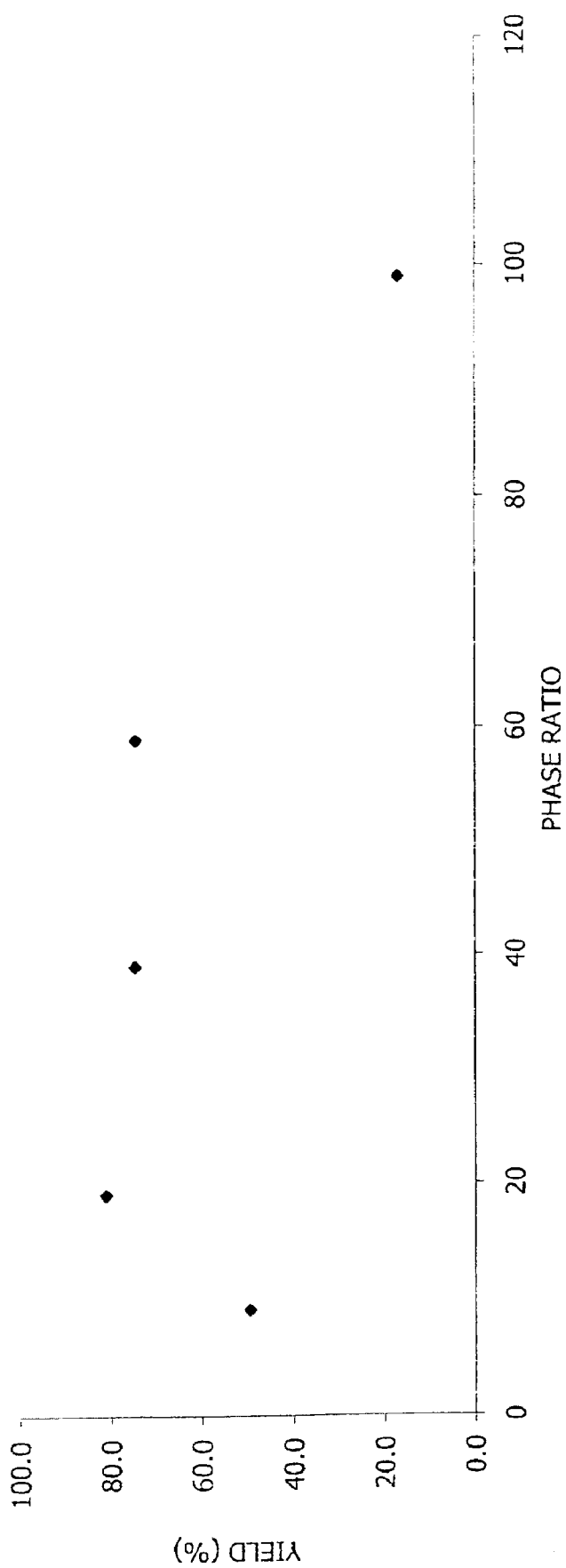
FIG. 36 is a graph of the effect of Aqueous: Non-Aqueous ratios on (Lys)$_n$ oligomer yield wherein n is the number of lysine residues in the oligomers in a two-phase system.

To optimize the volume ratio of the aqueous and organic phases (toluene), the oligomer yields and degree of oligomerization were monitored over phase ratios ranging from 1:9–1:99, the reaction was allowed to proceed for 24 hours. Oligomer were recovered from the aqueous phase and analyzed. Results of these experiments are shown in FIG. 36.

Figure 37:
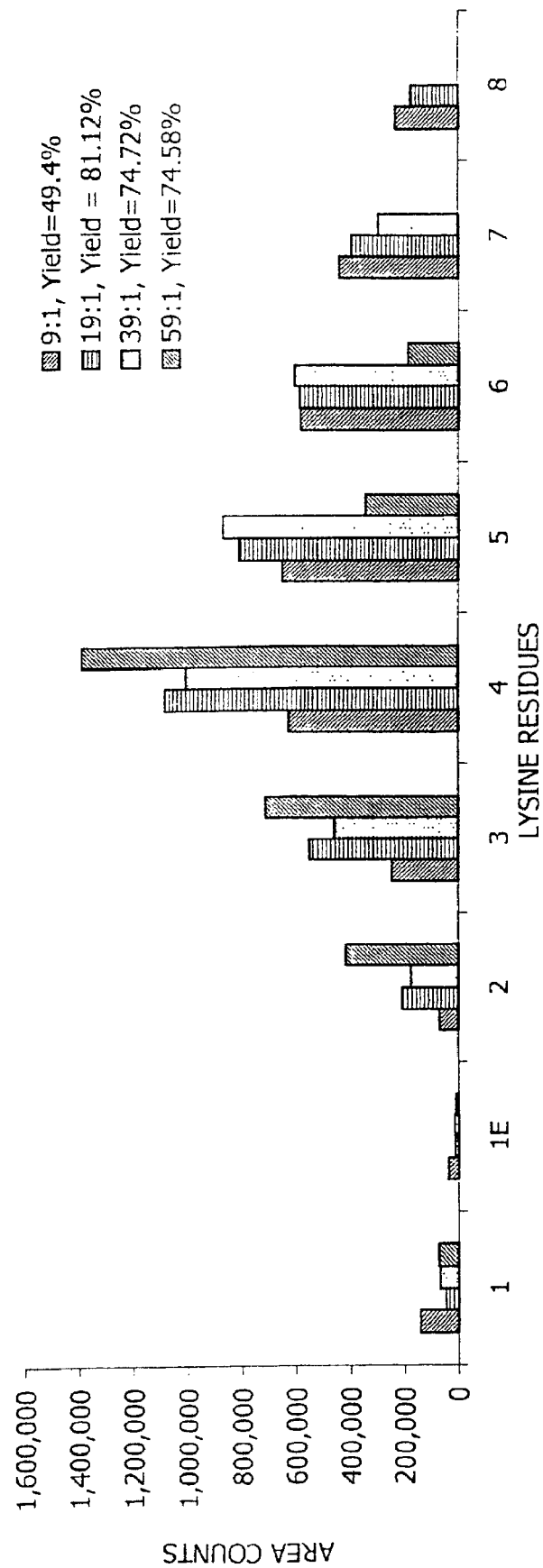
FIG. 37 is a bar graph of the effect of volumetric ratios on the degree of (Lys)$_n$ oligomer yield in a two-phase reaction system wherein n is the number of lysine residues in the oligomers.

The results indicate that the yields dropped at ratios below 19 and the higher ratios did not lead to an appreciable change in total yield. The results also showed that while the total yield did not change at higher organic solvent volumes, the degree of oligomerization was affected. Higher toluene volume led to a decrease in the degree of oligomerization. The length of oligomers chains at phase ratio 1:19 extended up to nine lysine residues $(Lys)_9$, whereas at phase ratio 1:39, the largest oligomers contained only six lysine residues $(Lys)_6$, FIG. 37. In light of these results and to conserving organic solvent, all subsequent experiments were carried out at phase ratio 1:19.

A.2 Optimization of Additive Concentration

Figure 38:
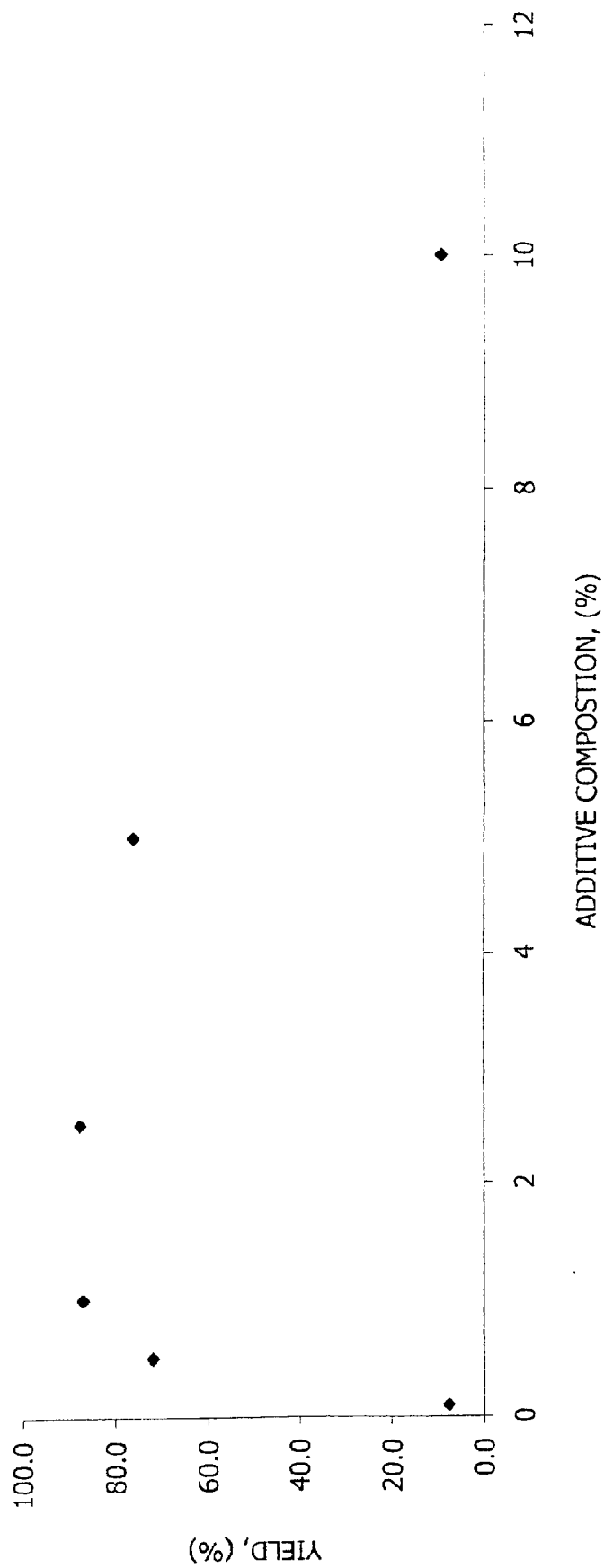
FIG. 38 is a graph of the effect of additive concentrations on (Lys)$_n$ oligomer yield wherein n is the number of lysine residues in the oligomers.

The effect of the concentration of additives (mercaptoethanol and isopropyl ethyl amine) on yield and degree of oligomerization was also examined. These additives act as antioxidants and prevent oxidation of cysteine moiety in the enzyme. The reaction was carried out for 24 hours. Oligomers were recovered from the aqueous phase and analyzed. Results showed that concentration of additives had a marked effect on the total yield and the degree of oligomerization. The total yield increased with an increase in additive concentration from 0.1–2%. However, a pronounced decrease in total oligomers yield was observed when the additive concentration was increased above 5%. A 2% additive concentration was found to the optimum under conditions used in these experiments. The total oligomers yield at this additive concentration was approximately 87%, FIG. 38.

Figure 39:
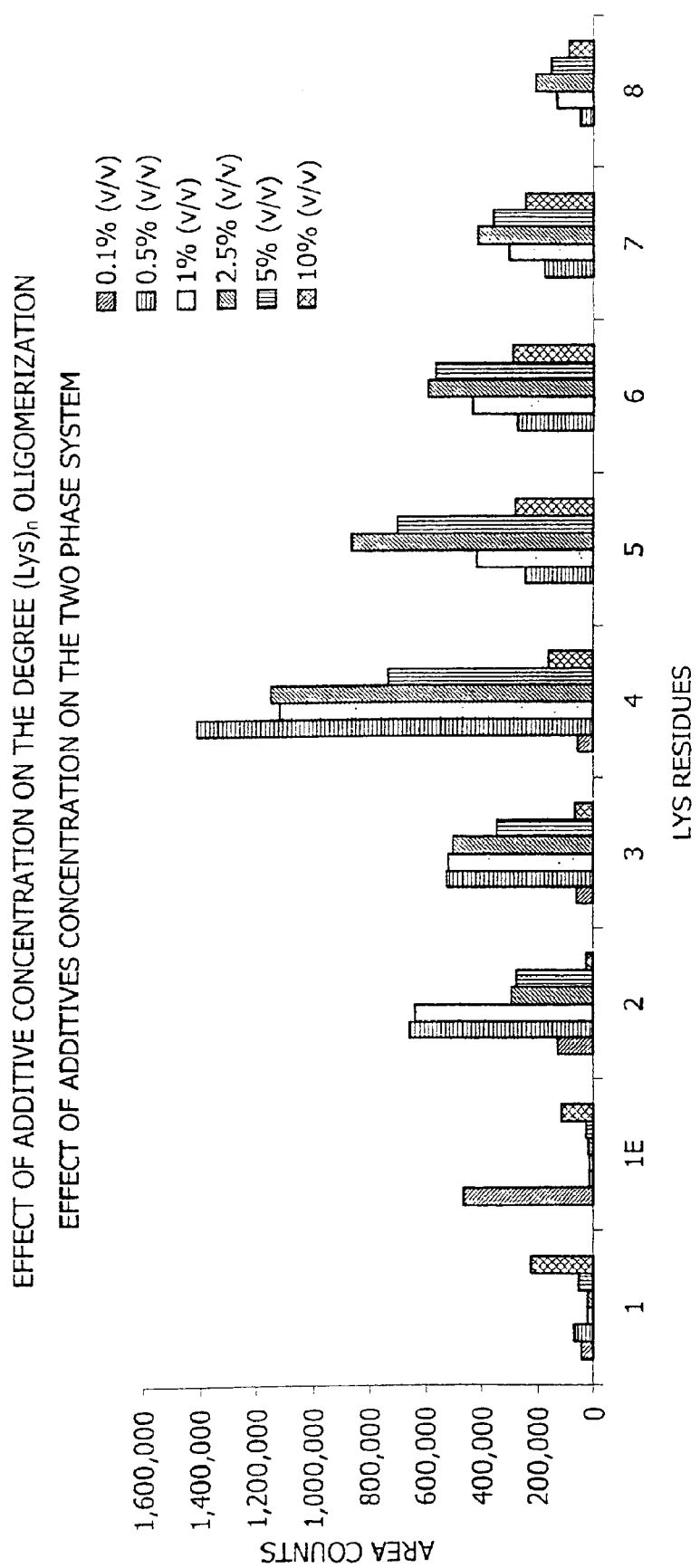
FIG. 39 is a bar graph of the effect of additive concentrations on the degree of (Lys)$_n$ oligomerization wherein n is the number of lysine residues in the oligomers.

The degree of oligomerization was found to increase with an increase in additive concentration up to 2%, still higher concentrations did not lead an appreciable change in the oligomers distribution as shown in FIG. 39.

A.3 Optimization of Substrate Concentration

Figure 40:
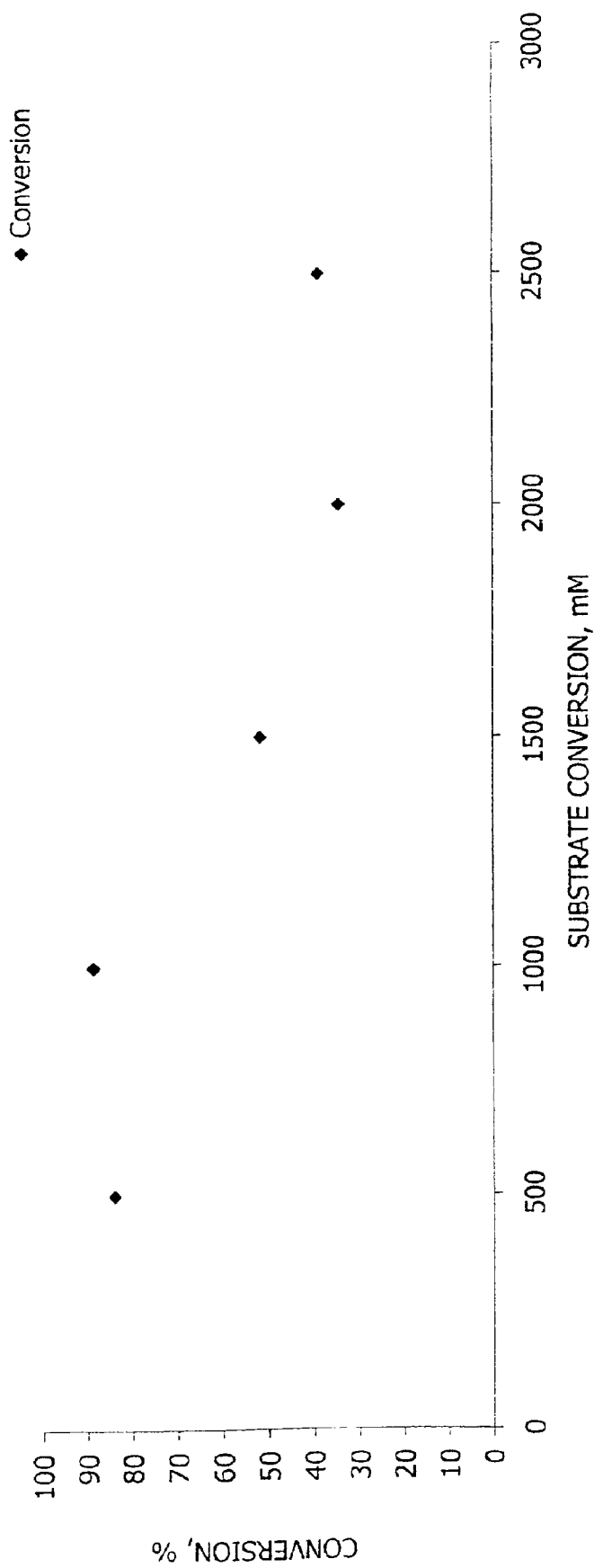
FIG. 40 is a graph of the effect of substrate concentrations on (Lys)$_n$ oligomer yield wherein n is the number of lysine residues in the oligomers.

A series of experiments were carried to optimize the substrate (lysine ethyl ester) concentration at a fixed enzyme activity. The concentration of substrate was varied five folds, from 500 mM to 2,500 mM, while the enzyme concentration was held constant at 1.21 mM. Oligomerization reactions were allowed to proceed for 24 hours after which the enzyme was deactivated and oligomers recovered from the aqueous phase and analyzed. A plot of the percent oligomers yield (total oligomers mass/total substrate mass×100) vs the substrate mass is shown in FIG. 40.

Figure 41:
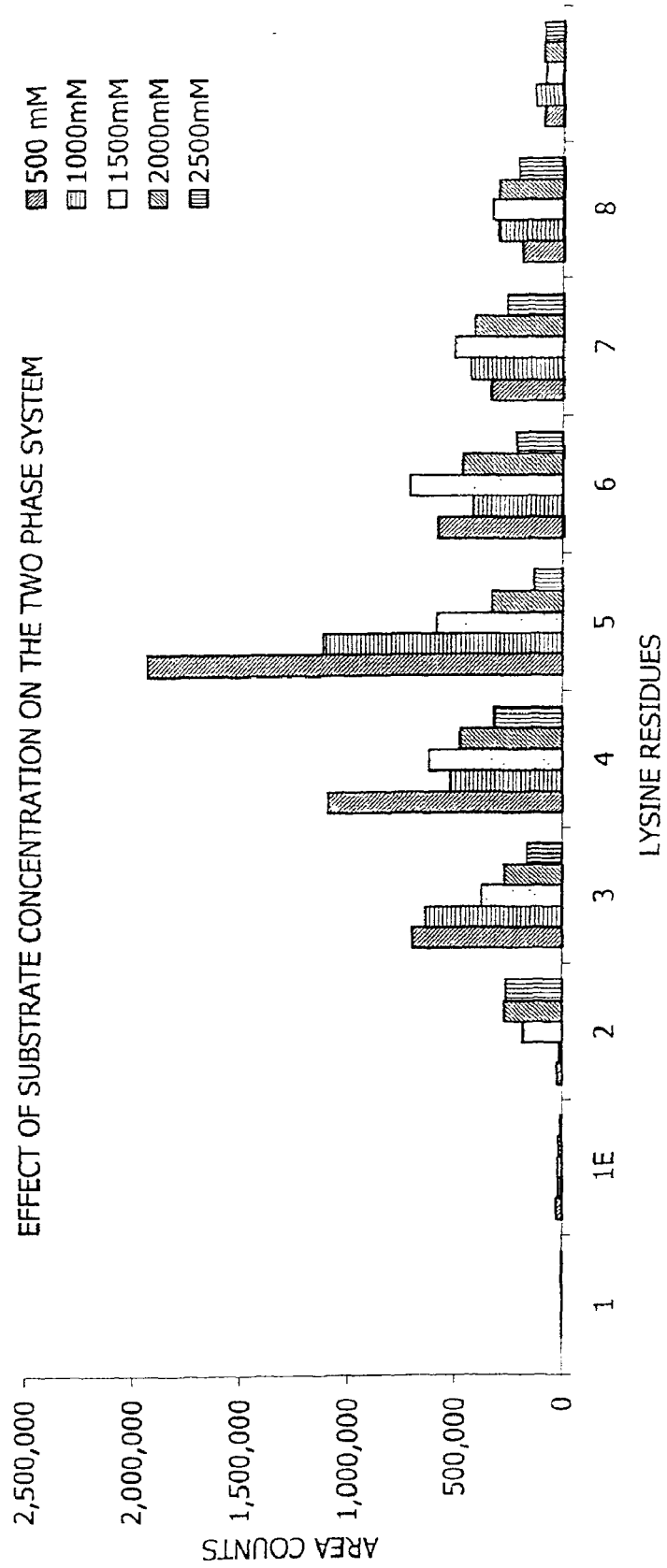
FIG. 41 is a bar graph of the distribution of lysine oligomers formed in reaction mixtures with varied substrate concentrations.

The results show that the highest conversion efficiency was achieved at a substrate concentration of 1000 mM. A noticeable drop in conversion efficiency above this concentration was clearly evident. The degree of oligomerization was also affected by the substrate concentration. In general, higher concentration led to the formation of oligomers with higher lysine residues (e.g., the most abundant oligomers at 500 mM lysine ethyl ester was $(Lys)_4$ and the yield of higher homologs was quite low). The most abundant oligomer was $(Lys)_5$. In addition, concentrations of higher homologs $(Lys)_6$, $(Lys)_7$ and $(Lys)_8$ were noticeably higher, FIG. 41.

A.4 Optimization of Incubation Period

Figure 42:
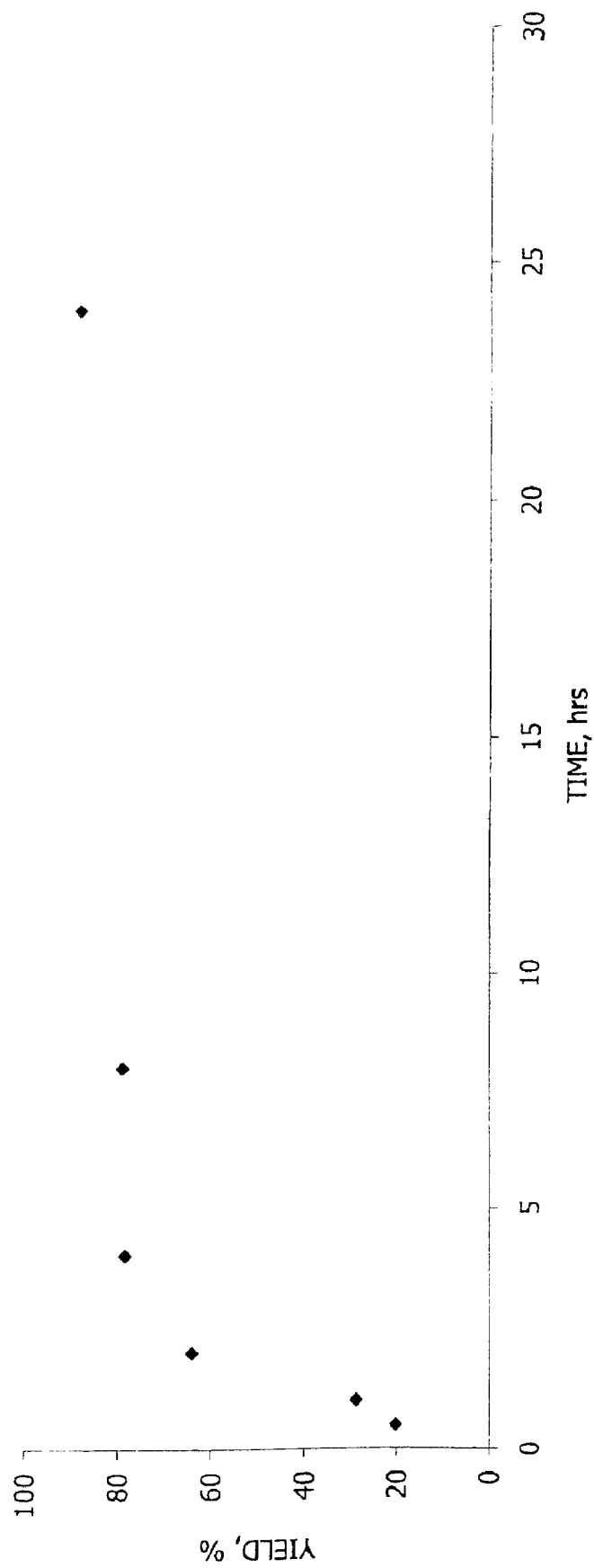
FIG. 42 is a graph of the effect of incubation time on total lysine oligomer yield.

Another set of experiments was carried out to determine an optimum incubation period for oligomerization of lysine. The reaction were conducted with 1:19 phase ratio, 1 M substrate concentration and 1% additive concentration. The reaction was allowed to continue for time periods ranging between 30 minutes to 24 hours. After each time period, the reaction was brought to halt by deactivating the enzyme. The oligomers were recovered from the aqueous phase and analyzed. The total oligomers yield obtained at various time periods is shown in FIG. 42.

Figure 43:
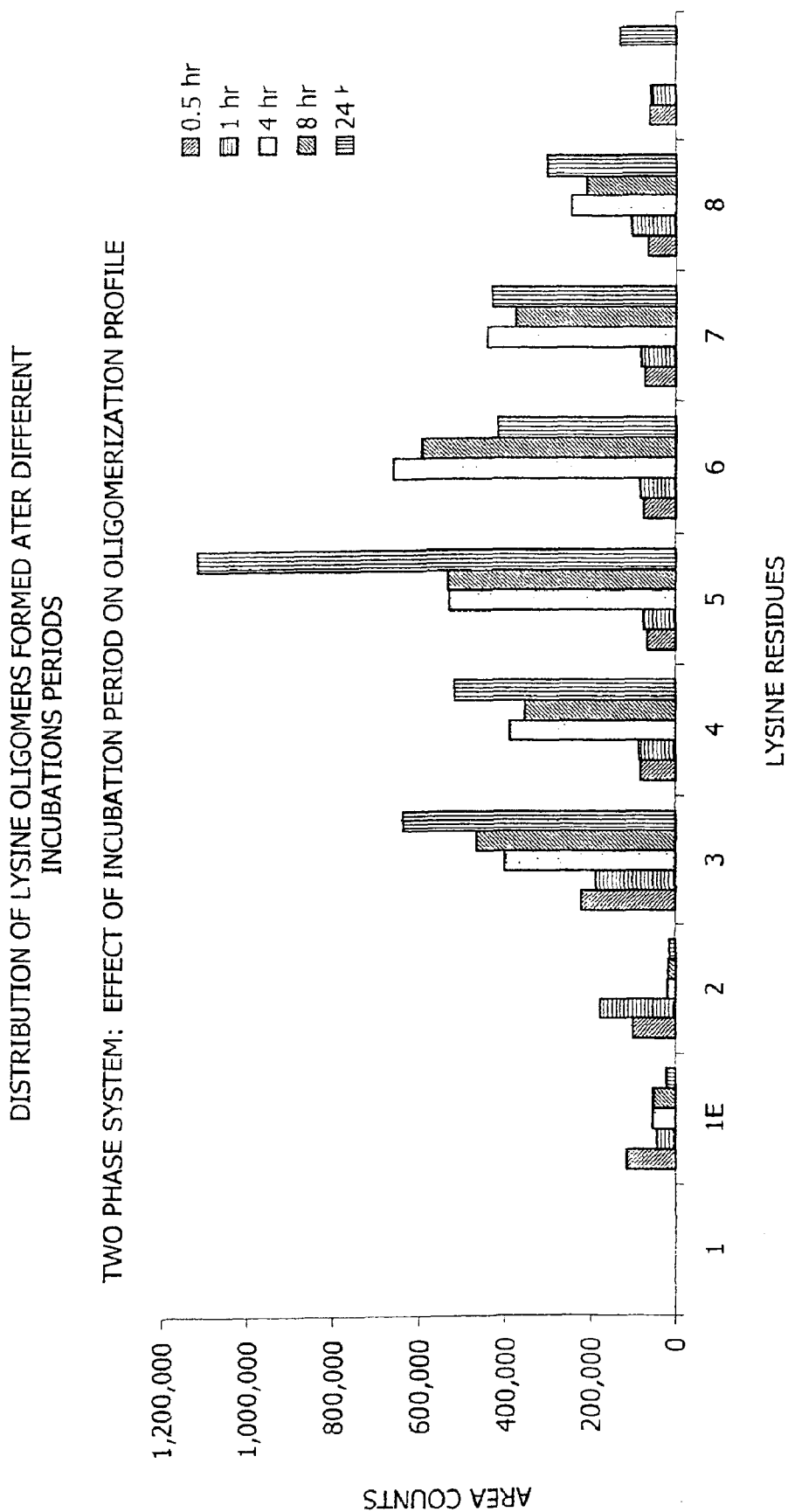
FIG. 43 is a bar graph of the distribution of lysine oligomers formed after different incubation time periods.

The graph shows that the reaction is nearly complete within the first four hours and only a marginal increase in yield is obtained at longer incubation periods. Analyses of oligomers obtained after different time periods showed that the time periods shorter than 4 hours yield an even distribution of oligomers from $(Lys)_2$ to $(Lyn)_8$, while the longer periods yield higher concentrations of $(Lyn)_4$ to $(Lys)_6$ oligomers, FIG. 43.

B. Three Phase System

The three-phase system consisted of an aqueous phase present between two immiscible non-aqueous phases, one lighter than the aqueous phase and the other heavier than the aqueous phase. The heavier phase comprised decafluoropentane and the lighter phase comprised n-octane. Isopropyl ethyl amine and mercaptoethanol additives were added to the aqueous phase along with the lysine ethyl ester (substrate) and papain (enzyme). The effects of parameters such as the relative volumes of aqueous to non-aqueous phases, the concentration of the additives, the substrate concentration and the enzyme activity on oligomers yield and degree of oligomerization were monitored through a set of experiments.

B 1. Optimization of Aqueous and Non-Aqueous Phase Ratio

Figure 44:
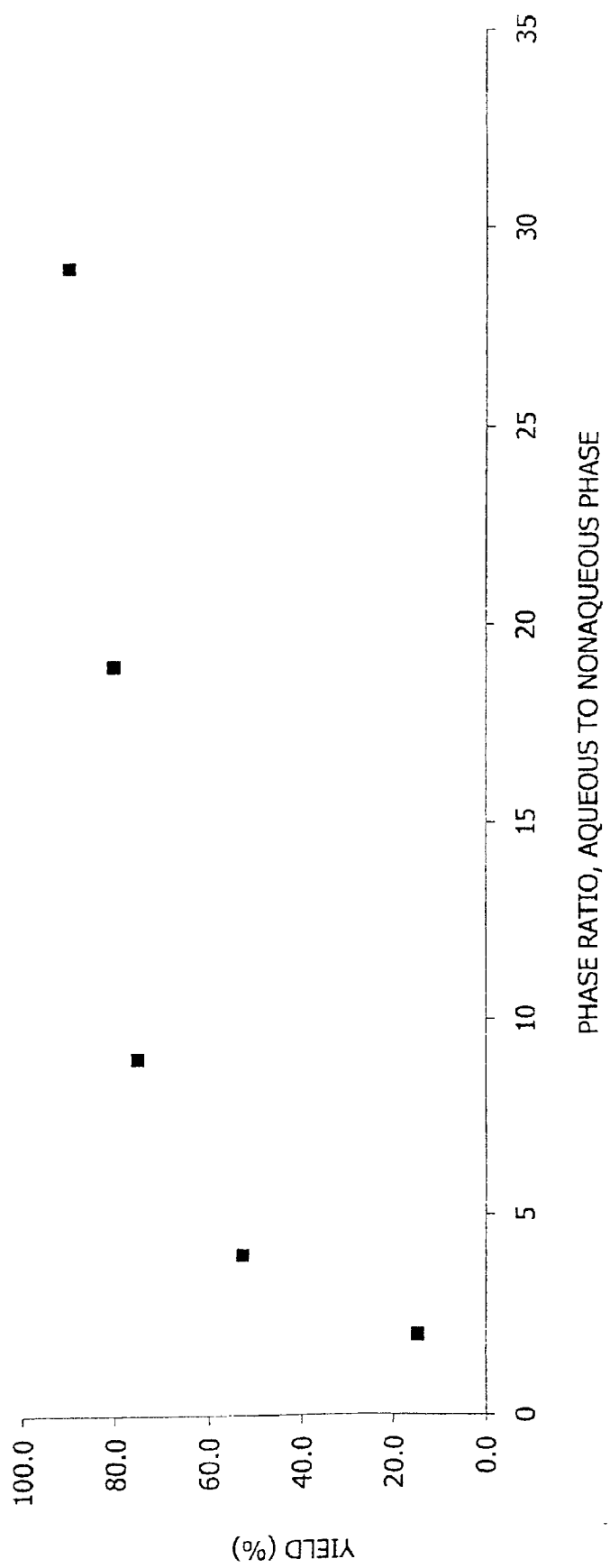
FIG. 44 is a graph of the effect of aqueous to non-aqueous solvent phase ratios on total lysine oligomer yield in a three-phase system.

The ratio of the non-aqueous phase volume to aqueous phase volume was varied by changing the volumes of the two organic solvents in equal proportion while holding the aqueous phase volume constant. Substrates, antioxidant additives and enzyme were added to the aqueous phase. The reactants and the enzyme were placed in a stirred reactor and allowed to incubate at 37° C. for 24 hours. The total oligomers yield was determined gravimetrically, while the degree of oligomerization was determined through RPLC analysis. Results of gravimetric determination are represented in FIG. 44.

Figure 45:
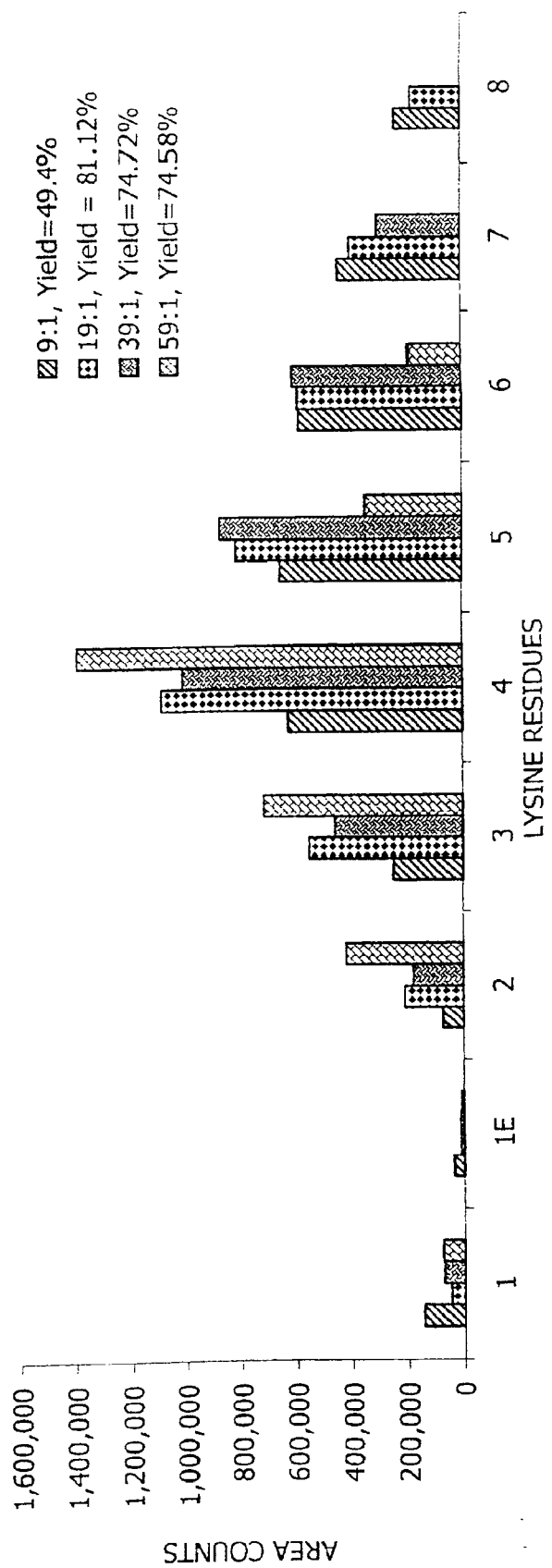
FIG. 45 is a bar graph of the distribution of lysine oligomers formed in reaction mixtures at various aqueous to non-aqueous solvent ratios.

The results show that the oligomer yield increased with an increase in total organic phase. However, the increase in yield was relatively small above an aqueous:organic ratio of 1:10. The effect of phase ratio on the degree of oligomerization is shown in FIG. 45. Results show that while the total yields are lower (approximately 15–50%) at the lower phase ratios, the degree of oligomerization is higher and oligomers with up to 10 lysine residues can be readily obtained. At higher phase ratios, the total oligomers yields are significantly greater (e.g., up to approximately 85%). The degree of oligomerization was generally lower, however, as the predominant oligomers formed under these conditions contained three to five lysine residues.

B 2. Optimization of Additives Concentration

Figure 46:
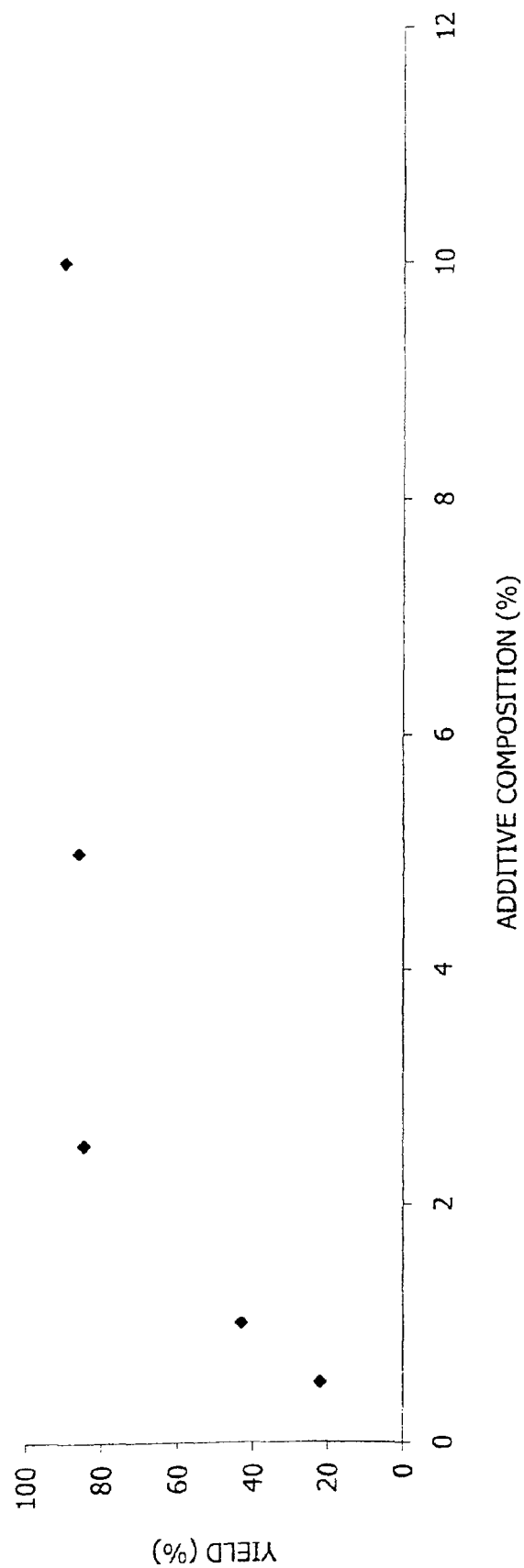
FIG. 46 is a graph of the effect of additive concentrations on the total lysine oligomers yield.
Figure 47:
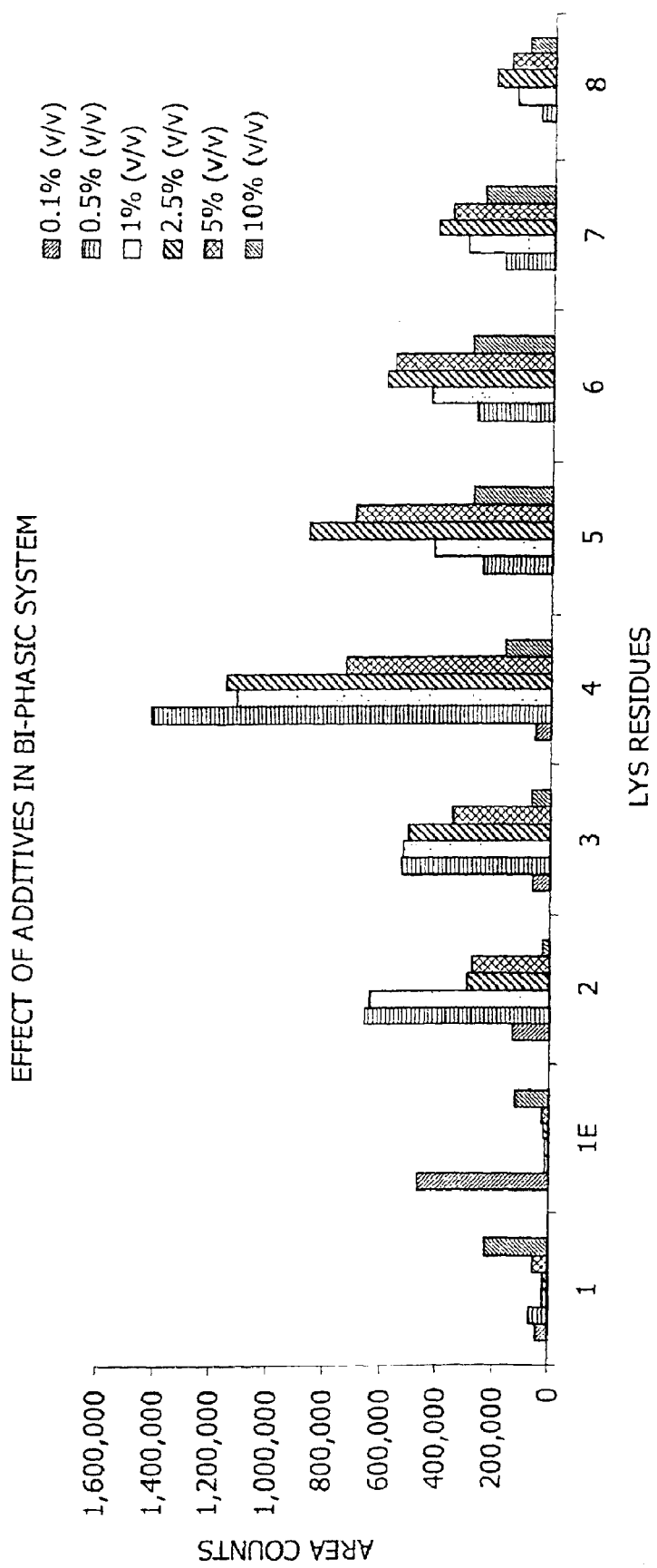
FIG. 47 is a bar graph of the distribution of lysine oligomers formed with varied additive concentrations in a 2-phase system.

The effect of the total additive concentration on the oligomers yield and degree of oligomerization was examined. At low additive concentrations (e.g., concentrations <1.5%), the overall oligomers yields were low (e.g., approximately 40%). An increase in additive concentration up to 2.5% led to an increase in the oligomers yield, however, concentration above this level did not lead to higher yields, FIG. 46. The concentration of the additives did not assert a pronounced effect on the distribution of lysine oligomers, FIG. 47.

B 3. Optimization of Incubation Period

Figure 48:
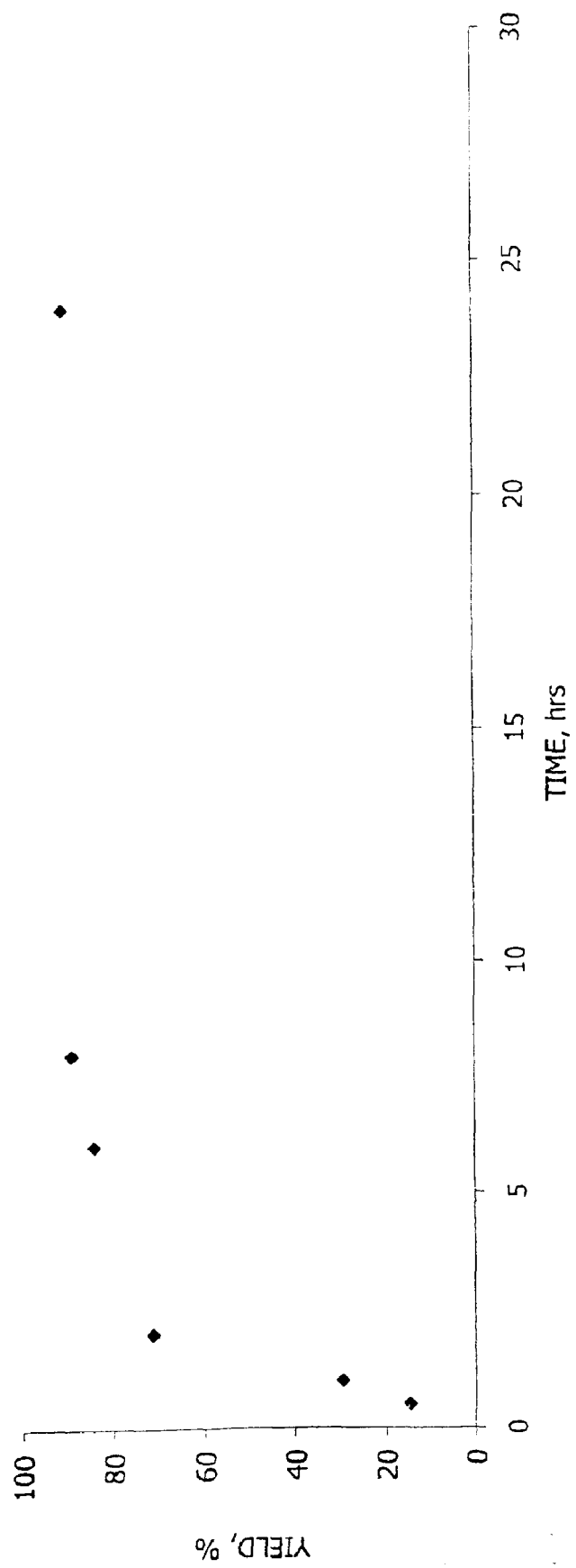
FIG. 48 is a graph of the total lysine oligomer yield formed after different incubation time periods in a 3-phase system.
Figure 49:
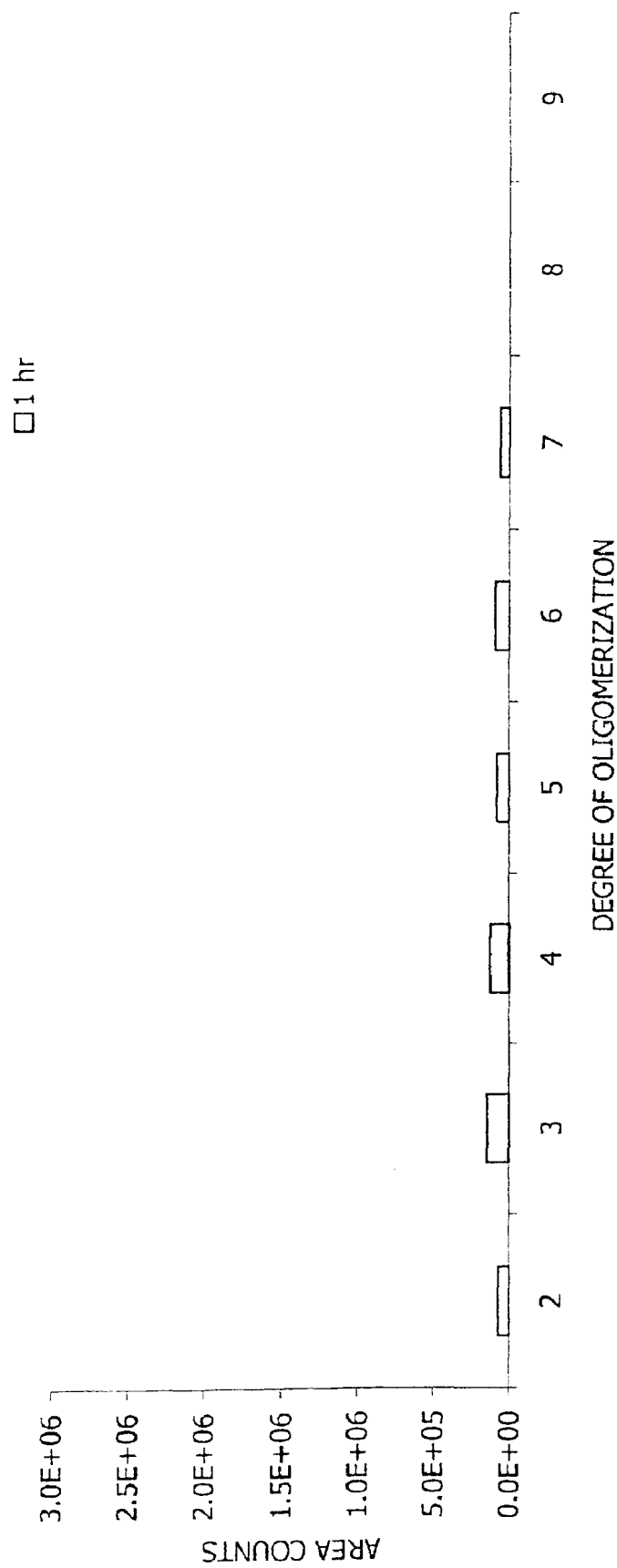
FIG. 49 is a bar graph of the distribution of lysine oligomers formed after a one hour incubation period in a 3-phase system.

The incubation period for the three-phase reaction system was examined through another set of experiments. The experiments were conducted with three phase reaction mixtures consisting of aqueous phase and total organic phases, the aqueous:organic phase ratio was set at 1:9. The additive concentrations were varied. The incubation periods were varied from 30 minutes to 30 hours. After each time period, total oligomer yield and degree of oligomerization were examined. Results are shown in FIG. 48. The results indicate that the reaction reaches completion in approximately six hours and nearly 90% of the initial substrate mass is converted into the oligomers. Longer incubation periods did not lead to higher yields.

Figure 50:
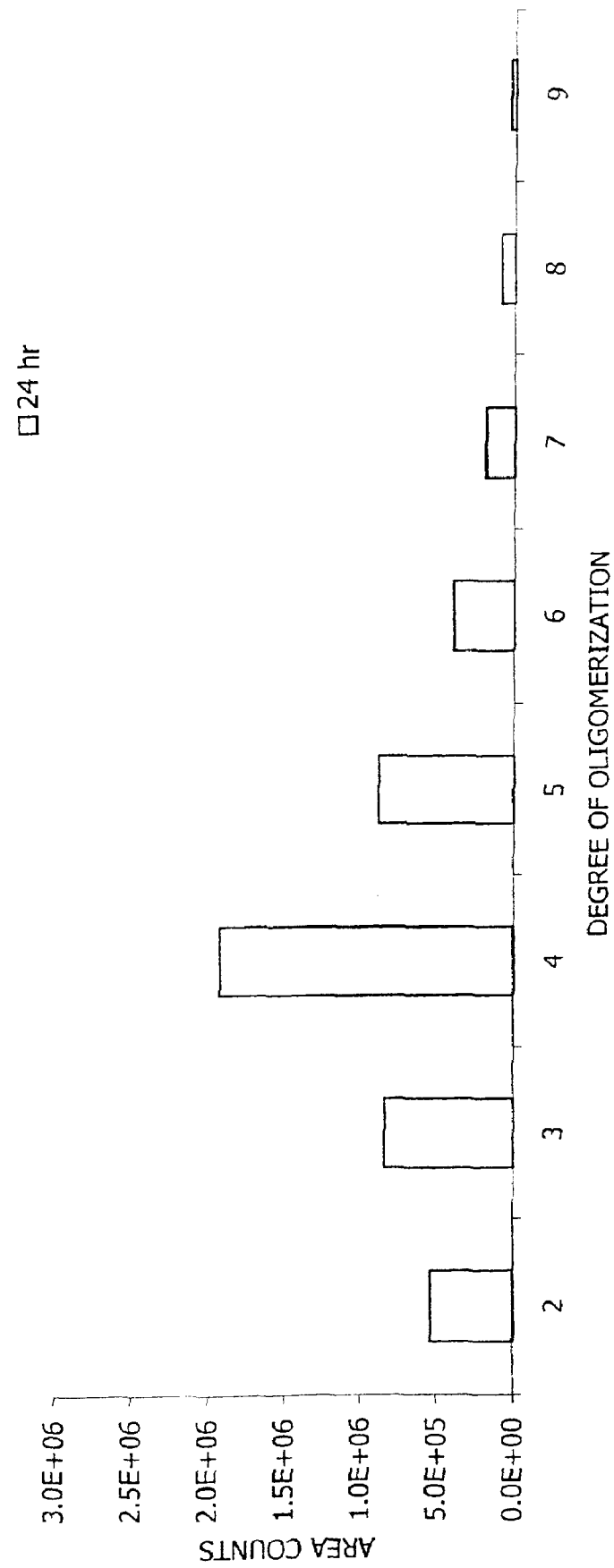
FIG. 50 is a bar graph of the distribution of lysine oligomers formed after a 24 hour incubation period in a 3-phase system.

RPLC results showed that the longer incubation periods favored oligomers with smaller lysine residues. The predominant residue after a 24 hour incubation period was found to be $(Lys)_4$, FIG. 50.

The studies above demonstrate the effect of various parameters in the three phase and two-phase systems and can be used to tailor the reaction to produce the required residue range and composition.

Example 11

Synthesis of Tryptophan Oligomers and HMB-Tryptophan Co-Oligomers

A procedure similar to one used for the synthesis of Met oligomers and HMB-Met co-oligomers of Example 1 was employed for the synthesis of tryptophan oligomers and HMB-Tryptophan co-oligomers.

Trp-OMe was dissolved in 4.5 mL of 2M citrate buffer along with the EDTA and L-Cysteine. The pH was adjusted to 5 and 0.5 mL of papain suspension was added to the mixture. The mixture was placed in a shaker for three days and incubated. After three days, the enzyme was denatured by heating the broth for a duration of 10 minutes at 80° C.

The broth was filtered to collect the precipitate. Alternatively, the broth could be centrifuged to collect the precipitate. The oligomer and co-oligomer precipitate was dissolved in DMF to separate them from the monomers which are relatively insoluble in the solvent. The solvent was evaporated and the precipitate was washed with water, followed by freeze-drying the precipitate to obtain the dry oligomers and co-oligomers.

The procedure was also performed wherein L-Tyrosine Ethyl Ester was substituted for Trp-OMe. The recipes for synthesis of different oligomers and co-oligomers are summarized below in Table 5.

TABLE 5

Recipes for the Synthesis and Purification of L-Trp Homo-Oligomers and HMB-L-Trp Hetero-Co-Oligomers

| | | Jost/Trp-OEt | | Selvi/Trp-OMe | | |
|---|---|---|---|---|---|---|
| Components | MW | Moles | Wt | Moles | Wt | Wt |
| AA-ester | | | 3 g | 0.38 M | 370 mg | |
| L-Cys.HCl.H$_2$O | 175.6 | 100 mM | 0.1756 g | 100 mM | 0.0878 | |
| EDTA (anhyd) | 292.0 | 10 mM | 0.0292 g | 10 mM | 0.01461 g | |
| Na Citrate | 294.1 | 1 M | 2.941 | 2 M | 2.941 g | |
| Papain | 21428 D | 7*10$^{-5}$ M | 15 mg | 1.4*10$^{-4}$ M | 15 mg | |
| Volume | | | 10 mL | | 5 mL | |
| pH | | | 5.5 | | 5 | |

Example 12
Synthesis and Purification of Leucine, Phenylalanine, and Tryptophan Oligomers A procedure similar to one used for the synthesis of Met oligomers and HMB-Met co-oligomers of Example 1 was employed for the synthesis and purification of leucine, phenylalanine, and tryptophan oligomers. An amino acid ester (e.g., 1 mmole) was dissolved in 10 mL of 2M phosphate buffer solution at pH 7.5 containing 1 mM dithiothreithol and 5 mM EDTA. A papain suspension (e.g., 0.1 mmole) was added to the solution. The solution was incubated for two days with continuous shaking, after which the precipitate formed was filtered and washed with water several times to remove the free monomers. The precipitate was dried in vacuo and then subjected to analysis.

The recipes for synthesis of different oligomers are summarized below in Table 6.

TABLE 6

Recipes for the Synthesis and Purification of Leucine, Phenylalanine, and Tryptophan Oligomers

| Components | Moles | MW | Wt |
|---|---|---|---|
| AA-OEt.HCl | 0.1 mM | | |
| Dithiothreithol | 1 mM | 154.2 | 0.00152 g |
| EDTA | 5 mM | 292.2 | 0.01461 g |
| Na$_2$HPO$_4$/NaH$_2$PO$_4$ (Phosphate Buffer) | 2 M | | |
| Volume | | | 10 mL   10 mL |

Example 13
A General Procedure for the Synthesis and Purification of Oligomers

L-amino acid ethyl ester or D, L-amino acid esters and racemic HMB ethyl ester were dissolved in buffer containing L-cysteine, EDTA and sodium citrate at pH 5.5 as detailed in Tables 5–9. The buffer pH was set at 5.5 and 0.5 mL of papain suspension containing 15 mg of protein was added to the reaction broth. After incubation in a shaker for 24 hours at 35° C., the enzyme was denatured by heating the broth to 80° C. for 10 minutes. The broth with denatured enzyme was then cooled to room temperature. The oligomer and co-oligomer precipitate obtained from the reaction was washed exhaustively with water to remove the monomers and the washed precipitate was then freeze-dried. The freeze-dried oligomer and co-oligomer precipitate was solubilized in DMSO to form a 2 µg/µL solution. To remove traces of free HMB-ester, HMB co-oligomers were re-precipitated by addition of distilled deionized water. The purified oligomers and co-oligomers were freeze dried. The oligomer and co-oligomer were dissolved in appropriate solvents or mixtures solution (DMSO and 1:1 acetonitrile-:water mixture) for chemical characterization with liquid chromatography (LC) diode array detector, LC-electrospray mass spectrometry (ESI-MS), sonic spray ionization—MS (SSI-MS) and matrix assisted desorption ionization—MS (MALDI-TOF).

Recipes for synthesis of different oligomers and co-oligomers are summarized in Tables 7–11.

TABLE 7

Recipes for the Synthesis and Purification of L-Met Oligomers and HMB-L-Met Co-Oligomers

| Components | MW | Moles | Met | HMB-Met |
|---|---|---|---|---|
| L-AA-OEt.HCl | 213.7 | | 3 g | 1.5 g |
| DL-HMB-OEt | 178 | | — | 1.5 g |
| L-Cys.HCl.H$_2$O | 175.6 | 100 mM | 0.1756 g | 0.1756 g |
| EDTA (anhyd) | 292.0 | 10 mM | 0.0292 g | 0.0292 g |
| Na Citrate | 294.1 | 1 M | 2.941 g | 2.941 g |
| Papain | 21428D | 7*10$^{-5}$ M | 15 mg | 15 mg |
| Volume | | | 10 mL | 10 mL |
| pH | | | 5.5 | 5.5 |

TABLE 8

Recipes for the Synthesis and Purification of L-Tyr Oligomers and HMB-L-Tyr Co-Oligomers

| Components | MW | Moles | Tyr | HMB-Tyr |
|---|---|---|---|---|
| L-AA-OEt | | | 933.36 mg | 466.82 mg |
| DL-HMB-OEt | 178 | | — | 338.2 mg |
| L-Cys.HCl.H$_2$O | 175.6 | 100 mM | 0.1756 g | 0.1756 g |
| EDTA (anhyd) | 292.0 | 10 mM | 0.0292 g | 0.0292 g |
| Na Citrate | 294.1 | 1 M | 2.941 g | |
| Papain | 21428D | 7*10$^{-5}$ M | 15 mg | 15 mg |

TABLE 8-continued

Recipes for the Synthesis and Purification of L-Tyr Oligomers and HMB-L-Tyr Co-Oligomers

| Components | MW | Moles | Tyr | HMB-Tyr |
|---|---|---|---|---|
| Volume | | | 10 mL | 10 mL |
| pH | | | 5.5 | 5.5 |

TABLE 9

Recipes for the Synthesis and Purification of L-Leu Oligomers and HMB-L-Leu Co-Oligomers

| Components | MW | Moles | Leu | HMB-Leu |
|---|---|---|---|---|
| L-AA-Oet | | | 2.739 g | 1.369 g |
| DL-HMB-OEt | 178 | | — | 1.253 g |
| L-Cys.HCl.H$_2$O | 175.6 | 100 mM | 0.1756 g | 0.1756 g |
| EDTA (anhyd) | 292.0 | 10 mM | 0.0292 g | 0.0292 g |
| Na Citrate | 294.1 | 1 M | 2.941 g | 2.941 g |
| Papain | 21428D | 7 * 10$^{-5}$ M | 15 mg | 15 mg |
| Volume | | | 10 mL | 10 mL |
| pH | | | 5.5 | 5.5 |

TABLE 10

Recipes for the Synthesis and Purification of L-Phe Oligomers and HMB-L-Phe Co-Oligomers

| Components | MW | Moles | Phe | HMB-Phe |
|---|---|---|---|---|
| L-AA-Oet | | | 1.1414 g | 0.5707 g |
| DL-HMB-OEt | 178 | | — | 0.4067 mg |
| L-Cys.HCl.H$_2$O | 175.6 | 100 mM | 0.1756 g | 0.1756 g |
| EDTA (anhyd) | 292.0 | 10 mM | 0.0292 g | 0.0292 g |
| Na Citrate | 294.1 | 1 M | 2.941 g | 2.941 g |
| Papain | 21428D | 7*10$^{-5}$ M | 15 mg | 15 mg |
| Volume | | | 10 mL | 10 mL |
| pH | | | 5.5 | 5.5 |

TABLE 11

Recipes for the Synthesis and Purification of L-Trp Oligomers and HMB-L-Trp Co-Oligomers

| Components | MW | Moles | Trp | HMB-Trp |
|---|---|---|---|---|
| L-AA-Oet | | | 0.48 mg | 0.480 g |
| DL-HMB-OEt | 178 | | — | 0.480 mg |
| L-Cys.HCl.H$_2$O | 175.6 | 100 mM | 0.1756 g | 0.1756 g |
| EDTA (anhyd) | 292.0 | 10 mM | 0.0292 g | 0.0292 g |
| Na Citrate | 294.1 | 1 M | 2.941 g | 2.941 g |
| Papain | 21428D | 7*10$^{-5}$ M | 15 mg | 15 mg |
| Volume | | | 10 mL | 10 mL |
| pH | | | 5.5 | 5.5 |

Example 14
Enantioselectivity of Papain Catalyzed Oligomerization and Co-Oligomerization A set of experiments was carried out to discern enantioselectivity of papain wherein oligomers and co-oligomers were catalyzed from an amino acid and HMB. The experiments entailed enantioselective determination of the reactants (e.g., methionine and HMB co-oligomerization from enantiomeric mixtures of D, L-methionine and D, L-HMB and separation of supernatant and oligomer and co-oligomer precipitates). The supernatant was filtered to remove suspended matter, and the precipitate was purified through repeated washing and DMSO back-extraction. The purified oligomer and co-oligomer precipitates were hydrolyzed with acid. The reactant solutions, supernatant, and hydrolyzates were subjected to enantioselective HPLC analysis. The results of the experiments indicated that catalytic co-oligomerization of amino acids and HMB is enantioselective wherein only the L-HMB and the L-amino acid isomers undergo oligomerization and co-oligomerization.

Papain Catalyzed Synthesis

The Met oligomers and HMB-Met co-oligomers were synthesized through papain mediated enzymatic reactions at pH 5.5. The synthesis involved the following steps:

Racemic mixtures of both D, L-Met-OEt and D, L-HMB-OEt were dissolved in 4.5 mL of 2M citrate buffer along with EDTA and L-Cysteine. The pH was set to 5 and 0.5 mL of papain suspension was added to the mixture. The mixture was incubated in a shaker for 3 days.

After the mixture was incubated in a shaker for 3 days, the enzyme (e.g., papain) was denatured by heating the mixture for 10 minutes at 80° C.

The mixture was filtered and the precipitate collected. (Alternatively, the mixture may be centrifuged to separate the precipitate from the supernatant).

The oligomers and co-oligomers were dissolved in DMF to separate them from the monomers, which are relatively insoluble in DMF.

The solvent was evaporated and the precipitate washed with water, followed by freeze drying to obtain the dry oligomers and co-oligomers.

The recipe for synthesis of oligomers of α-amino acid isomers having identical chiral configurations and co-oligomers formed from HMB isomers having a specific chiral configuration and α-amino acid isomers having identical chiral configurations is summarized below in Table 12.

TABLE 12

Recipe for the Synthesis and Purification of L-Met Oligomers and L-HMB-L-Met Co-Oligomers From Racemic Mixtures of D, L-MetOEt and D, L-HMB-OEt

| | | MetOEt/HMB-OEt | |
|---|---|---|---|
| Components | MW | Moles | Wt |
| AA-ester | | | 3 g |
| L-Cys.HCl.H$_2$O | 175.6 | 100 mM | 0.1756 g |
| EDTA (anhyd) | 292.0 | 10 mM | 0.0292 g |
| Na Citrate | 294.1 | 1 M | 2.941 |
| Papain | 21428D | 7*10$^{-5}$ M | 15 mg |
| Volume | | | 10 mL |
| pH | | | 5.5 |

Hydrolysis of Met Oligomers and Met/HMB Co-Oligomers

A 25 mg aliquot of purified oligomers and co-oligomers obtained from the racemic Met-OEt and HMB-OEt was placed in 10 mL vials and hydrolyzed with 2 mL of 6.05(N) HCl at 110° C. for 24 hours. The clear solutions obtained after hydrolysis were diluted with nanopure water and injected in an LC equipped a diode array detector (DAD).

Enantioselective HPLC

Enantioselective HPLC analysis was carried out with a proline-Cu based column EC 250/4 Nucleosil Chiral 1 (Macherey-Nagel, Inc., Easton, Pa.). The mobile phase consisted of 0.5 mM cupric sulfate (pentahydrate) solution in nanopure water. Column oven temperature was maintained at 60° C. Separated analytes were monitored with a UV absorbance DAD.

Results

Figure 51:
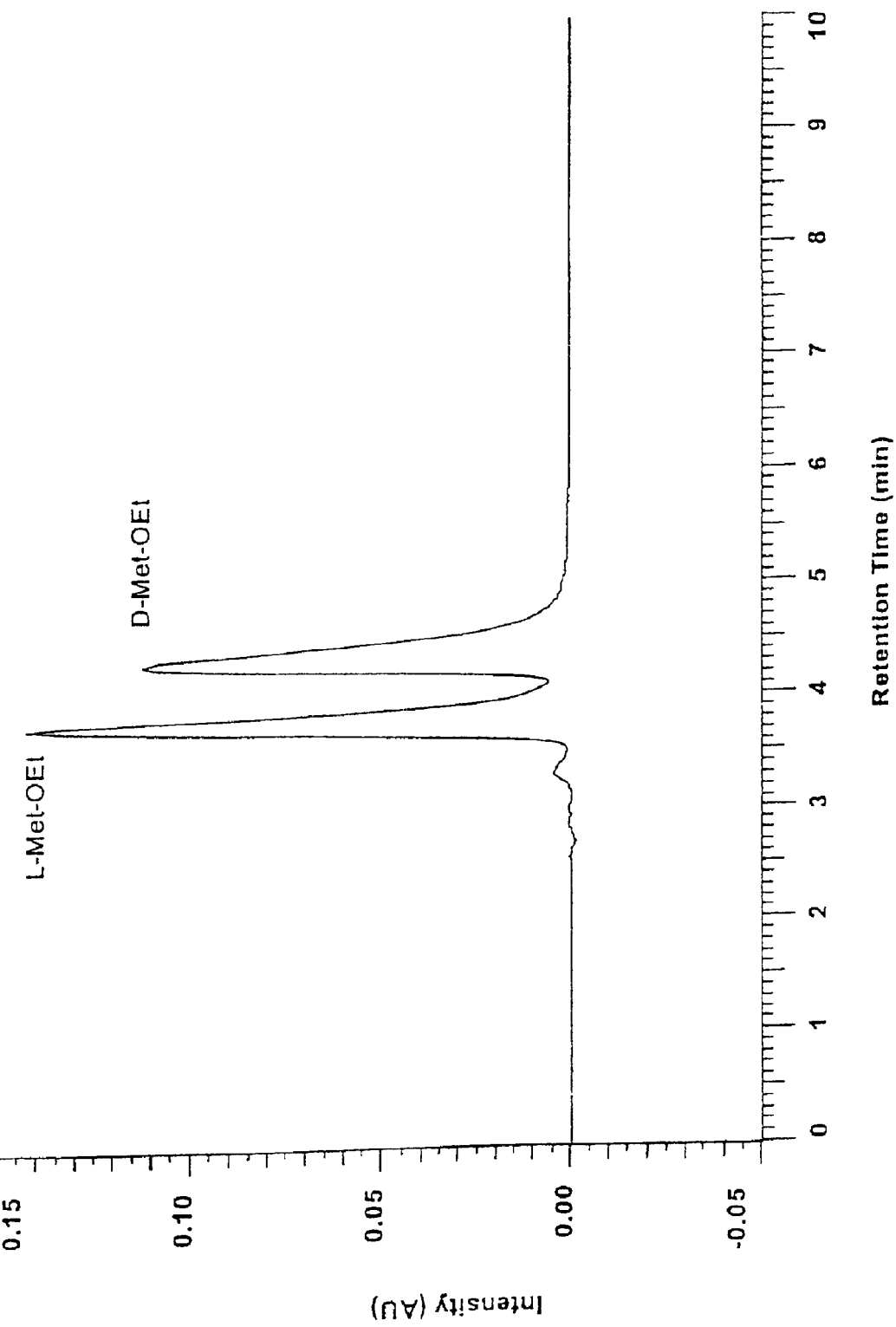
FIG. 51 is a chromatogram of an enantiomeric mixture of methionine ethyl ester using a UV absorption diode array detector (DAD).
Figure 52:
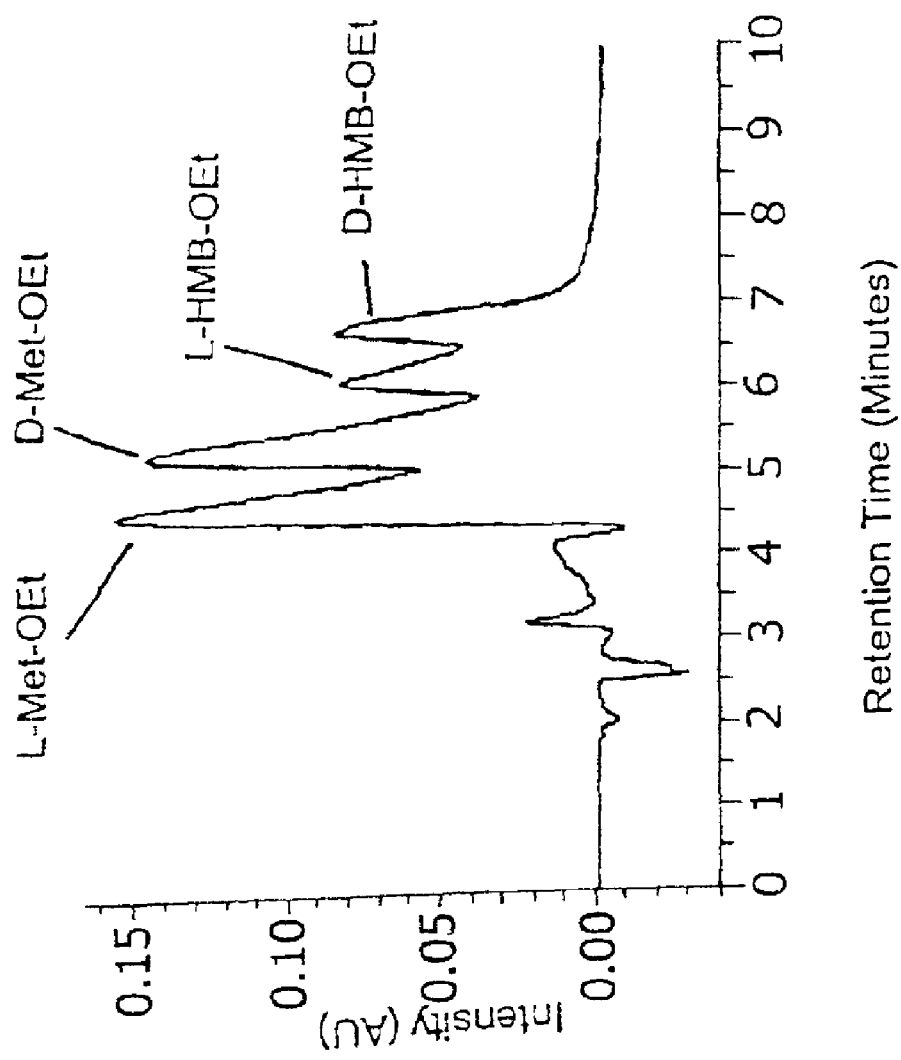
FIG. 52 is a chromatogram of a enantiomeric mixture of methionine ethyl ester and HMB-ethyl ester using a UV absorption diode array detector (DAD).

The HPLC results showed that the Met-OEt and HMB-OEt reactants were racemic mixtures that contained equal amounts of D- and L-Met ethyl ester enantiomers and D- and L-HMB ethyl ester enantiomers. See FIGS. 51 and 52. Following oligomerization and co-oligomerization and separation of the precipitates, the supernatant was analyzed and found to contain significantly higher concentrations of D-Met and D-HMB than L-Met and L-HMB. The relative concentrations of D-Met and L-Met were found to be approximately 97%: <2.5% respectively. The relative concentrations of D-HMB and L-HMB were found to be approximately 75% and 25% respectively.

Figure 53:
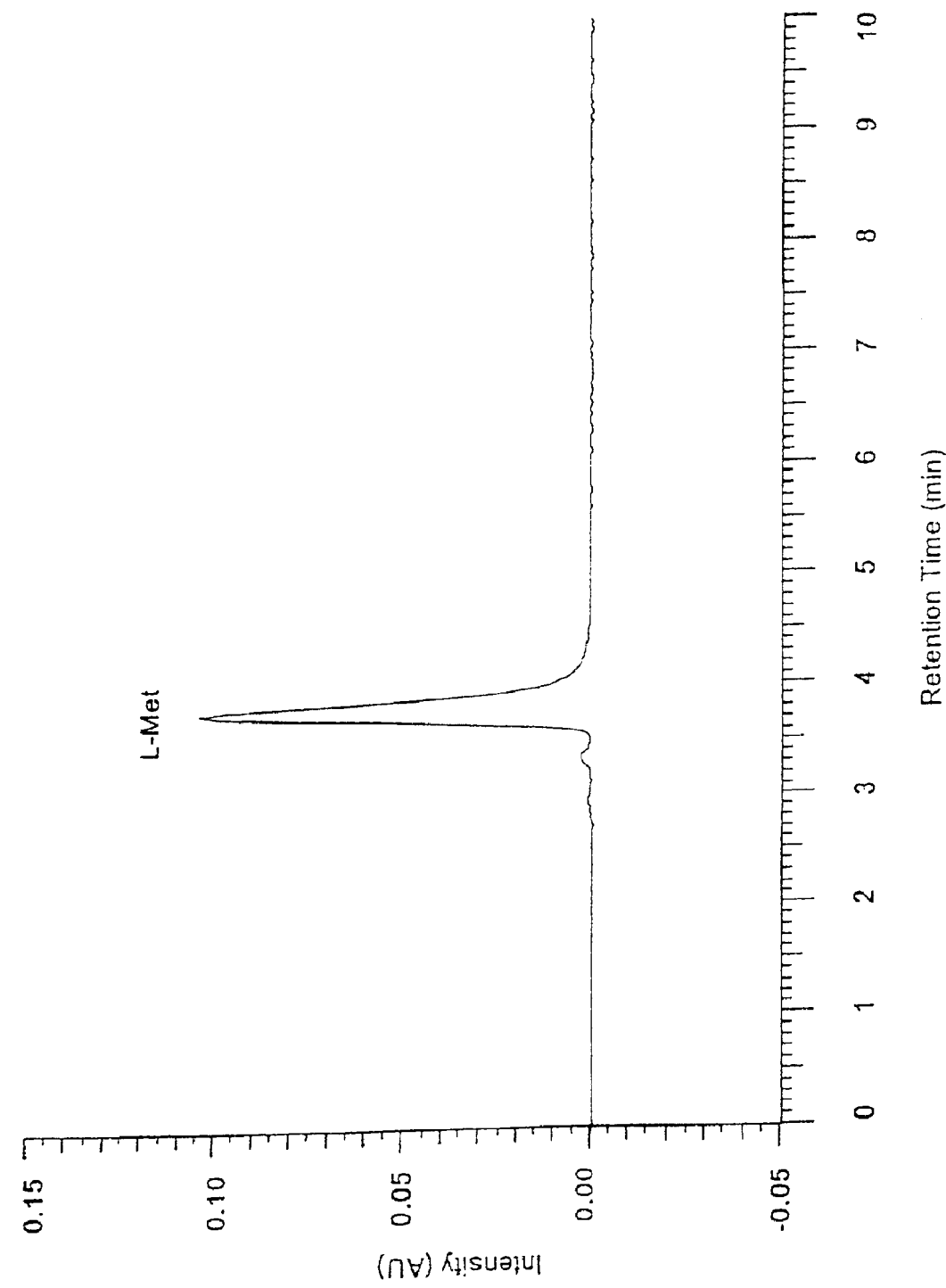
FIG. 53 is a chromatogram of an oligomer and co-oligomer hydrolyzate illustrating the presence of only the L-methionine enantiomer using a UV absorption diode array detector (DAD).
Figure 54:
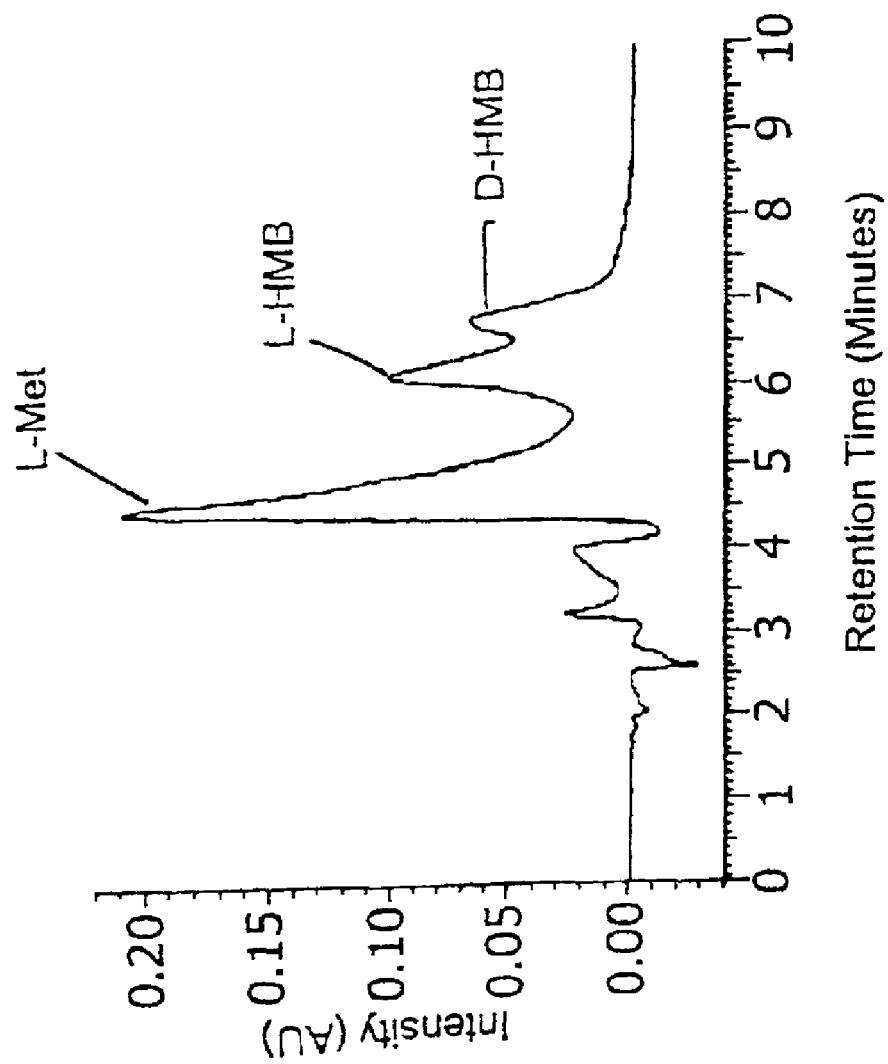
FIG. 54 is a chromatogram of an oligomer and co-oligomer hydrolyzate illustrating the presence of only the L-HMB enantiomer using a UV absorption diode array detector (DAD).

The selective oligomerization and co-oligomerization of L-Met and L-HMB were observed in the results from the enantioselective HPLC analysis. The analysis indicated that the oligomer and co-oligomer hydrolyzate was found to contain only the L-Met and the L-HMB isomers. See FIGS. 53 and 54. While FIG. 54 indicates the presence of a D-HMB isomer peak, when the precipitate was washed, dissolved in DMSO, and reprecipitated, the D-HMB isomer peak disappeared, indicating that the D-HMB present was initially absorbed to the oligomer and co-oligomer precipitate, but was not covalently bonded within the oligomer and co-oligomer precipitate.

Example 15
Papain Catalyzed Synthesis of Lactic Acid-Amino Acid Oligomers

This example demonstrates the synthesis of co-oligomers comprising lactic acid (an α-hydroxy carboxylic acid) with oligomers of the α-amino acids methionine, leucine, tyrosine, phenylalanine and tryptophan.

The experiment consisted of esterifying D,L-Lactic acid with acidified ethyl alcohol by refluxing it at 80° C. for 8 hrs to produce lactic acid ethyl ester, which was used in each of the oligomerization reactions. The oligomerization consisted of forming a mixture by dissolving each of the amino acid ethyl esters and the lactic acid ethyl ester in various amounts in a pH 5.5 buffer containing, L-cysteine, EDTA and sodium citrate as shown in the tables below. At the end of 24 hours, the mixture was heated to 80° C. for 10 mins to denature the enzyme. The supernatant was analyzed on RPLC to determine the yield of the reaction. The precipitate was washed thoroughly with water to obtain a monomer (amino acid and lactic acid) free product. The product was freeze dried and a small part of it was dissolved in DMSO and introduced into the ESI-MS and the mass spectrum obtained was recorded.

1. Lactic Acid-Methionine Co-Oligomerization

Lactic acid-methionine oligomers were synthesized using the general procedure described above. The ingredients for the oligomerization reaction mixture consisted of the following:

| Composition | |
|---|---|
| L-MetEE-HCl (g) | 1.5 |
| LAEE (g) | 1.5 |
| L-Cysteine (mg) | 175.6 |
| EDTA (mg) | 29.2 |
| Sodium Citrate (g) | 2.9 |
| Papain (mg) | 30.0 |
| Total Volume (ml) | 10.0 |

Figure 55A:
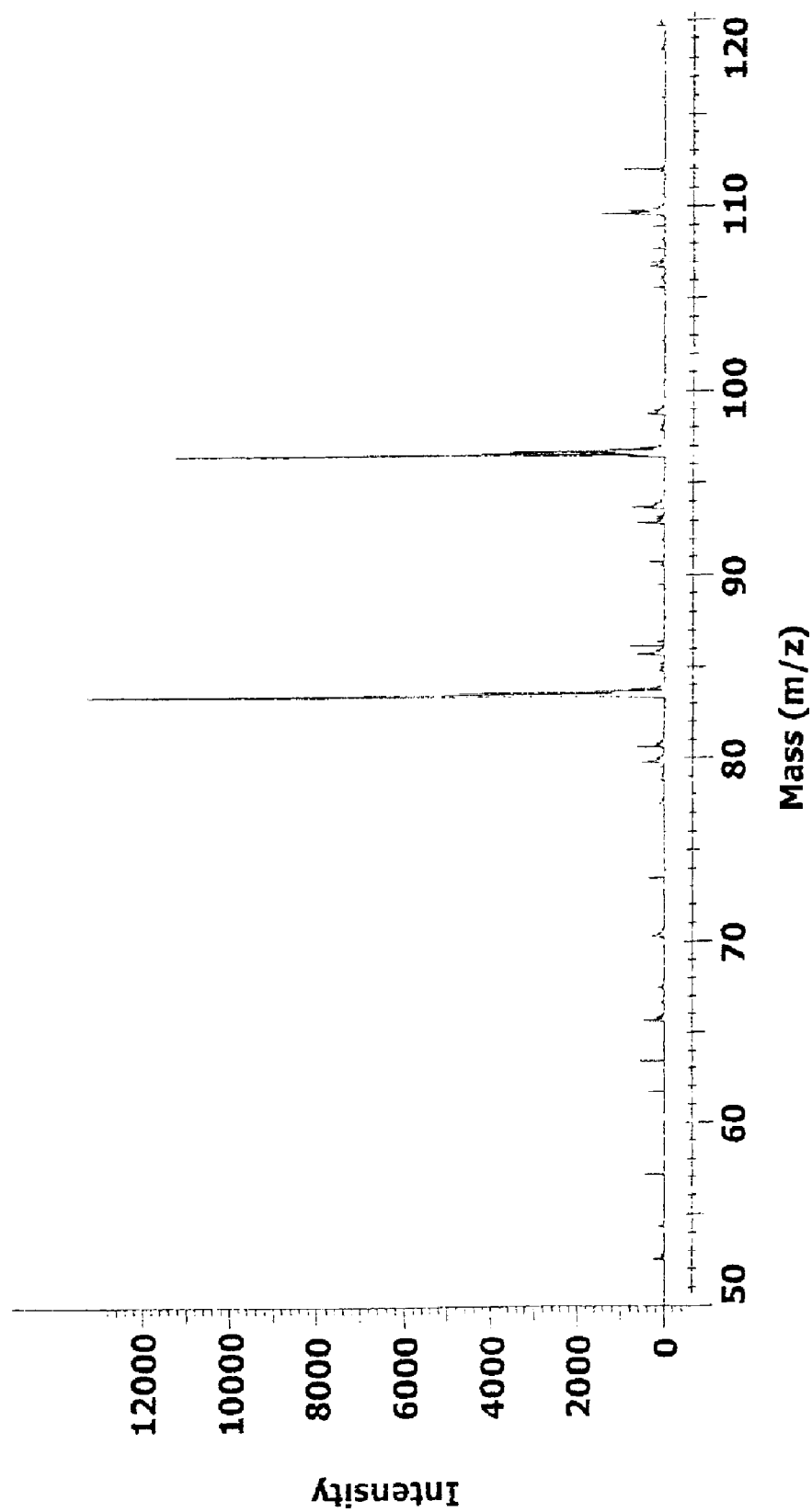
FIG. 55A is a positive ion ESI-MS spectra of the lactic acid—methionine oligomers prepared in Example 15.
Figure 55B:
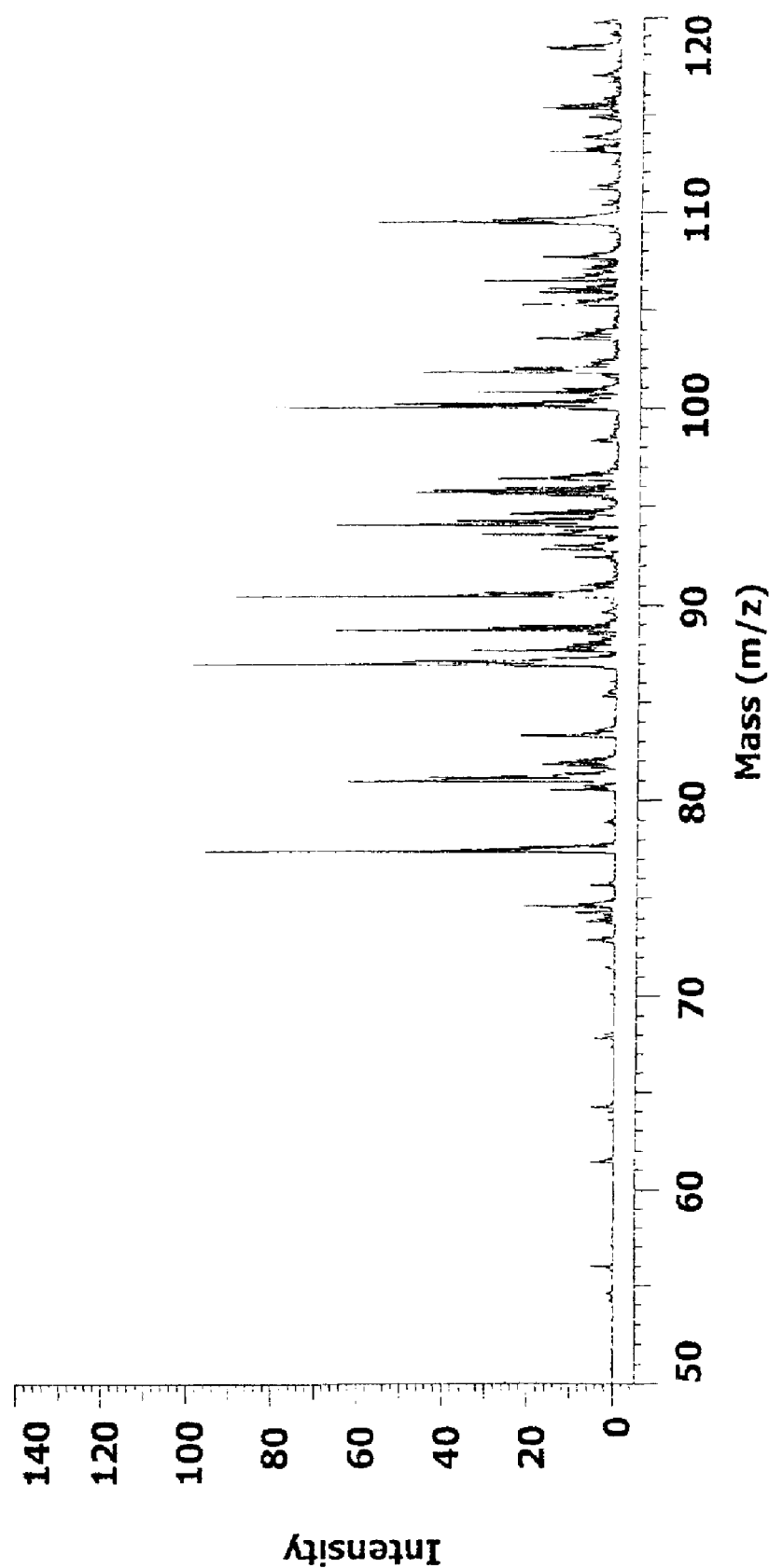
FIG. 55B is a negative ion ESI-MS spectra of the lactic acid—methionine oligomers prepared in Example 15.

The oligomerization produced an yield of 75% and the positive ion and negative ion spectra are reproduced in FIGS. 55A and 55B respectively. The positive ion spectrum shows the presence of 2 dominant peaks at 834 and 965. These peaks most probably represent the homo-oligomers, $^N$Met-(Met)$_4$-Met$^C$-OEt and $^N$Met-(Met)$_5$-Met$^C$-OEt respectively which are separated by the repeating methionine residue unit of mass 131.2.

The negative ion spectrum shows the presence of a series of peaks each separated by around 131 mass units. One set of peaks appear at 774 and 905 and these most probably represent the deprotonated ions, $^N$LA-(Met)$_4$-Met$^C$-OEt and $^N$LA-(Met)$_5$-Met$^C$-OEt respectively. Another set of ions, appear at 809 and 940 and these mot probably represent the adducts of the above co-oligomers with the chloride ion.

2. Lactic Acid-Tyrosine Co-Oligomerization

Lactic acid-tyrosine oligomers were synthesized using the general procedure described above. The ingredients for the oligomerization reaction mixture consisted of the following:

| Composition | |
|---|---|
| L-TyrEE-HCl (mg) | 466.8 |
| LAEE (mg) | 466.8 |
| L-Cysteine (mg) | 175.6 |
| EDTA (mg) | 29.2 |
| Sodium Citrate (g) | 2.9 |
| Papain (mg) | 30.0 |
| Total Volume (ml) | 10.0 |

Figure 56A:
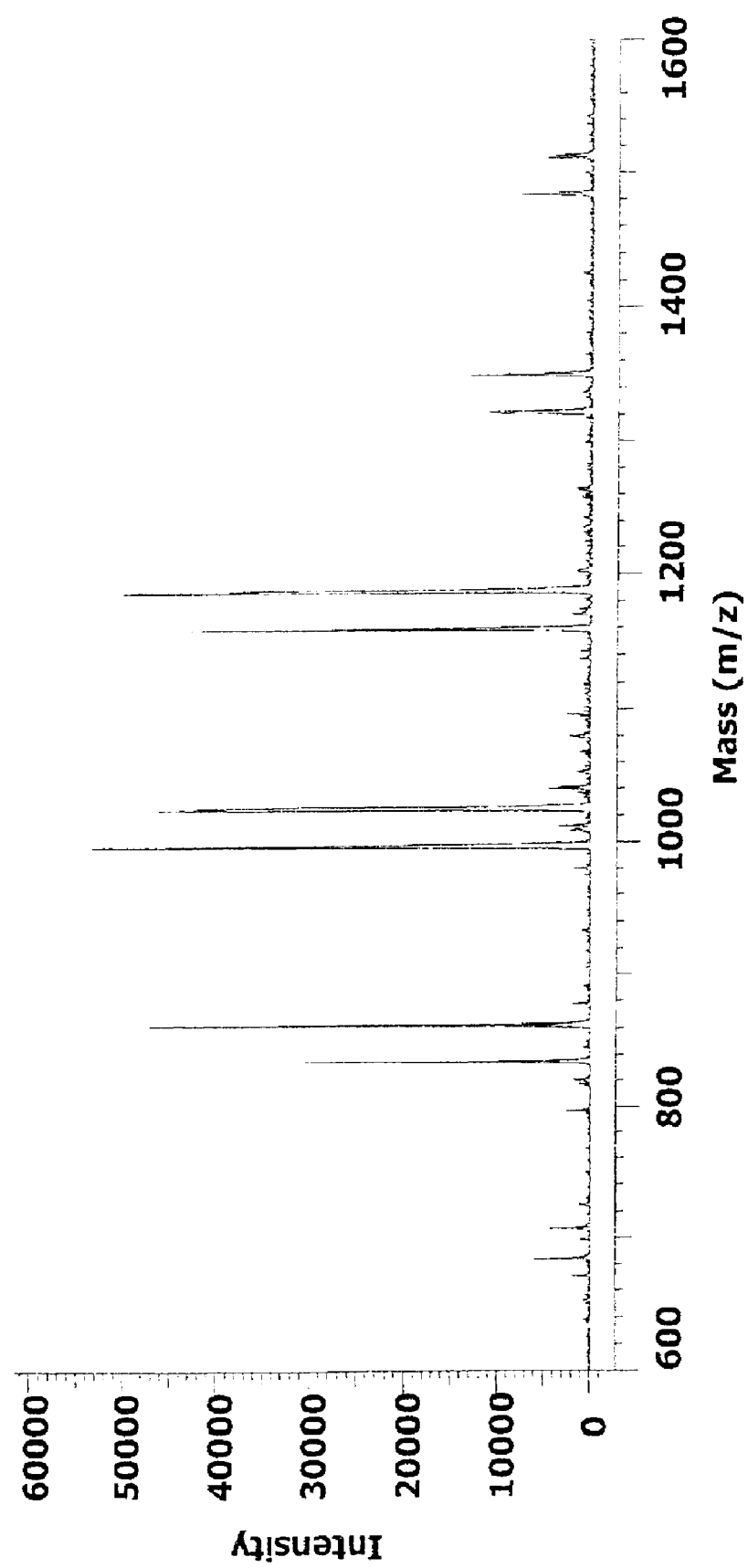
FIG. 56A is a positive ion ESI-MS spectra of the lactic acid—tyrosine oligomers prepared in Example 15.
Figure 56B:
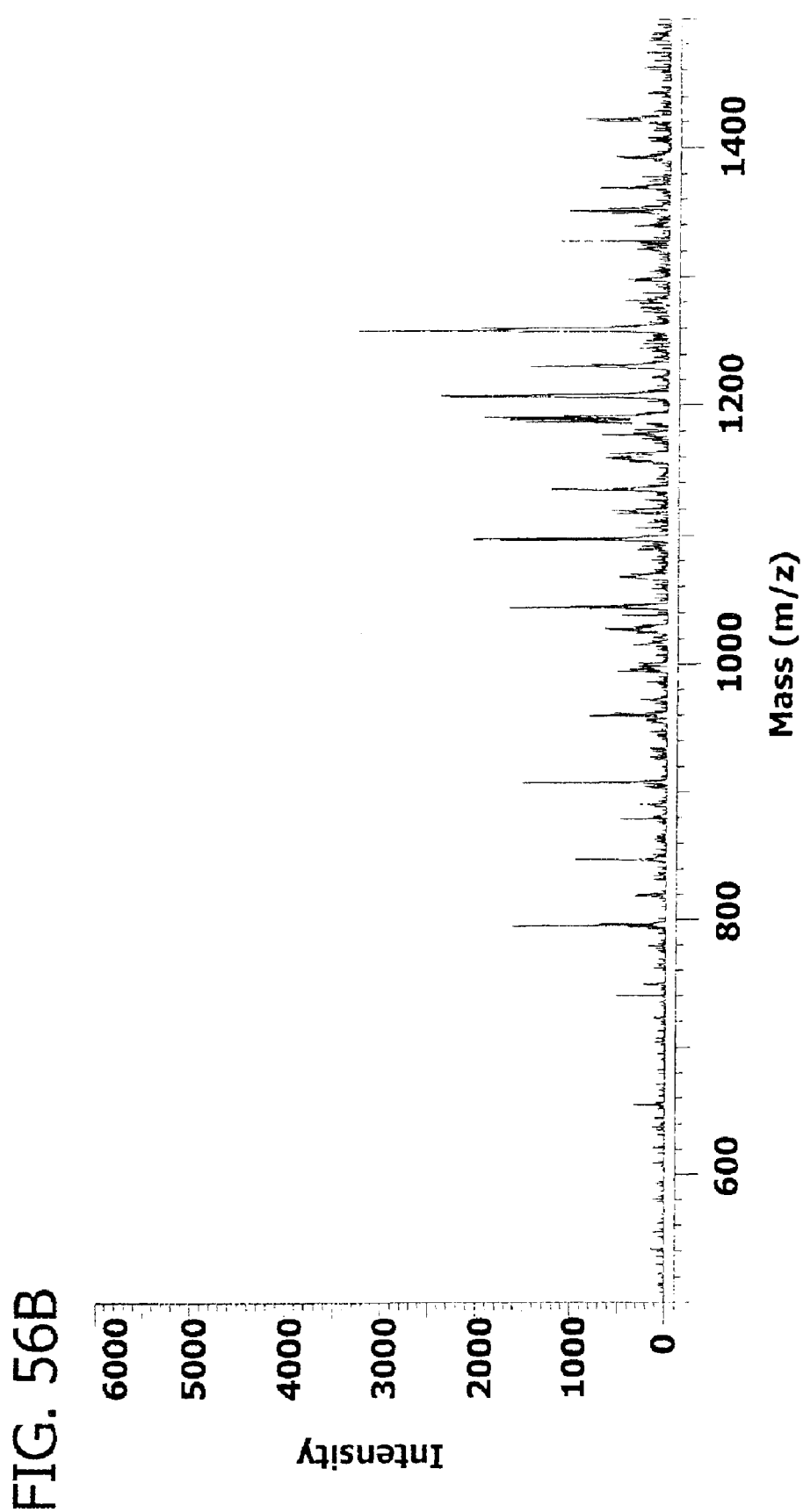
FIG. 56B is a negative ion ESI-MS spectra of the lactic acid—tyrosine oligomers prepared in Example 15.

A yield of 98% with respect to tyrosine was obtained. The positive ion and negative ion spectra are provided in FIG. 56A and 56B respectively. The positive ion spectra shows the presence of a evenly spaced sets of two peaks with each peak separated from the other by 28 amu. This mass represents the difference in mass between C-terminal free acid and ethyl ester. Each set of peaks is separated by a mass of 163 units with is the repeating unit of the tyrosine residue. While one set appeared at 833, 996, 1159 and 1322 most probably representing the protonated homo-oligomers of tyrosine namely, $^N$Tyr-Tyr$_3$-Try$^C$-OH, $^N$Try-Tyr$_4$-Tyr$^C$-OH, $^N$Tyr-Tyr$_5$-Tyr$^C$-OH and $^N$Tyr-Tyr$_6$-Tyr$^C$-OH, another set appeared 861, 1024 and 1187 and these most probably represent the protonated forms of Ntyr-Tyr$_3$-Tyr$^C$-OEt, $^N$tyr-Tyr$_4$-Tyr$^C$-OEt and Ntyr-Tyr$_5$-Tyr$^C$-OEt respectively. The negative ion spectrum reveals a number of peaks with some of them forming a series separated by 163 units. One set appears at 1096, 1259 and 1422 and these most probably represent the presence of deprotonated co-oligomer ions formed from $^N$LA-Tyr$_5$-Tyr$^C$-OEt,$^N$LA-Tyr$_6$-Tyr$^C$-OEt and $^N$LA-Tyr$_7$-Tyr$^C$-OEt respectively.

3. Lactic Acid-Leucine Co-Oligomerization

Lactic acid-leucine oligomers were synthesized using the general procedure described above. The ingredients for the oligomerization reaction mixture consisted of the following:

| Composition | |
|---|---|
| L-LeuEE-HCl (mg) | 684.5 |
| LAEE (mg) | 684.5 |
| L-Cysteine (mg) | 175.6 |
| EDTA (mg) | 29.2 |
| Sodium Citrate (g) | 2.9 |
| Papain (mg) | 30.0 |
| Total Volume (ml) | 10.0 |

Figure 57A:
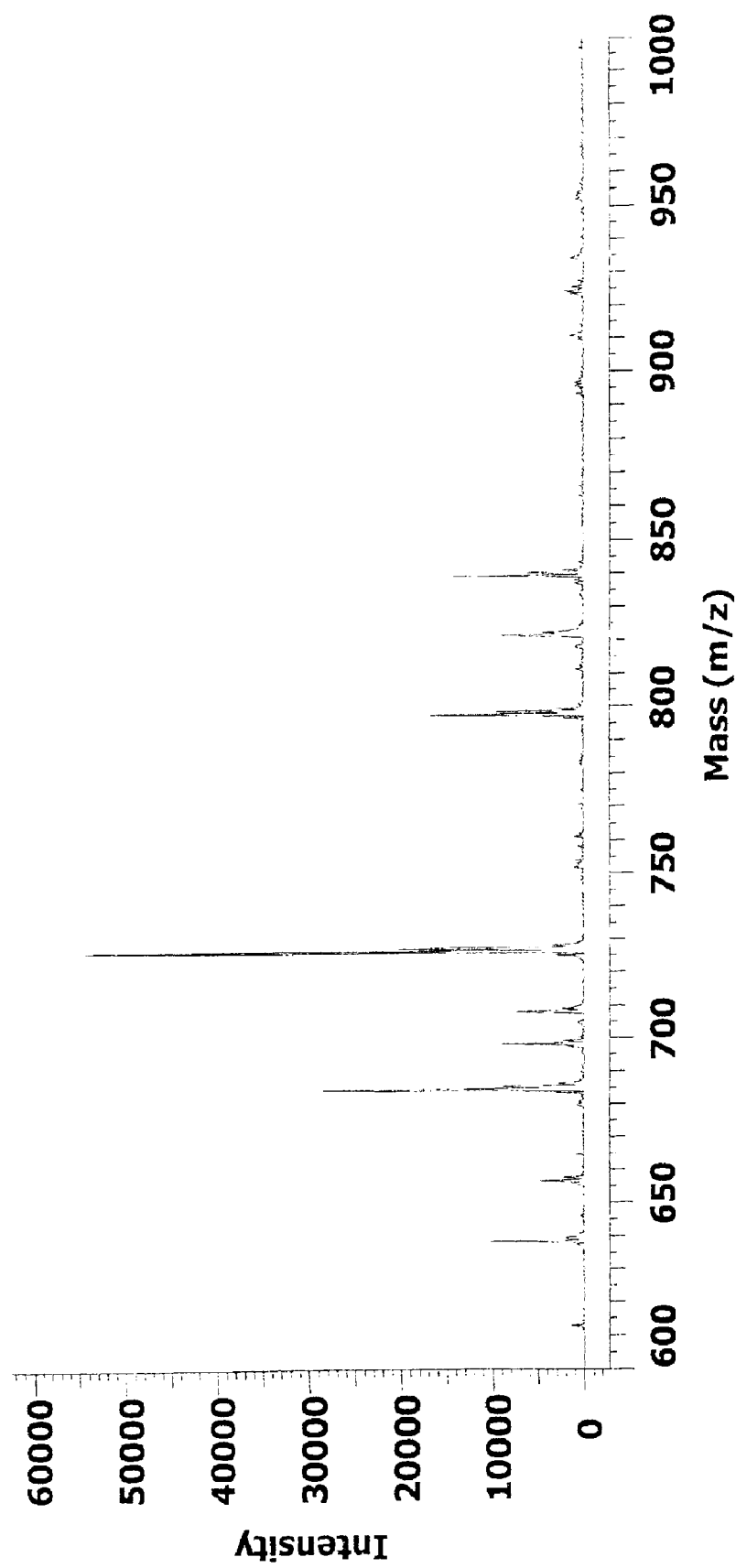
FIG. 57A is a positive ion ESI-MS spectra of the lactic acid—leucine oligomers prepared in Example 15.
Figure 57B:
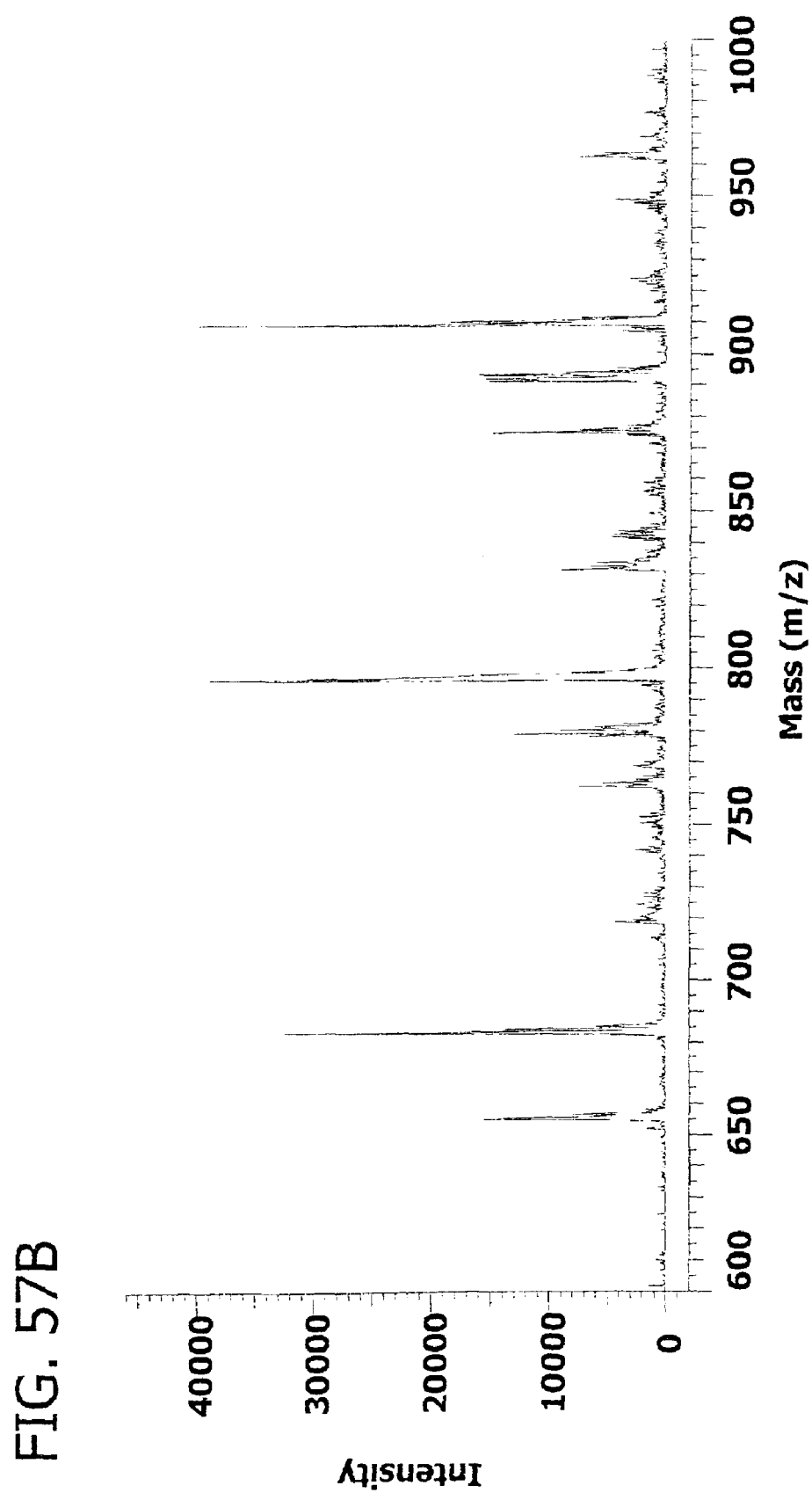
FIG. 57B is a negative ion ESI-MS spectra of the lactic acid—leucine oligomers prepared in Example 15.

The oligomerization produced a yield of 40% with respect to leucine. The positive and negative ion specta are provided in FIGS. 57A and 57B respectively. The positive ion spectrum has a pair of peaks at 726 and 839 and these ions are separated by the repeating residue unit of leucine (113 amu) and they most probably represent the protonated ions of homo-oligomers, $^N$Lleu-Leu$_4$-Leu$^C$-OEt and $^N$Leu-Leu$_5$-Leu$^C$-OEt respectively. Another ion appears at 698 and this is most probably the protonated ion of the homo-oligomer $^N$Leu-Leu$_4$-Leu$^C$-OH. In addition to these peaks, another pair of peaks appear at 685 and 798 and these are again separated by the repeating unit of leucine and these most probably correspond to the protonated forms of the co-oligomer peaks, $^N$LA-Leu$_4$-Leu$^C$-OEt and $^N$LA-Leu$_5$-Leu$^C$-OEt respectively. The peaks corresponding to $^N$LA-Leu$_4$-Leu$^C$-OH$^+$H$^+$ and $^N$LA-Leu$_5$-Leu$^C$-OEt+Na$^+$ appear at 657 and 821 respectively. The negative ion spectrum reveals a series of peaks each separated by 113 amu. These appear at 683, 796 and 909 and they most probably represent the deprotonated forms of the co-oligomers $^N$LA-Leu$_4$-Leu$^C$-OEt-$^N$LA-Leu$_5$-Leu$^C$-OEt and $^N$LA-Leu$_6$-Leu$^C$-OEt respectively.

4. Lactic Acid-Tryptophan Co-Oligomerization

Lactic acid-tryptophan oligomers were synthesized using the general procedure described above. The ingredients for the oligomerization reaction mixture consisted of the following:

| Composition | |
| --- | --- |
| L-TrpEE-HCl (mg) | 480.0 |
| LAEE (mg) | 480.0 |
| L-Cysteine (mg) | 175.6 |
| EDTA (mg) | 29.2 |
| Sodium Citrate (g) | 2.9 |
| Papain (mg) | 30.0 |
| Total Volume (ml) | 10.0 |

Figure 58A:
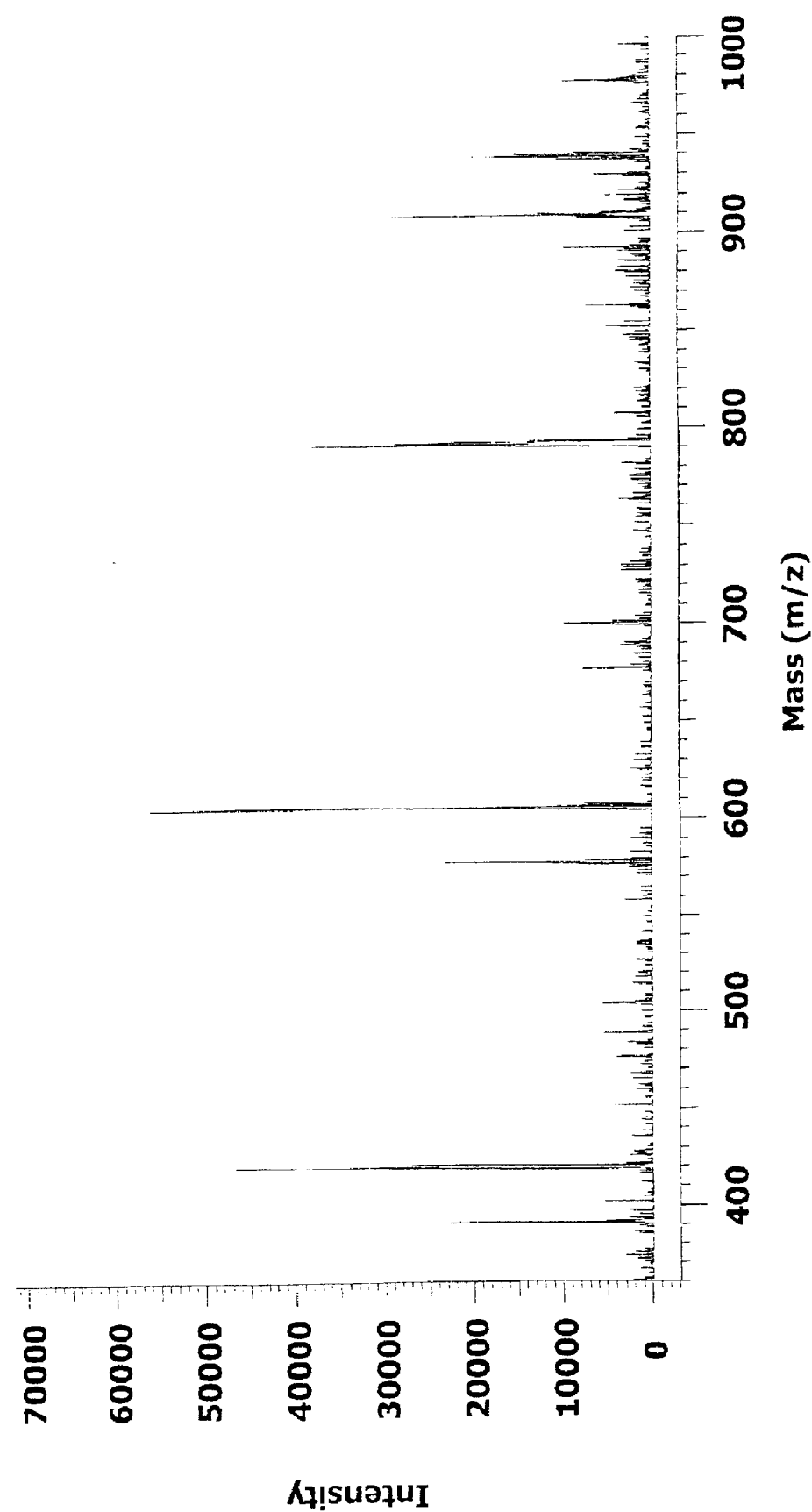
FIG. 58A is a positive ion ESI-MS spectra of the lactic acid—tryptophan oligomers prepared in Example 15.
Figure 58B:
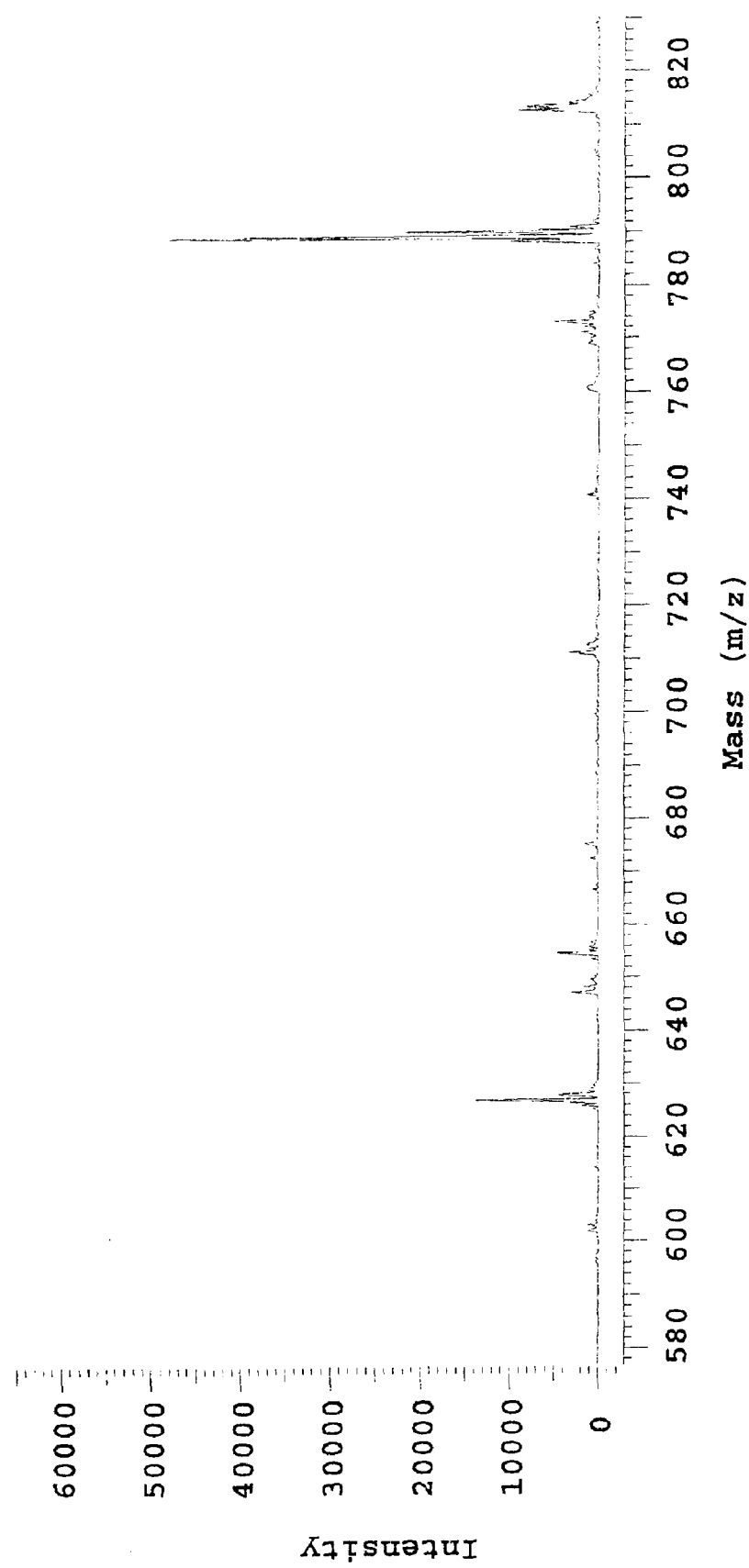
FIG. 58B is a negative ion ESI-MS spectra of the lactic acid—tryptophan oligomers prepared in Example 15.

An oligomerization yield of 94% was obtained with respect to tryptophan. The positive ion and negative ion spectra are produced in FIGS. 58A and 58B respectively. A series of ions separated b 186 units at 419, 605, 791 and 977 appears in the positive ion spectrum. These indicate the presence of the protonated homo-oligomers of the form $^N$Trp$_n$-Trp$^c$-OEt with n 1 to 5. The $^N$Trp-Trp-Trp$^C$-OH+H$^+$ ion appears at 577. The ion at 700 most probably represent the lone co-oligomer peak of $^N$LA-Trp$_2$-Trp$^C$-OEt+Na$^+$. The negative ion spectrum shows the presence of deprotonated $^N$Trp-Trp$_2$-Trp$^C$-OEt as the base peak at 789. However, neither of the spectra does show explicitly show the presence of co-oligomer peaks. Further work with LC-MS needs to be done to separate the oligomer from the co-oligomers and prove the presence/absence of the co-oligomers.

5. Lactic Acid-Phenylalanine Co-Oligomerization

Lactic acid-phenylalanine oligomers were synthesized using the general procedure described above. The ingredients for the oligomerization reaction mixture consisted of the following:

| Composition | |
| --- | --- |
| L-PheEE-HCl (mg) | 570.7 |
| LA-IPA (mg) | 570.7 |
| L-Cysteine (mg) | 175.6 |
| EDTA (mg) | 29.2 |
| Sodium Citrate (g) | 2.9 |
| Papain (mg) | 30.0 |
| Total Volume (ml) | 10.0 |

Figure 59A:
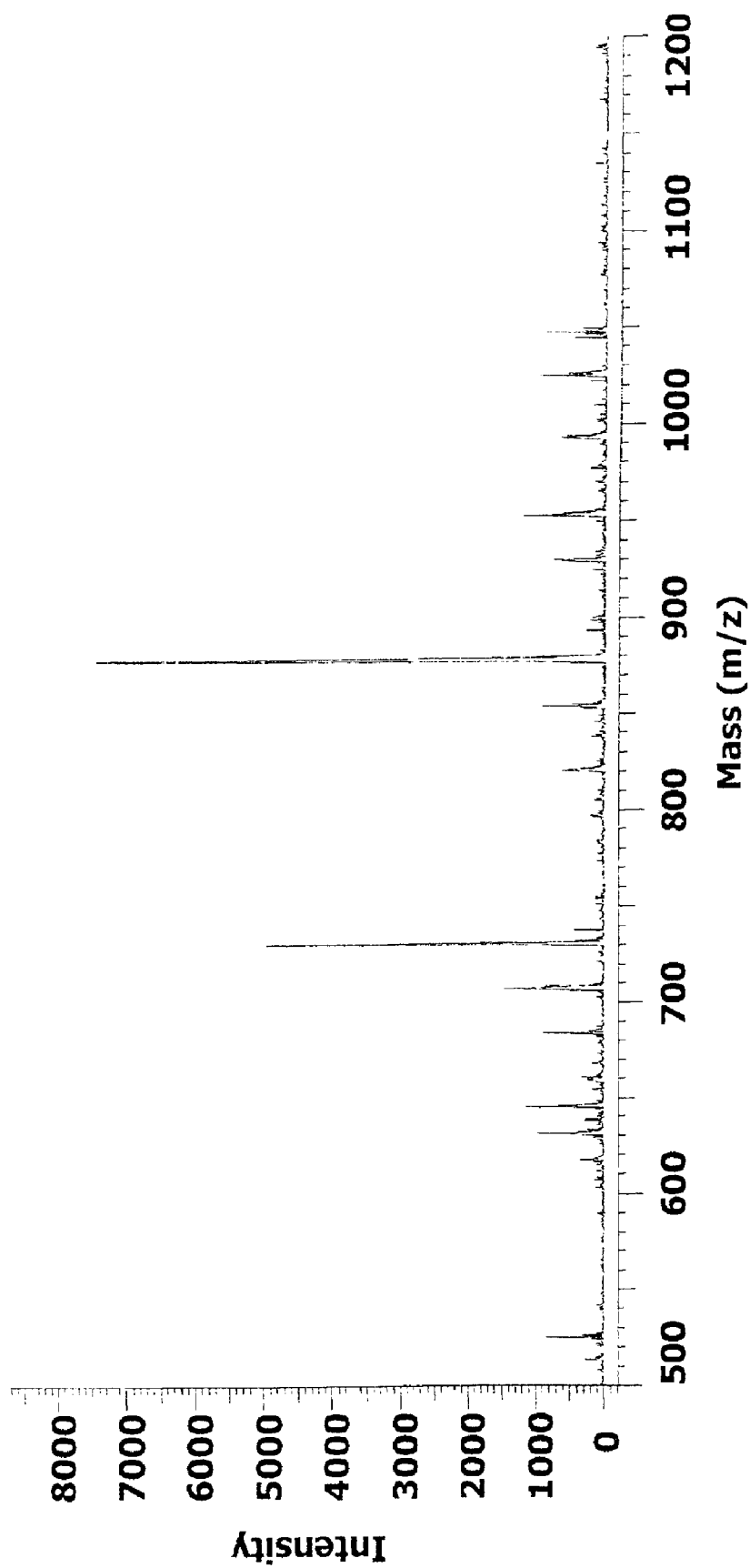
FIG. 59A is a positive ion ESI-MS spectra of the lactic acid—phenylalanine oligomers prepared in Example 15.
Figure 59B:
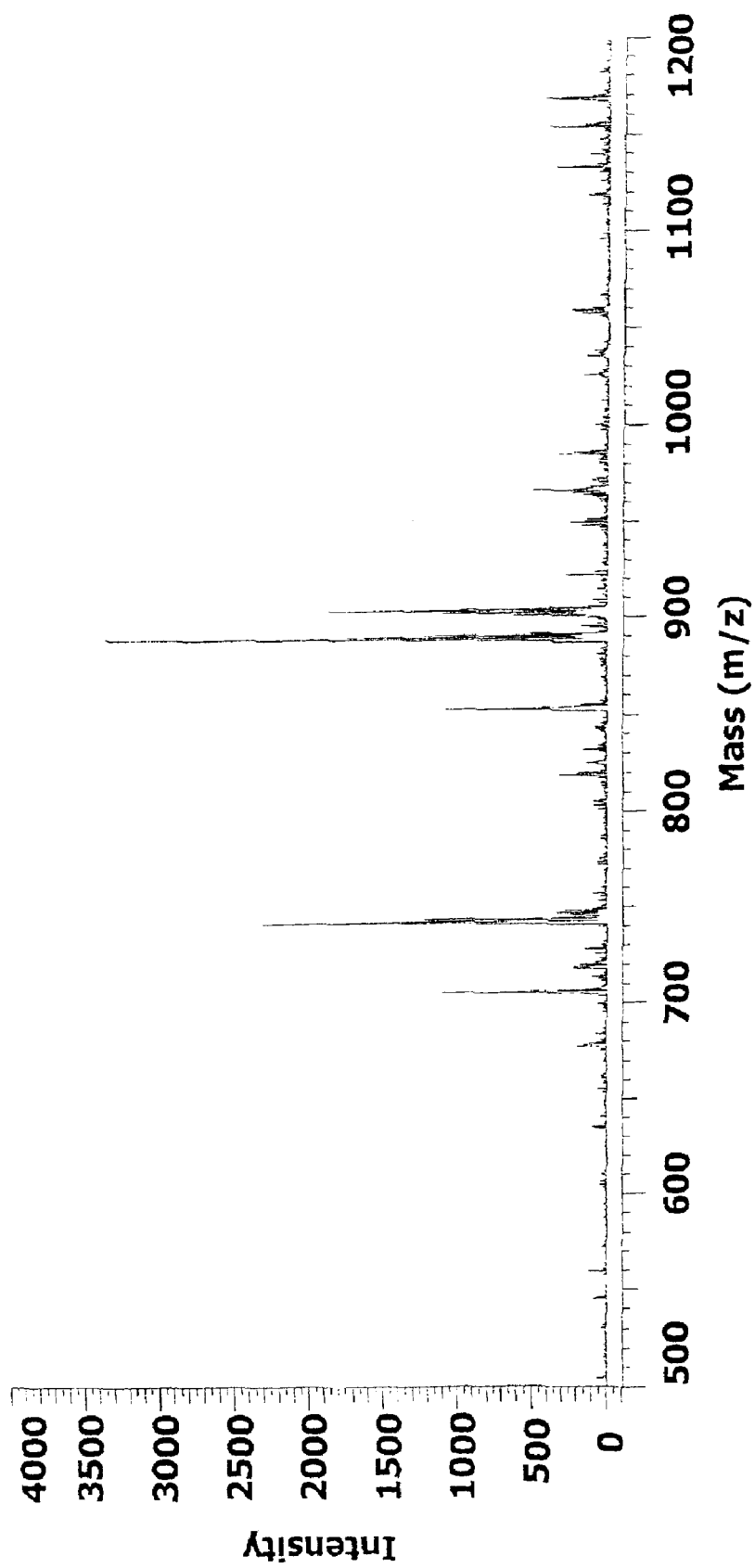
FIG. 59B is a negative ion ESI-MS spectra of the lactic acid—phenylalanine oligomers prepared in Example 15.

The lactic acid was esterified with iso-propyl alcohol and was used along with the phenylalanine ethyl ester. An oligomerization yield of 80% was obtained with respect to phenylalanine. The positive and negative ion spectrum is provided in FIGS. 59A and 59B respectively. The positive ion spectrum reveals the strong presence of sodiated co-oligomers ions of $^N$LA-(Phe)$_3$-Phe$^C$-OEt+Na$^+$ and $^N$LA-(Phe)$_4$-Phe$^C$-OEt+Na$^+$ at masses 730 and 877 respectively. These peaks are separated by 147 units, which is the repeating residue unit of phenylalanine. The absence of any oligomer peaks is due to fact that the phenylaline does not oligomerize without a N-terminal starter molecule. This points to the presence of LA at the N-terminal end of the oligomer. The presence of ethyl ester (and absence of the iso-propyl ester) at the C-terminal end also reinforces this result. The negative ion spectrum reveals two sets of peaks with each set separated by 147 units. These sets represent the deprotonated co-oligomer peaks to form $^N$LA-Phe$_n$-Phe$^C$-OEt with n having values of 3 and 4.

In view of the above, it will be seen that the several objects of the invention are achieved. As various changes could be made in the above compositions and methods without departing from the scope of the invention, it is intended that all matter contained in the above description be interpreted as illustrative and not in a limiting sense.

What is claimed is:

1. A process for the preparation of an oligomer, the process comprising:

forming a reaction mixture comprising an enzyme, an enantiomeric mixture of an α-amino acid or a derivative thereof, and an enantiomeric mixture of an α-hydroxy carboxylic acid or a derivative thereof, wherein the α-hydroxy carboxylic acid comprises 2-hydroxy-4-(methylthio)butyric acid or a derivative thereof; and forming an oligomer from the reaction mixture, said oligomer incorporating one of the members of the enantiomeric mixture of the α-amino acid or derivative thereof in preference to the other member.

wherein the formed oligomer comprises an oligomer of two or more α-amino acid monomers bonded to a residue of the α-hydroxy carboxylic acid or a derivative thereof by an amide or ester linkage.

* * * * *